United States Patent
Peled et al.

(10) Patent No.: US 10,047,345 B2
(45) Date of Patent: Aug. 14, 2018

(54) CULTURING OF MESENCHYMAL STEM CELLS WITH FGF4 AND NICOTINAMIDE

(71) Applicant: Gamida-Cell Ltd., Jerusalem (IL)

(72) Inventors: Tony Peled, Mevaseret Zion (IL); Yair Steinhardt, Kfar-Saba (IL)

(73) Assignee: Gamida-Cell Ltd., Jerusalem (IL)

( * ) Notice: Subject to any disclaimer, the term of this patent is extended or adjusted under 35 U.S.C. 154(b) by 474 days.

(21) Appl. No.: 14/378,235

(22) PCT Filed: Feb. 13, 2013

(86) PCT No.: PCT/IL2013/050136
§ 371 (c)(1),
(2) Date: Aug. 12, 2014

(87) PCT Pub. No.: WO2013/121426
PCT Pub. Date: Aug. 22, 2013

(65) Prior Publication Data
US 2015/0004146 A1    Jan. 1, 2015

Related U.S. Application Data

(60) Provisional application No. 61/597,899, filed on Feb. 13, 2012, provisional application No. 61/597,909, filed on Feb. 13, 2012.

(51) Int. Cl.
*C12N 5/00* (2006.01)
*C12N 5/0775* (2010.01)
*A61K 35/28* (2015.01)
*A61K 35/12* (2015.01)

(52) U.S. Cl.
CPC ............ *C12N 5/0667* (2013.01); *A61K 35/28* (2013.01); *C12N 5/0663* (2013.01); *A61K 2035/124* (2013.01); *C12N 2500/38* (2013.01); *C12N 2501/119* (2013.01); *C12N 2502/1358* (2013.01); *C12N 2502/1382* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 3,715,345 A | 2/1973 | Smith |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,863,008 A | 1/1975 | Grant |
| 3,867,517 A | 2/1975 | Ling |
| 3,876,623 A | 4/1975 | Jackson et al. |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,036,945 A | 7/1977 | Haber |
| 4,098,876 A | 7/1978 | Piasio et al. |
| 4,331,647 A | 5/1982 | Goldenberg |
| 4,469,863 A | 9/1984 | Ts'o et al. |
| 4,476,301 A | 10/1984 | Imbach et al. |
| 4,642,120 A | 2/1987 | Nevo et al. |
| 4,666,828 A | 5/1987 | Gusella |
| 4,683,202 A | 7/1987 | Mullis |
| 4,687,808 A | 8/1987 | Jarrett et al. |
| 4,801,531 A | 1/1989 | Frossard |
| 4,806,484 A | 2/1989 | Petrossian et al. |
| 4,816,567 A | 5/1989 | Cabilly et al. |
| 4,866,052 A | 9/1989 | Hider et al. |
| 4,868,116 A | 9/1989 | Morgan et al. |
| 4,879,219 A | 11/1989 | Wands et al. |
| 4,946,778 A | 8/1990 | Ladner et al. |
| 4,980,286 A | 12/1990 | Morgan et al. |
| 5,011,771 A | 4/1991 | Bellet et al. |
| 5,013,830 A | 5/1991 | Ohtsuko et al. |
| 5,023,243 A | 6/1991 | Tullis |
| 5,034,506 A | 7/1991 | Summerton et al. |
| 5,081,035 A | 1/1992 | Halberstadt et al. |

(Continued)

FOREIGN PATENT DOCUMENTS

AU    759522    7/2003
AU    770896    6/2004

(Continued)

OTHER PUBLICATIONS

Diani-Moore et al. "Identification of the Aryl Hydrocarbon Receptor Target Gene TiPARP as a Mediator of Suppression of Hepatic Gluconeogenesis by 2,3,7,8-Tetrachlorodibenzo-P-Dioxin and of Nicotinamide as a Corrective Agent for This Effect", The Journal of Biological Chemistry, 285(50): 38801-38810, Published Online, (Sep. 28, 2010).

"13th Annual Meeting on Surgical Research." Langenbeck's Archives of Surgery. 394.5(2009):915-970.

Bonora-Centelles et al. "Sequential Hepatogenic Transdifferentiation of Adipose Tissue-Derived Stem Cell: Relevance of Different Extracellular Signaling Molecules, Transcription Factors Involved, and Expression of New Key Marker Genes." Cell Transplant.18. 12(2009):1319-1340.

Bonora-Centelles et al. "Sequential Hepatogenic Transdifferentiation of Adipose Tissue-Derived Stem Cell: Relevance of Different Extracellular Signaling Molecules, Transcription Factor Involved, and Expression of New Key Maker Genes." Cell Transplant 18.12 (2009): 1319-1340.

(Continued)

*Primary Examiner* — Blaine Lankford
(74) *Attorney, Agent, or Firm* — Cooley LLP; Ivor R. Elrifi; Matthew Pavao

(57) ABSTRACT

Methods of culturing mesenchymal stem cells are provided. The methods comprise culturing MSCs in a medium comprising nicotinamide and fibroblast growth factor 4 (FGF4). Populations of mesenchymal stem cells generated using the methods described herein and uses thereof are also provided.

13 Claims, 38 Drawing Sheets
(28 of 38 Drawing Sheet(s) Filed in Color)

(56) References Cited

U.S. PATENT DOCUMENTS

| | | |
|---|---|---|
| 5,149,797 A | 9/1992 | Pederson et al. |
| 5,166,315 A | 11/1992 | Summerton et al. |
| 5,166,320 A | 11/1992 | Wu et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen |
| 5,278,302 A | 1/1994 | Caruthers et al. |
| 5,281,521 A | 1/1994 | Trojanowski et al. |
| 5,286,717 A | 2/1994 | Cohen et al. |
| 5,320,963 A | 6/1994 | Knaack et al. |
| 5,321,131 A | 6/1994 | Agrawal et al. |
| 5,342,781 A | 8/1994 | Su |
| 5,366,878 A | 11/1994 | Pederson et al. |
| 5,378,725 A | 1/1995 | Bonjouklian et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,434,257 A | 7/1995 | Matteucci et al. |
| 5,437,994 A | 8/1995 | Emerson et al. |
| 5,453,496 A | 9/1995 | Caruthers et al. |
| 5,455,233 A | 10/1995 | Spielvogel et al. |
| 5,466,677 A | 11/1995 | Baxter et al. |
| 5,470,967 A | 11/1995 | Huie et al. |
| 5,476,925 A | 12/1995 | Letsinger et al. |
| 5,480,906 A | 1/1996 | Creemer et al. |
| 5,486,359 A | 1/1996 | Caplan et al. |
| 5,489,677 A | 2/1996 | Sanghvi et al. |
| 5,491,133 A | 2/1996 | Walder et al. |
| 5,504,103 A | 4/1996 | Bonjouklian et al. |
| 5,519,126 A | 5/1996 | Hecht |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,565,350 A | 10/1996 | Kmiec |
| 5,569,825 A | 10/1996 | Lonberg et al. |
| 5,571,799 A | 11/1996 | Tkachuk et al. |
| 5,587,361 A | 12/1996 | Cook et al. |
| 5,596,086 A | 1/1997 | Matteucci et al. |
| 5,602,240 A | 2/1997 | De Mesmaeker et al. |
| 5,610,289 A | 3/1997 | Cook et al. |
| 5,612,211 A | 3/1997 | Wilson et al. |
| 5,608,046 A | 4/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,625,126 A | 4/1997 | Lonberg et al. |
| 5,631,219 A | 5/1997 | Rosenthal et al. |
| 5,633,360 A | 5/1997 | Bischofberger et al. |
| 5,633,425 A | 5/1997 | Lonberg et al. |
| 5,652,355 A | 7/1997 | Metelev et al. |
| 5,652,356 A | 7/1997 | Agrawal |
| 5,654,186 A | 8/1997 | Cerami et al. |
| 5,661,016 A | 8/1997 | Lonberg et al. |
| 5,663,312 A | 9/1997 | Chaturvedula |
| 5,674,750 A | 10/1997 | Kraus et al. |
| 5,677,437 A | 10/1997 | Teng et al. |
| 5,677,439 A | 10/1997 | Weis et al. |
| 5,700,922 A | 12/1997 | Cook |
| 5,712,154 A | 1/1998 | Mullon et al. |
| 5,714,331 A | 2/1998 | Buchardt et al. |
| 5,716,411 A | 2/1998 | Orgill et al. |
| 5,716,616 A | 2/1998 | Prockop et al. |
| 5,719,262 A | 2/1998 | Buchardt et al. |
| 5,733,541 A | 3/1998 | Taichman et al. |
| 5,736,396 A | 4/1998 | Bruder et al. |
| 5,741,899 A | 4/1998 | Capon et al. |
| 5,770,378 A | 6/1998 | Hwang et al. |
| 5,770,580 A | 6/1998 | Ledley et al. |
| 5,776,699 A | 7/1998 | Klein et al. |
| 5,789,245 A | 8/1998 | Dubensky, Jr. et al. |
| 5,789,543 A | 8/1998 | Ingham et al. |
| 5,792,751 A | 8/1998 | Ledley et al. |
| 5,814,482 A | 9/1998 | Dubensky, Jr. et al. |
| 5,830,760 A | 11/1998 | Tsai et al. |
| 5,837,544 A | 11/1998 | Capon et al. |
| 5,843,723 A | 12/1998 | Dubensky, Jr. et al. |
| 5,844,079 A | 12/1998 | Ingham et al. |
| 5,851,832 A | 12/1998 | Weiss et al. |
| 5,851,984 A | 12/1998 | Matthews et al. |
| 5,877,207 A | 3/1999 | Klein et al. |
| 5,945,309 A | 8/1999 | Ni et al. |
| 5,945,337 A | 8/1999 | Brown |
| 5,952,345 A | 9/1999 | Klein et al. |
| 5,958,954 A | 9/1999 | Klein et al. |
| 5,990,329 A | 11/1999 | Klaus et al. |
| 6,008,204 A | 12/1999 | Klein et al. |
| 6,015,686 A | 1/2000 | Dubensky, Jr. et al. |
| 6,015,694 A | 1/2000 | Dubensky, Jr. et al. |
| 6,063,797 A | 5/2000 | Fesus et al. |
| 6,077,947 A | 6/2000 | Capon et al. |
| 6,090,810 A | 7/2000 | Klein et al. |
| 6,117,850 A | 9/2000 | Patchen et al. |
| 6,130,230 A | 10/2000 | Chambon et al. |
| 6,133,309 A | 10/2000 | Bollag et al. |
| 6,165,747 A | 12/2000 | Ingham et al. |
| 6,218,128 B1 | 4/2001 | Klein et al. |
| 6,228,848 B1 | 5/2001 | Klein et al. |
| 6,232,291 B1 | 5/2001 | Ni et al. |
| 6,248,587 B1 | 6/2001 | Rodgers et al. |
| 6,255,112 B1 | 7/2001 | Thiede et al. |
| 6,261,786 B1 | 7/2001 | Marigo et al. |
| 6,270,964 B1 | 8/2001 | Michnick et al. |
| 6,271,363 B1 | 8/2001 | Ingham et al. |
| 6,284,540 B1 | 9/2001 | Milbrandt et al. |
| 6,294,330 B1 | 9/2001 | Michnick et al. |
| 6,303,374 B1 | 10/2001 | Zhang et al. |
| 6,306,575 B1 | 10/2001 | Thomas et al. |
| 6,326,174 B1 | 12/2001 | Joyce et al. |
| 6,326,198 B1 | 12/2001 | Emerson et al. |
| 6,329,169 B1 | 12/2001 | Ni et al. |
| 6,335,195 B1 | 1/2002 | Rodgers et al. |
| 6,338,942 B2 | 1/2002 | Kraus et al. |
| 6,342,219 B1 | 1/2002 | Thorpe et al. |
| 6,342,221 B1 | 1/2002 | Thorpe et al. |
| 6,342,372 B1 | 1/2002 | Dubensky, Jr. et al. |
| 6,342,581 B1 | 1/2002 | Rosen et al. |
| 6,372,210 B2 | 4/2002 | Brown |
| 6,372,473 B1 | 4/2002 | Moore et al. |
| 6,376,236 B1 | 4/2002 | Dubensky, Jr. et al. |
| 6,384,192 B1 | 5/2002 | Ingham et al. |
| 6,413,772 B1 | 7/2002 | Block |
| 6,413,773 B1 | 7/2002 | Ptasznik et al. |
| 6,642,019 B1 | 11/2003 | Anderson et al. |
| 6,645,489 B2 | 11/2003 | Pykett et al. |
| 6,680,166 B1 | 1/2004 | Mullon et al. |
| 6,887,704 B2 | 5/2005 | Peled et al. |
| 6,962,698 B1 | 11/2005 | Peled et al. |
| 7,169,605 B2 | 1/2007 | Peled et al. |
| 7,247,477 B2 | 7/2007 | Itskovitz-Eldor et al. |
| 7,344,881 B2 | 3/2008 | Peled et al. |
| 7,955,852 B2 | 6/2011 | Peled et al. |
| 8,080,417 B2 | 12/2011 | Peled et al. |
| 8,652,841 B2 | 2/2014 | Ochiai et al. |
| 2001/0014475 A1 | 8/2001 | Frondoza et al. |
| 2002/0001826 A1 | 1/2002 | Wager et al. |

(56) References Cited

U.S. PATENT DOCUMENTS

| | | |
|---|---|---|
| 2002/0090603 A1 | 7/2002 | Lipton et al. |
| 2002/0114784 A1 | 8/2002 | Li et al. |
| 2002/0114789 A1 | 8/2002 | Peled et al. |
| 2002/0146678 A1 | 10/2002 | Benvenisty |
| 2002/0146816 A1 | 10/2002 | Vellinger et al. |
| 2002/0159981 A1 | 10/2002 | Peled et al. |
| 2002/0159984 A1 | 10/2002 | Brown |
| 2002/0182728 A1 | 12/2002 | Ramiya et al. |
| 2003/0002363 A1 | 1/2003 | Le et al. |
| 2003/0031665 A1 | 2/2003 | Dang et al. |
| 2003/0113913 A1 | 6/2003 | Purton |
| 2003/0125410 A1 | 7/2003 | Keita et al. |
| 2003/0149074 A1 | 8/2003 | Melese et al. |
| 2003/0215445 A1 | 11/2003 | Serrero |
| 2003/0235909 A1 | 12/2003 | Hariri et al. |
| 2004/0076603 A1 | 4/2004 | Peled et al. |
| 2004/0247574 A1 | 12/2004 | Christopherson, II et al. |
| 2005/0008624 A1 | 1/2005 | Peled et al. |
| 2005/0031595 A1 | 2/2005 | Peled et al. |
| 2005/0054097 A1 | 3/2005 | Peled et al. |
| 2005/0054103 A1 | 3/2005 | Peled et al. |
| 2005/0069527 A1 | 3/2005 | Laughlin et al. |
| 2005/0084961 A1 | 4/2005 | Hedrick et al. |
| 2005/0095228 A1 | 5/2005 | Fraser et al. |
| 2005/0118150 A1 | 6/2005 | Peled et al. |
| 2005/0214262 A1 | 9/2005 | Peled et al. |
| 2005/0220774 A1 | 10/2005 | Peled et al. |
| 2005/0260748 A1 | 11/2005 | Chang et al. |
| 2006/0093605 A1 | 5/2006 | Campana et al. |
| 2006/0171932 A1 | 8/2006 | Hendricks et al. |
| 2006/0205071 A1 | 9/2006 | Hasson et al. |
| 2007/0077652 A1 | 4/2007 | Peled et al. |
| 2008/0279828 A1 | 11/2008 | Peled et al. |
| 2010/0015103 A1 | 1/2010 | Liu et al. |
| 2010/0061963 A1 | 3/2010 | Peled |
| 2010/0183564 A1 | 7/2010 | Boitano et al. |
| 2012/0028354 A1 | 2/2012 | Lee et al. |
| 2014/0023623 A1 | 1/2014 | Peled et al. |
| 2014/0023626 A1 | 1/2014 | Peled et al. |
| 2015/0064273 A1 | 3/2015 | Peled et al. |

FOREIGN PATENT DOCUMENTS

| | | |
|---|---|---|
| EP | 0331464 | 9/1989 |
| EP | 1332673 | 8/2003 |
| EP | 1332676 | 8/2003 |
| EP | 1424389 | 6/2004 |
| JP | 2005-528088 | 8/2005 |
| KR | 20090065814 A | 6/2009 |
| WO | WO 89/02468 | 4/1989 |
| WO | WO 89/05345 | 6/1989 |
| WO | WO 89/07136 | 8/1989 |
| WO | WO 92/07573 | 5/1992 |
| WO | WO 92/11355 | 7/1992 |
| WO | WO 93/09220 | 5/1993 |
| WO | WO 93/18132 | 9/1993 |
| WO | WO 94/18991 | 9/1994 |
| WO | WO 95/14078 | 5/1995 |
| WO | WO 95/21911 | 8/1995 |
| WO | WO 95/24464 | 9/1995 |
| WO | WO 96/01108 | 1/1996 |
| WO | WO 96/40876 | 12/1996 |
| WO | WO 97/04707 | 2/1997 |
| WO | WO 97/31647 | 9/1997 |
| WO | WO 97/33978 | 9/1997 |
| WO | WO 97/41209 | 11/1997 |
| WO | WO 97/41224 | 11/1997 |
| WO | WO 98/25634 | 6/1998 |
| WO | WO 99/07831 | 2/1999 |
| WO | WO 99/18885 | 4/1999 |
| WO | WO 99/40783 | 8/1999 |
| WO | WO 99/64566 | 12/1999 |
| WO | WO 00/18885 | 4/2000 |
| WO | WO 00/030635 | 6/2000 |
| WO | WO 00/46349 | 8/2000 |
| WO | WO 00/66712 | 11/2000 |
| WO | WO 00/73421 | 12/2000 |
| WO | WO 02/064755 | 8/2002 |
| WO | WO 02/080995 | 10/2002 |
| WO | WO 02/102299 | 12/2002 |
| WO | WO 03/004626 | 1/2003 |
| WO | WO 03/051419 | 6/2003 |
| WO | WO 03/062369 | 7/2003 |
| WO | WO 03/062404 | 7/2003 |
| WO | WO 03/072557 | 9/2003 |
| WO | WO 03/078567 | 9/2003 |
| WO | WO 04/016731 | 2/2004 |
| WO | WO 2004/078917 | 9/2004 |
| WO | WO 2005/007073 | 1/2005 |
| WO | WO 2005/007799 | 1/2005 |
| WO | WO 2005/086845 | 9/2005 |
| WO | WO 2006/030442 A2 | 3/2006 |
| WO | WO 2006/050270 | 5/2006 |
| WO | WO 2007/063545 | 6/2007 |
| WO | WO 2008/020815 A1 | 2/2008 |
| WO | WO 2008/056368 | 5/2008 |
| WO | WO 2011/080740 | 7/2011 |
| WO | WO-11139357 A1 | 11/2011 |
| WO | WO 2013/121426 | 8/2013 |
| WO | WO 2013/121427 | 8/2013 |

OTHER PUBLICATIONS

Search Report and Written Opinion dated Apr. 8, 2015 From the Intellectual Property Office of Singapore Re. Application No. 11201404608W.

Da Silva Meirelles et al. "Mechanisms Involved in the Therapeutic Properties of Mesenchymal Stem Cells", Cytokine & Growth Factor Reviews, 20: 419-427, 2009.

Daan van Poll et al. "Mesenchymal Stem Cell-Derived Molecules Directly Modulate Hepatocellular Death and Regeneration In Vitro and In Vivo", Hepatology, Vo. 47, No. 5, 2008.

Boland et al. "Wnt 3a Promotes Proliferation and Suppresses Osteogenic Differentiation of Adult Human Mesenchymal Stem Cells", Journal of Cellular Biochemistry, 93: 1210-1230, 2004.

Bonewald et al. "Role of Active and Latent Transforming Growth Factor Beta in Bone Formation", Journal of Cellular Biochemistry, 55: 350-357, 1994.

Cargnoni et al. "Conditioned Medium From Amniotic Mesenchymal Tissue Cells Reduces Progression of Bleomycin-Induced Lung Fibrosis", Cytotherapy, 14: 153-161, 2012.

Colleoni et al. "Isolation, Growth and Differentiation of Equine Mesenchymal Stem Cells: Effect of Donor, Source, Amount of Tissue and Supplementation With Basi Fibroblast Growth Factor", Veterinary Research Communications, 33(8): 811-821, Dec. 2009.

Furge et al. "Met Receptor Tyrosine Kinase: Enhanced Signaling Through Adapter Proteins", Oncogene, 19: 5582-5589, 2000.

Gnecchi et al. "Bone Marrow-Derived Mesenchymal Stem Cells: Isolation, Expansion, Characterization, Viral Transduction, and Production of Conditioned Medium", Stem Cells in Regenerative Medicine: Methods and Protocols, 482(Chap.18): 281-294, 2009.

Kassis et al. "Isolation of Mesenchymal Stem Cells From G-CSF-Mobilized Human Peripheral Blood Using Fibrin Microbeads", Bone Marrow Transplantation, 37(10): 967-976, May 2006.

Krampera et al. "HB-EGF/HER-1 Signaling in Bone Marrow Mesenchymal Stem Cells: Inducing Cell Expansion and Reversibly Preventing Multilineage Differentiation", Blood, 106(1): 59-66, Jul. 1, 2005.

Lin et al. "The Isolation of Novel Mesenchymal Stromal Cell Chemotactic Factors From the Conditioned Medium of Tumor Cells", Experimental Cell Research, 314: 3107-3117, Available Online Aug. 8, 2008.

Longobardi et al. "Effect of IGF-I in the Chondrogenesis of Bone Marrow Mesenchymal Stem Cells in the Presence of Absence of TGF-Beta Signaling", Journal of Bone and Mineral Research, 21(4): 626-636, Published Online Dec. 26, 2005.

Pons et al. "VEGF Improves Survival of Mesenchymal Stem Cells in Infarcted Hearts", Biochemical and Biophysical Research Communications, 376: 419-422, Available Online Sep. 18, 2008.

(56) References Cited

OTHER PUBLICATIONS

Stewart et al. "BMP-3 Promotes Mesenchymal Stem Cell Proliferation Through the TGF-Beta/Activin Signaling Pathway", Journal of Cellular Physiology, 223: 658-666, Feb. 8, 2010.
Tamama et al. "Epidermal Growth Factor (EGF) Treatment on Multipotential Stromal Cells (MSCs). Possible Enhancement of Therapeutic Potential of MSC", Journal of Biomedicine and Biotechnology, 2010(795385): 1-10, 2010.
Tamama et al. "Epidermal Growth Factor as a Candidate for Ex Vivo Expansion of Bone Marrow-Derived Mesenchymal Stem Cells", Stem Cells, 24: 686-695, First Published Sep. 8, 2005.
Van Koppen et al. "Human Embryonic Mesenchymal Stem Cell-Derived Conditioned Medium Rescues Kidney Function in Rats With Established Chronic Kidney Disease", PLoS One, 7(6): e38746-1-e38746-12, Jun. 19, 2012.
Wagner et al. "Replicative Senescence of Mesenchymal Stem Cells: A Continuous and Organized Process", PLoS One, 3(5): e2213-1-e2213-12, May 21, 2008.
Wang et al. "Clinical Applications of Mesenchymal Stem Cells", Journal of Hematology & Oncology, 5(19): 1-9, 2012.
Wang et al. "Mesenchymal Stem Cell-Conditioned Medium Facilitates Angiogenesis and Fracture Healing in Diabetic Rats", Journal of Tissue Engineering and Regenerative Medicine, 6: 559-569, Published Online Sep. 13, 2011.
Yew et al. "Enhancement of Wound Healing by Human Multipotent Stromal Cell Conditioned Medium: The Paracrine Factors and P38 MAPK Activation", Cell Transplantation, 20: 693-706, Published Online Dec. 22, 2010.
Zhang et al. "Comparison of Mesenchymal Stem Cells From Human Placenta and Bone Marrow", Chinese Medical Journal, 117(6): 882-887, 2004.
Samsonraj, Rebekah M., et al., Establishing Criteria for Human Mesenchymal Stem Cell Potency, Stem Cells 2015, 33:1878-1891.
Acsadi et al. "Human Dystrophin Expression in MDX Mice After Intramuscular Injection of DNA Constructs", Nature, 352(6338): 815-818, 1991.
Aiuti et al. "The Chemokine SDF-1 Is a Chemoattractant for Human CD34+ Hematopoietic Progenitor Cells and Provides a New Mechanism to Explain the Mobilization of CD34+ Progenitors to Peripheral Blood", Journal of Experimental Medicine, 185(1): 111-120, 1997.
Alici et al. "Autologous Antitumor Activity by NK Cells Expanded From Myeloma Patients Using GMP-Compliant Components", Blood, XP003027014, 111(6): 3155-3162, Mar. 15, 2008.
Alter "Fetal Erythropoiesis in Stress Hematopoiesis", Experimental Hematology 7(Suppl 5): 200-209, 1979. Abstract.
American Cancer Society "Chelation Therapy", American Cancer Society, ACS, p. 1-5, 2006.
Anderlini et al. "The Use of Mobilized Peripheral Blood Stem Cells From Normal Donors for Allografting", Stem Cells, 15: 9-17, 1997.
Aoki et al. "In Vivo Transfer Efficiency of Antisense Oligonucleotides Into the Myocardium Using HVJ-Liposome Method", Biochemical and Biophysical Research Communications, 231: 540-545, 1997.
Armentano et al. "Expression of Human Factor IX in Rabbit Hepatocytes by Retrovirus-Mediated Gene Transfer: Potential for Gene Therapy of Hemophilia B", Proc. Natl. Acad. Sci. USA, 87: 6141-6145, 1990.
Arriero et al. "Adult Skeletal Muscle Stem Cells Differentiate Into Endothelial Lineage and Ameliorate Renal Dysfunction After Acute Ischemia", American Journal of Physiology—Renal Physiology, 287: F621-F627, 2004.
Asahara et al. "Stem Cell Therapy and Gene Transfer for Regeneration", Gene Therapy, 7: 451-457, 2000.
Auger et al. "PDGF-Dependent Tyrosine Phosphorylation Stimulates Production of Novel Polyphosphoinositides in Intact Cells", Cell, 57: 167-175, 1989.
Avital et al. "Isolation, Characterization, and Transplantation of Bone Marrow-Derived Hepatocyte Stem Cells", Biochemical and Biophysical Research Communications, 288(1): 156-164, 2001.

Bachanova et al. "Allogeneic Natural Killer Cells for Refractory Lymphoma", Cancer Immunology and Immunotherapy, 59: 1739-1744, Aug. 3, 2010.
Bae et al. "Copper Uptake and Intracellular Distribution During Retinoic Acid-Induced Differentiation of HL-60 Cells", Journal of Nutritional Biochemistry, Food Science and Human Nutrition Department, 5: 457-461, 1994.
Bae et al. "Retinoic Acid-Induced HL-60 Cell Differentiation Is Augmented by Copper Supplementation", The Journal of Nutrition, 123(6): 997-1002, 1993.
Baggiolini "Chemokines and Leukocyte Traffic", Nature, 392: 565-568, 1998.
Banasik et al. "Specific Inhibitors of Poly(ADP-Ribose) Synthetase and Mono(ADP-Ribosyl)Transferase", The Journal of Biological Chemistry, 267(3): 1569-1575, 1992.
Banno et al. "Anemia and Neutropenia in Elderly Patients Caused by Copper Deficiency for Long-Term Eternal Nutrition", Rinsho-Ketsueki, 35(11): 1276-1280, Nov. 1994. Abstract.
Baum et al. "Isolation of a Candidate Human Hematopoietic Stem-Cell Population", Proc. Natl. Acad. Sci. USA, 89: 2804-2808, 1992.
Beider et al. "Involvement of CXCR4 and IL-2 in the Homing and Retention of Human NK and NK T Cells to the Bone Marrow and Spleen of NOD/SCID Mice", Blood, 102(6): 1951-1958, Sep. 15, 2003.
Belovari et al. "Differentiation of Rat Neural Tissue in a Serum-Free Embryo Culture Model Followed by in Vivo Transplantation", Croatian Medical Journal, 42(6): 611-617, 2001. Abstract.
Berardi et al. "Individual CD34+CD38lowCD19-CD10- Progenitor Cells From Human Cord Blood Generate B Lymphocytes and Granulocytes", Blood, 89(10): 3554-3564, May 1997. Abstract.
Berg et al. "Clinical-Grade Ex Vivo-Expanded Human Natural Killer Cells Up-Regulate Activating Receptors and Death Receptor Ligands and Have Enhanced Cytolytic Activity Against Tumor Cells", Cytotherapy, 11(3): 341-355, 2009.
Berkner "Development of Adenovirus Vectors for the Expression of Heterologous Genes", BioTechniques, 6(7): 616-629, 1988.
Bernardini et al. "CCL3 and CXCL12 Regulate Trafficking of Mouse Bone Marrow NK Cell Subsets", Blood, 111(7): 3626-3634, Apr. 1, 2008.
Bernhard et al. Generation of Immunostimulatory Dendritic Cells From Human CD34+ Hematopoietic Progenitor Cells of the Bone Maroow and Peripheral Blood, Cancer Research, 55: 1099-1104, 1995.
Bertagnolo et al. "Phosphoinositide 3-Kinase Activity Is Essential for All-Trans-Retinoic Acid-Induced Granulocytic Differentiation of HL-60 Cells[1]", Cancer Research, 59: 542-546, 1999.
Bhatia et al. "Purification of Primitive Human Hematopoietic Cells Capable of Repopulating Immune-Deficient Mice", Proc. Natl. Acad. Sci. USA, 94: 5320-5325, 1997.
Bhat-Nakshatri et al. "Tumour Necrosis Factor and PI3-Kinase Control Oestrogen Receptor Alpha Protein Level and Its Transrepression Function", Cancer, 90: 853-859, 2004.
Bi et al. "Effect of Lactoferrin on Proliferation and Differentiation of the Jurkat Human Lymphoblastic T Cell Line", Archivum Immunologiae et Therapiae Experimentalis, 45(4): 315-320, 1997. Abstract.
Bieback et al. "Critical Parameters for the Isolation of Mesenchymal Stem Cell From Umbilical Cord Blood", Stem Cells, 22: 625-634, 2004.
Bird et al. "Single-Chain Antigen-Binding Proteins", Science, 242: 423-426, 1988.
Birkenkamp et al. "An Inhibitor of PI3-K Differentially Affects Proliferation and IL-6 Protein Secretion in Normal and Leukemic Myeloid Cells Depending on the Stage of Differentiation", Experimental Hematology, 28(11): 1239-1249, 2000. Abstract.
Blau et al. "Fetal Hemoglobin in Acute and Chronic Stage of Erythroid Expansion", Blood, 81(1): 227-233, 1993.
Blyszczuk et al. "Embryonic Stem Cells Differentiate Into Insulin-Producing Cells Without Selection of Nestin-Expressing Cells", International Journal of Developmental Biology, 48: 1095-1104, 2004.

(56) References Cited

OTHER PUBLICATIONS

Boemer et al. "Production of Antigen-Specific Human Monoclonal Antibodies From In Vitro-Primed Human Splenocytes", The Journal of Immunology, 147(1): 86-95, 1991.
Bohmer et al. "Fetal Cell Isolation From Maternal Blood Cultures by Flow Cytometric Hemoglobin Profiles", Fetal Diagnosis and Therapy, 17(2): 83-89, 2002.
Boitano et al. "Aryl Hydrocarbon Receptor Antagonists Promote the Expansion of Human Hematopoietic Stem Cells", Science, 329(5997): 1345-1348, Sep. 10, 2010.
Bongers et al. "Kinetics of Dipeptyl Peptidase IV Proteolysis of Growth Hormone-Releasing Factor and Analogs", Biochimica et Biophysica Acta, 1122: 147-153, 1992.
Borthwick et al. "A Comparison of Cupruretic Responses to Various Tetramines and D-Penicillamine", Journal of Laboratory and Clinical Medicine, 95(4): 575-580,1980.
Brandt et al. "Ex Vivo Expansion of Autologous Bone Marrow CD34+ Cells With Porcine Microvascular Endothelial Cells Results in a Graft Capable of Rescuing Lethally Irradiated Baboons", Blood, 94(1): 106-113, 1999.
Brazelton et al. "From Marrow to Brain: Expression of Neuronal Phenotypes in Adult Mice", Science, 290(5497): 1775-1779, Dec. 1, 2000.
Breitman et al. "Induction of Differentiation of the Human Promyelocytic Leukemia Cell Line (HL-60) by Retinoic Acid", Proc. Natl. Acad. Sci., 77(5): 2936-2940, 1980.
Briddell et al. "Purification of CD34+ Cells Is Essential for Optimal Ex Vivo Expansion of Umbilical Cord Blood Cells", Journal of Hematotherapy, 6: 145-150, 1997.
Brigham et al. "Rapid Communication: In Vivo Transfection of Murine Lungs With a Functioning Prokaryotic Gene Using a Liposome Vehicle", The American Journal of the Medical Sciences, 298(4): 278-281, 1989.
Brott et al. "Flow Cytometric Characterization of Perfused Human Bone Marrow Cultures: Identification of the Major Cell Lineages and Correlation With the CFU-GM Assay", Cytometry Part A, 53A: 22-27, 2003.
Broxmeyer "Regulation of Hematopoiesis by Chemokine Family Members", International Journal of Hematology, 74: 9-17, 2001.
Brugger et al. "Ex Vivo Expansion of Enriched Peripheral Blood CD34+ Progenitor Cells by Stem Cell Factor, Interleukin-1? (IL-1?), IL-6, IL-3, Interferon, and Erythropoietin", Blood, 81(10); 2579-2584, 1993.
Brugger et al. "Reconstitution of Hematopoiesis After High-Dose Chemotherapy by Autologous Progenitor Cells Generated Ex Vivo", New England Journal of Medicine, 333(5): 283-287, 1995.
Brugnera et al. "Cloning, Chromosomal Mapping and Characterization of the Human Metal-Regulatory Transcription Factor MTF-1", Nucleic Acids Research, 22(15): 3167-3173, 1994.
Bryder et al. "Hematopoietic Stem Cells. The Paradigmatic Tissue-Specific Stem Cell", American Journal of Patology, 169(2): 338-346, 2006.
Burgada et al. "Synthesis of New Phosphonated Tripod Ligands as Putative New Therapeutic Agents in the Chelation Treatment of Metal Intoxications", European Journal of Organic Chemistry, p. 349-352, 2001.
Buskin et al. "Identification of a Myocyte Nuclear Factor That Binds to the Muscle-Specific Enhancer of the Mouse Muscle Creatine Kinase Gene", Molecular and Cellular Biology, 9(6): 2627-2640, 1989.
Butt "Introduction to Chemical Reactor Theory", Reaction Kinetics and Reactor Design, Chap. 4: 184-241, 1980.
Cable et al. "Exposure of Primary Rat Hepatocytes in Long-Term DMSO Culture to Selected Transition Metals Induces Hepatocyte Proliferation and Formation of Duct-Like Structure", Hepatoloty, 26(6): 1444-1457, 1997.
Cakir-Kiefer et al. "Kinetic Competence of the cADP-Ribose-CD38 Complex as an Intermediate in the CD38/NAD+ Glycohydrolase-Catalysed Reactions: Implication for CD38 Signalling", Biochemical Journal, 358: 399-406, 2001.

Caliaro et al. "Response of Four Human Ovarian Carcinoma Cell Lines to All-Trans Retinoic Acid: Relationship With Induction of Differentiation and Retinoic Acid Receptor Expression", International Journal of Cancer, 56(5): 743-748, Mar. 1, 1994. Abstract.
Caligiuri "Human Natural Killer Cells", Blood, 112(3): 461-469, Aug. 1, 2008.
Casal et al. "In Utero Transplantation of Fetal Liver Cells in the Mucopolysaccharidosis Type VII Mouse Results in Low-Level Chimerism, But Overexpression of Beta-Glucuronidase Can Delay Onset of Clinical Signs", Blood, 97(6): 1625-1634, 2001.
Cepko "Overview of the Retrovirus Transduction System", Short Protocols in Molecular Biology, Unit 9.10-9.14: 9-41-9-57, 1984.
Charrier et al. "Normal Human Bone Marrow CD34+CD133+ Cells Contain Primitive Cells Able to Produce Different Categories of Colony-Forming Unit Megacaryocytes In Vitro", Experimental Hematology, 30: 1051-1060, 2002.
ChemMasters "Duraguard 100", Safety Data Sheet, p. 1-4, 1999.
Chen et al. "Differentiation of Rat Marrow Mesenchymal Stem Cells Into Pancreatic Islet Beta-Cells", World Journal of Gastroenterology, 10(20): 3016-3020, 2004.
Chen et al. "Fibroblast Growth Factor (FGF) Signaling Through PI 3-Kinase and Akt/PKB Is Required for Embryoid Body Differentiation", Oncogene, 19: 3750-3756, 2000.
Chen et al. "Therapeutic Benefit of Intravenous Administration of Bone Marrow Stromal Cells After Cerebral Ischemia in Rats", Stroke, 32(4): 1005-1011, 2001.
Chisi et al. "Inhibitory Action of the Peptide AcSDKP on the Proliferative State of Hematopoietic Stem Cells in the Presence of Captopril But Not Lisinopril", Stem Cells, 15(6): 455-460, 1997.
Chivu et al. "In Vitro Hepatic Differentiation of Human Bone Marrow Mesenchymal Stem Cells Under Differential Exposure to Liver-Specific Factors", Translational Research, 154(3): 122-132, Sep. 2009. Abstract.
Cho et al. "Expansion and Activation of Natural Killer Cells for Cancer Immunotherapy", Korean Journal of Laboratory Medicine, 29(2): 89-96, Apr. 2009.
Chowdhury et al. "Long-Term Improvement of Hypercholesterolemia After Ex Vivo Gene Therapy in LDLR-Deficient Rabbits", Science, 254: 1802-1805, 1991.
Christopherson II et al. "Cell Surface Peptidase CD26/Dipeptidylpeptidase IV Regulates CXCL12/Stromal Cell-Derived Factor-1?-Mediated Chemotaxis of Human Cord Blood CD34+ Progenitor Cells", The Journal of Immunology, 169: 7000-7008, 2002.
Christopherson II et al. "Modulation of Hematopoietic Stem Cell Homing and Engraftment by CD26", Science, 305: 1000-1003, 2004.
Cicuttini et al. "Support of Human Cord Blood Progenitor Cells on Human Stromal Cell Lines Transformed by SV40 Large T Antigen Under the Influence of an Inducible (Metallothionein) Promoter", Blood, 80(1): 102-112, 1992.
Cole et al. "The EBV-Hybridoma Technique and Its Application to Human Lung Cancer", Monoclonal Antibodies and Cancer Therapy, p. 77-96, 1985.
Collins et al. "Stirred Culture of Peripheral and Cord Blood Hematopoietic Cells Offers Advantages Over Traditional Static Systems for Clinically Relevant Aoolications", Biotechnology and Bioengineering, 59(5): 534-543, 1998.
Colter et al. "CD34+ Progenitor Cell Selection: Clinical Transplantation, Tumor Cell Purging, Gene Therapy, Ex Vivo Expansion, and Cord Blood Processing", Journal of Hematology, 5: 179-184, 1996.
Corda et al. "Functional Aspects of Protein Mono-ADP-Ribosylation", The EMBO Journal, 22(9): 1953-1958, 2003.
Cote et al. "Response to Histone Deacetylase Inhibition of Novel PML/RAR? Mutants Detected in Retinoic acid-Resistant APL cells", Blood, 100(7): 2586-2596, 2002. Abstract.
Coutinho et al. "Effects of Recombinant Human Granulocyte Colony-Stimulating Factor (CSF), Human Granulocyte Macrophage-CSF, and Gibbon Interleukin-3 on Hematopoiesis in Human Long-Term Bone Marrow Culture", Blood, 75(11): 2118-2129, 1990.

(56) References Cited

OTHER PUBLICATIONS

Cristiano et al. "Hepatic Gene Therapy: Adenovirus Enhancement of Receptor-Mediated Gene Delivery and Expression in Primary Hepatocytes", Proc. Natl. Acad. Sci. USA, 90: 2122-2126, 1993.
Curiel et al. "Adenovirus Enhancement of Transferrin-Polylysine-Mediated Gene Delivery", Proc. Natl. Acad. Sci. USA, 88: 8850-8854, 1991.
Czauderna et al. "Functional Studies of the PI(3)-Kinase Signalling Pathway Employing Synthetic and Expressed siRNA", Nuc. Acid. Res., 31(2): 670-682, 2003.
Czyz et al. "Potential of Embryonic and Adult Stem Cell in Vitro", Biological Chemistry, 384: 1391-1409, 2003.
Dabeva et al. "Transcription Factor and Liver-Specific mRNA Expression in Facultative Epithelial Progenitor Cells of Liver and Pancreas", American Journal of Pathology,147(6): 1633-1648, Dec. 1995.
Dahl et al. "Tranformation of Hematopoietic Cells by the Ski Oncoprotein Involves Repression of Retinoic Acid Receptor Signaling", Proc. Natl, Acad. Sci. USA, 95(19): 11187-11192, Sep. 1998.
Dai et al. "Gene Therapy Via Primary Myoblasts: Long-Term Expression of Factor IX Protein Following Transplantation In Vivo", Proc. Natl. Acad. Sci. USA, 89: 10892-10895, Nov. 1992.
Dalyot et al. "Adult and Neonatal Patterns of Human Globin Gene Expression Are Recapitulated in Liquid Cultures", Experimental Hematology, 20(9): 1141-1145, Oct. 1992. Abstract.
Danos et al. "Safe and Efficient Generation of Recombinant Retroviruses With Amphotropic and Ecotropic Host Ranges", Proc. Natl. Acad. Sci. USA, 85: 6460-6464, 1988.
Datta et al. "Ionizing Radiation Activates Transcription of the EGR1 Gene Via CArG Elements", Proc. Natl. Acad. Sci. USA, 89: 10149-10153, 1992.
De Bruyn et al. "Comparison of the Coexpressioin of CD33 and HLA-DR Antigens on CD34+ Purified Cells From Human Cord Blood and Bone Narrow", Stem Cells, 13: 281-288, 1995.
De La Cruz et al. "Do Protein Motifs Read the Histone Code?", BioEssays, 27.2: 164-175, 2005.
De Luca et al. "Retinoic Acid Is a Potent Regulator of Growth Plate Chondrogenesis", Endocrinology, 141(1): 346-353, Jan. 2000. Abstract.
De Ridder et al. "Hypoxic Tumor Cell Radiosensitization: Role of the iNOS/NO Pathway", Bulletin du Cancer, XP009146914, 95(3): 282-291, Mar. 2008.
De Wynter et al. "CD34+AC133+ Cells Isolated From Cord Blood Are Highly Enriched in Long-Term Culture-Initiating Cells, NOD/SCID-Repopulating Cells and Dendritic Cell Progenitors", Stem Cells, 16: 387-396, 1998.
Decot et al. "Natural-Killer Cell Amplification for Adoptive Leukemia Relapse Immunotherapy: Comparison of Three Cytokines, IL-2, IL-15, or IL-7 and Impact on NKG2D, K1R2DL1, and KIR2DL2 Expression", Experimental Hematology, 38(5): 351-362, May 2010.
Defacque et al. "Expression of Retinoid X Receptor Alpha Is Increased Upon Monocytic Cell Differentiation", Biochemical and Biophysical Research Communications, 220: 315-322, 1996.
Dexter et al. "Conditions Controlling the Proliferation of Haemopoietic Stem Cells In Vitro", Journal of Cell Physiology, 91: 335-344, 1976.
Donovan et al. "The End of the Beginning for Pluripotent Stem Cells", Nature, 414(6859): 92-97, 2001.
Dosil et al. "Mitogenic Signalling and Substrate Specificity of the Flk2/Flt3 Receptor Tyrosine Kinase in Fibroblasts and Interleuk in 3-Dependent Hematopoietic Cells", Molecular Biology, 13(10): 6572-6585, 1993. Abstract.
Douer et al. "All-Trans-Retinoic Acid Effects the Growth, Differentiation and Apoptosis of Normal Human Myeloid Progenitors Derived From Purified CD34+ Bone Marrow Cells", Leukemia, 14(5): 874-881, 2000.
Drayson et al. "Cell Proliferation and CD11b Expression Are Controlled Independently During HL60 Cell Differentiation Initiated by 1,25?-Dihydroxyvitamin D3 or All-Trans-Retinoic Acid", Experimental Cell Research, 266(1): 126-134, 2001, Abstract.
Dubois et al. "Treatment of Wilson's Disease With Triethylene Tetramine Hydrochloride (Trientine)", Journal of Pediatric Gastroenterology and Nutrition, 10(1): 77-81, 1990. Abstract.
Duncan et al. "Repair of Myelin Disease: Strategies and Progress in Animal Models", Molecular Medicine Today, 3(12): 554-561, 1997, Abstract.
Ebner et al. "Distinct Roles for PI3K in Proliferation and Survival of Oligodendrocyte Progenitor Cells", Journal of Neuroscience Research, 62: 336-345,2000.
Eglitis et al. "Gene Expression in Mice After High Efficiency Retroviral-Mediated Gene Transfer", Science, 230: 1395-1398, 1985.
Ehring et al. "Expansion of HPCs From Cord Blood in a Novel 3D Matrix", Cytotherapy, 5(6): 490-499, 2003.
Eipers et al. "Retroviral-Mediated Gene Transfer in Human Bone Marrow Cells Grown in Continuous Perfusion Culture Vessels", Blood, 86(10): 3754-3762, 1995.
Emerson "Ex Vivo Expansion of Hematopoietic Precursors, Progenitors, and Stem Cells: The Next Generation of Cellular Therapeutics", Blood, 87(8): 3082-3088, 1996.
Englisch et al. "Chemically Modified Oligonucleotides as Probes and Inhibitors", Angewandte Chemie (International Edition in English), 30(6): 613-629, 1991.
Farre et al. "FGF-4 Increases In Vitro Expansion Rate of Human Adult Bone Marrow-Derived Mesenchymal Stem Cells", Growth Factors, 25(2): 71-76, Apr. 2007.
Fasouliotis et al. "Human Umbilical Cord Blood Banking and Transplantation: A State of the Art", European Journal of Obstetrics & Gynecology and Reproductive Biology, 90(1): 13-25, 2000.
Feldman "Israeli Start-Up Gamida-Cell to Receive Prize", Globes—Online, 2004.
Ferbeyre "PML A Target of Translocations in APL Is a Regulator of Cellular Senescence", Leukemia, 16: 1918-1926, 2002. Abstract.
Ferrari et al. "Muscle Regeneration by Bone Marrow-Derived Myogenic Progenitors", Science, 279(5356): 1528-1530, 1998. Erratum in: Science, 281(5379): 923, 1998.
Ferrero et al. "The Metamorphosis of a Molecule: From Soluble Enzyme to the Leukocyte Receptor CD38", Journal of Leukocyte Biology, 65(2): 151-161, 1999.
Ferry et al. "Retroviral-Mediated Gene Transfer Into Hepatocytes In Vivo", Proc. Natl. Acad. Sci. USA, 88: 8377-8381, 1991.
Fibach et al. "Growth of Human Normal Erythroid Progenitors in Liquid Culture: A Comparison With Colony Growth in Semisolid Culture", International Journal of Cell Cloning, 9: 57-64, 1991. Abstract.
Fibach et al. "Normal Differentiation of Myeloid Leukemic Cells Induced by a Protein Differentiation-Inducing Protein", Nature New Biology, 237(78): 276-278, 1972.
Fibach et al. "Proliferation and Maturation of Human Erythroid Progenitors in Liquid Culture", Blood, 73(1): 100-103, 1989.
Fibach et al. "Retinoic Acid Antagonist Inhibits CD38 Antigen Expression on Human Hematopoietic Cells", Blood, 100(11): 172A, #644 & 44th Annual Meeting of the American Society of Hematology, 2002.
Fibach et al. "The Two-Step Liquid Culture: A Novel Procedure for Studying Maturation of Human Normal and Pathological Erythroid Precursors", Stem Cells, 11(Suppl.1): 36-41, 1993. Abstract.
Fietz et al. "Culturing Human Umbilical Cord Blood: A Comparison of Mononuclear Vs CD34+ Selected Cells", Bone Marrow Transplantation, 23: 1109-1115, 1999.
Filvaroff et al. "Functional Evidence for an Extracellular Calcium Receptor Mechanism Triggering Tyrosine Kinase Activation Associated With Mouse Keratinocyte Differentiation", The Journal of Biological Chemistry, 269(34): 21735-21740, 1994.
Fisch et al. "Generation of Antigen-Presenting Cells for Soluble Protein Antigens Ex Vivo From Peripheral Blood CD34+ Hematopoietic Progenitor Cells in Cancer Patients", European Journal of immunology, 26: 595-600, 1996.
Fishwild et al. "High-Avidity Human IgG? Monoclonal Antibodies From a Novel Strain of Minilocus Transgenic Mice", Nature Biotechnology, 14: 845-851, 1996.

(56) References Cited

OTHER PUBLICATIONS

Flores et al. "Akt-Mediated Survival of Oligodendrocytes Induced by Neuregulins", The Journal of Neuroscience, 20(20): 7622-7630, 2000.
Flotte et al. "Expression of the Cystic Fibrosis Transmemebrane Conductance Regulators From a Novel Adeno-Associated Virus Promoter", The Journal of Biological Chemistry, 268(5): 3781-3790, 1993.
Flotte et al. "Gene Expression From Adeno-Associated Virus Vectors in Airways Epithelial Cells", American Journal of Respiratory Cell and Molecular Biology, 7: 349-356, 1992.
Forraz et al. "AC133+ Umbilical Cord Blood Progenitors Demonstrate Rapid Self-Renewal and Low Apoptosis", Br. Journal Haematol., 119(2): 516-524, 2002.
Fosmire "Zinc Toxicity", American Journal of Clinical Nutrition, 51(2): 225-227, 1990.
Freedman et al. "Generation of Human T Lymphocytes Front Bone Marrow CD34+ Cells In Vitro", Nature Medicine, 2(1): 46-51, 1995.
Freshney "Culture of Animal Cells, A Manual of Basic Technique", John Wiley & Sons, 3rd Ed., Chap. 20: 309-311, 327-328.
Frias et al. "Generation of Functional Natural Killer and Dendritic Cells in a Human Stromal-Based Serum-Free Culture System Designed for Cord Blood Expansion", Experimental Hematology, 36: 61-68, 2008.
Fry "Phosphoinositide 3-Kinase Signalling in Breast Cancer: How Big a Role Might It Play?", Breast Cancer Research, 3(5): 304-312, 2001.
Gagnon et al. "Activation of Protein Kinase B and Induction of Adipogenesis by Insulin in 3T3-L1 Preadipocytes", Diabetes, 48: 691-698, 1999.
Gallacher et al. "Isolation and Characterization of Human CD34-Lin- and CD34+Lin- Hematopoietic Stem Cells Using Cell Surface Markers AC133 and CD7", Blood, 95(9): 2813-2820, 2000.
Gloeckner et al. "New Miniaturized Hollow-Fiber Bioreactor for In Vivo Like Cell Culture, Cell Expansion, and Production of Cell-Derived Products", Biotechnology Progresses, 17: 828-831, 2001.
Gluckman et al. "Hematopoietic Reconstitution in a Patient With Fanconi's Anemia by Means of Umbilical-Cord Blood From an HLA-Identical Sibling", The New England Journal of Medicine, 321(17): 1174-1178, 1989.
Gossler et al. "Transgenesis by Means of Blasocyst-Derived Embryonic Stem Cell Lines", Proc. Natl. Acad. Sci. USA, 83: 9065-9069, Dec. 1986.
Gould et al. "Chimerasome-Mediated Gene Transfer In Vitro and In Vivo", Gene, 84(2): 429-438, Dec. 1989. Abstract.
Grande et al. "Physiological Levels of 1Alpha, 25 Dihydroxyvitamin D3 Induce the Monocytic Commitment of CD34+ Hematopoietic Progenitors", J. Leukoc. Biol., 71(4): 641-651, 2002.
Grenda et al. "Mice Expressing a Neutrophil Elastase Mutation Derived From Patients With Severe Congenital Neutropenia Have Normal Granulopoiesis", Blood, 100(9): 3221-3228, 2002.
Gur et al. "Tolerance Induction by Megadose Hematopoietic Progenitor Cells: Expansion of Veto Cells by Short-Term Culture of Purified Human CD34+ Cells", Blood, 99(11): 4174-4181, 2002.
Haj-Ahmad et al. "Development of a Helper-Independent Human Adenovirus Vector and Its Use in the Transfer of the Herpes Simplex Virus Thymidine Kinase Gene", Journal of Virology, 57(1): 267-274, 1986.
Hamilton "Stem Cell Technology to Treat Leukemia Patients Show Promise", The Wall Street Journal, ONLINE, 2003.
Hammond et al. "Suppression of In Vitro Granulocytopoiesis by Captopril and Penicillamine", Experimental Hematology, 16(8): 674-680, 1988.
Handgretinger et al. "Biology and Plasticity of CD133+ Hematopoietic Stem Cells", Annals of the New York Academy of Scineces, 996: 141-151, May 2003.
Harada et al. "A Wilms Tumor Cell Line, HFWT, Can Greatly Stimulate Proliferation of CD56+ Human Natural Killer Cells and Their Novel Precursors in Blood Mononuclear Cells", Experimantal Hematology, 32: 614-621, 2004.
Hatayama et al. "Regulation of HSP70 Synthesis Induced by Cupric Sulfate and Zinc Sulfate in Thermotolerant HeLa Cells", Journal of Biochemistry, Tokyo, 114(4): 592-597, 1993. Abstract.
Haviernik et al. "Tissue Inhibitor of Matrix Metalloproteinase-1 Overexpression in M1 Myeloblasts Impairs IL-6-Induced Differentiation", Oncogene, 23(57): 9212-9219, Dec. 2004. Abstract.
Hayashi et al. "Changes in the Balance of Phosphoinositide 3-Kinase/Protein Kinase B (AKt) and the Mitogen-Activated Protein Kinases (ERK/p38MAPK) Determine a Phenotype of Visceral and Vascular Smooth Muscle Cells", The Journal of Cell Biology, 145(4): 727-740.
Haylock et al. "Ex-Vivo Expansion and Maturation of Peripheral Blood CD34+ Cells Into the Myeloid Lineage", Blood, 80(5): 1405-1412, 1992.
Hermonat et al. "Use of Adeno-Associated Virus as a Mammalian DNA Cloning Vector: Transduction of Neomycin Resistance Into Mammalian Tissue Culture Cells", Proc. Natl. Acad. Sci. USA, 81: 6466-6470, Oct. 1984.
Herz et al. "Adenovirus-Mediated Transfer of Low Density Lipoprotein Receptor Gene Acutely Accelerates Cholesterol Cleearence in Normal Mice", Proc. Natl. Acad. Sci. USA, 90: 2812-2816, Apr. 1993.
Heslop et al. "Long-Term Restoration of Immunity Against Epstein-Barr Virus Infection by Adoptive Transfer of Gene-Modified Virus-Specific T Lymphocytes", Nature Medicine, 2(5): 551-555, 1996.
Heuchel et al. "The Transcription Factor MTF-1 Is Essential for Basal and Heavy Metal-Induced Metallothionein Gene Expression", The EMBO Journal, 13(12): 2870-2875, 1994.
Hida et al. "Existence of Retinoic Acid-Receptor-Independent Retinoid X-Receptor-Dependent Pathway in Myeloid Cell Function", Japanese Journal of Pharmacology, 85(1): 60-69, 2001.
Higashi et al. "Autologous Bone-Marrow Mononuclear Cell Implantation Improves Endothelium-Dependent Vasodilation in Patients With Limb Ischemia", Circulation, 109: 1215-1218, Mar. 16, 2004.
Hino et al. "A Long-Term Culture of Human Hepatocytes Which Show a High Growth Potential and Express Their Differentiated Phenotypes", Biochemical and Biophysical Research Communications, 256(1): 184-191, Mar. 5, 1999. Abstract.
Hirase et al. "Anemia and Neutropenia in a Case of Copper Deficiency: Role of Copper in Normal in Hematopiesis", Acta Haematology, 87(4): 195-197, 1992.
Hirose et al. "Identification of a Transposon-Related RNA Down-Regulated by Retinoic Acid in Embryonal Carcinoma and Embryonic Stem Cells", Experimental Cell Research, 221(2): 294-300, 1995. Abstract.
Hmama et al. "1-Alpha, 25-Dihydroxyvitamin D3-Induced Myeloid Cell Differentiation Is Regulated by a Vitamin D Receptor-Phospatidylinositol 3-Kinase Signaling Complex", Journal of Experimental Medicine, 190(11): 1583-1594, 1999.
Hoffman et al. "Zinc-Induced Copper Deficiency", Gastroenterology, 94(2): 508-512, Feb. 1988.
Hofmeister et al. "Ex Vivo Expansion of Umbilical Cord Blood Stem Cells for Transplantation: Growing Knowledge From the Hematopoietic Niche", Bone Marrow Transplantation, 39: 11-23, 2007.
Holleman "Triethylene Tetramine, CAS No. 112-24-3", Chemical Hazard Information Profile Draft Report, 1982.
Hoogenboom et al. "By-Passing Immunisation. Human Antibodies From Synthetic Repertoires of Germline V[H] Gene Segments Rearranged In Vitro", Journal of Molecular Biology, 227: 381-388, 1992.
Hori et al. "Growth Inhibitors Promote Differentiation of Insulin-Producing Tissue From Embryonic Stem Cells", Proc. Natl. Acad. Sci. USA, 99(25): 16105-16110, 2002.
Hottinger et al. "The Copper Chelator D-Penicillamine Delays Onset of Disease a Extends Survival in a Transgenic Mouse Model of Familial Amyotrophic Lateral Sclerosis", European Journal of Neuroscience, 9(7): 1548-1551, Jul. 1997. Abstract.

(56) References Cited

OTHER PUBLICATIONS

Howard et al. "Formation and Hydrolysis of Cyclic ADP-Ribose Catalyzed by Lymphocyte Antigen CD38", Science, 262(5136): 1056-1059, Nov. 12, 1993. Abstract.
Huang et al. "Differentiation of Human U937 Promonocytic Cells Is Impaired by Moderate Copper Deficiency", Experimental Biology and Medicine, 226(3): 222-228, 2001.
Huber et al. "Retroviral-Mediated Gene Therapy for the Treatment of Hepatocellular Carcinoma: An Innovative Approach for Cancer Therapy", Proc. Natl. Acad. Sci. USA, 88: 8039-8043, Sep. 1991.
Huehn et al. "Molecular Analysis of CD26-Mediated Signal Transduction in T Cells", Immunology Letters, 72: 127-132, 2000.
Humeau et al. "Successful Reconstitution of Human Hematopoiesis in the SCID-Hu Mouse by Genetically Modified, Highly Enriched Progenitors Isolated From Fetal Liver", Blood, 90(9): 3496-3506, Nov. 1, 1997.
Hutvagner et al. "RNAi: Nature Abhors a Double-Strand", Current Opinion in Genetics and Development, 12: 225-232, 2002.
Hwu et al. "Functional and Molecular Characterization of Tumor-Infiltrating Lymphocytes Transduced With Tumor Necrosis Factir-? cDNA for the Gene Theraoy of Cancer in Humans", The Journal of Immunology, 150(9): 4104-4115, May 1, 1993.
Imai et al. "Selective Secretion of Chemoattractants for Haemapoietic Progenitor Cells by Bone Marrow Endothelial Cells: A Possible Role in Homing of Haemopoietic Progenitor Cells to Bone Marrow", British Journal of Haematology, 106: 905-911, 1999.
Imitola et al. "Directed Migration of Neural Stem Cells to Sites of CNS Injury by the Stroman Cell-Derived Factor 1?/CXC Chemokine Receptor 4 Pathway", Proc. Natl. Acad. Sci. USA, 101(52): 18117-18122, 2004.
Inbar et al. "Localization of Antibody-Combining Sites Within the Variable Portions of Heavy and Light Chains", Proc. Natl. Acad. Sci. USA, 69(9): 2659-2662, 1972.
Itoh et al. "Inhibition of Urokinase Receptor (uPAR) Expression by RNA-Cleaving Catalytic DNA (DNAzyme) Containing Antisense uPAR", Molecular Therapy, 5(5): 5134, 2002. Abstract 409.
Jackson et al. "Regeneration of Ischemic Cardiac Muscle and Vascular Endothelium by Adult Stem Cells", The Journal of Clinical Investigation, 107(11): 1395-1402, 2001.
Jelinek et al. "Novel Bioreactors for the Ex Vivo Cultivation of Hematopoietic Cells", English Life Science, 2(1): 15-18, 2002.
Jiang et al. "Phosphatidylinositol 3-Kinase Signaling Mediates Angiogenesis and Expression of Vascular Endothelial Growth Factor in Endothelial Cells", PNAS, 97(4): 1749-1753, 2000.
Johnson et al. "Synthesis and Biological Activity of High-Affinity Retinoic Acid Receptor Antagonists", Bioorganic & Medicinal Chemistry, 7(7): 1321-1338, 1999.
Johnson et al. "The Cytokines IL-3 and GM-CSF Regulate the Transcriptional Activity of Retinoic Acid Receptors in Different In Vitro Models of Myeloid Differentiation", Blood, 99(3): 746-753, 2002.
Jones et al. "Replacing the Complementarity-Determining Regions on a Human Antibody With Those From a Mouse", Nature, 321: 522-525, 1986.
Kaehne et al. "Dipeptidyl Peptidase IV: A Cell Surface Peptidase Involved in Regulating T Cell Growth (Review)", International Journal of Molecular Medicine, 4: 3-15, 1999.
Kahn et al. "Overexpression of CXCR4 on Human CD34+ Progenitors Increases Their Proliferation, Migration, and NOD/SCID Repopulation", Blood, 103(8): 2942-2949, Apr. 15, 2004.
Kang et al. "Retinoic Acid and Its Receptors Repress the Expression and Transactivation Functions of Nur77: A Possible Mechanism for the Inhibition of Apoptosis by Retinoic Acid", Experimental Cell Research, 256: 545-554, 2000.
Kastner et al. "Positive and Negative Regulation of Granulopoiesis by Endogenous RARalpha", Blood, 97(5): 1314-1320, 2001. Abstract.

Kaufman et al. "Translational Efficency of Polycistronic mRNAs and Their Utilization to Express Heterologous Genes in Mammalian Cells", The EMBO Journal, 6(1): 187-193, 1987.
Kawa et al. "Stem Cell Factor and/or Endothelin-3 Dependent Immortal Melanoblast and Melanocyte Populations Derived From Mouse Neural Crest Cells", Pigment Cell Research, 13(Suppl.8): 73-80, 2000.
Kay et al. "Hepatic Gene Therapy: Persistent Expression of Human Alphal-Antitrypsin in Mice After Direct Gene Delivery In Vivo", Human Gene Therapy, 3: 641-647, 1992.
Keith et al. "Multicomponent Therapeutics for Networked Systems", Nature Reviews: Drug Discovery, 4: 1-8, 2005.
Kern et al. "Comparative Analysis of Mesenchymal Stem Cells From Bone Marrow, Umbilical Cord Blood, or Adipose Tissue", Stem Cells, 24: 1294-1301, 2006.
Khachigian "DNAzymes: Cutting a Path to a New Class of Therapeutics", Current Opinion in Molecular Therapeutics, 4(2): 119-121, 2002.
Kim "Differentiation and Identification of the Two Catalytic Metal Binding Sites in Bovine Lens Leucine Aminopeptidase by X-Ray Crystallography", Proc. Natl. Acad. Sci. USA, 90(11): 5006-5010, 1993.
Kishimoto et al. "Molecular Mechanism of Human CD38 Gene Expression by Retinoic Acid. Identification of Retinoic Acid Response Element in the First Intron", The Journal of Biological Chemistry, 273(25): 15429-15434, 1998.
Kitanaka et al. "CD38 Ligation in Human B Cell Progenitors Triggers Tyrosine Phosphorylation of CD19 and Association of CD19 With Lyn and Phosphatidylinositol 3-Kinase", Journal of Immunology, 159(1): 184-192, Jul. 1997. Abstract.
Kizaki et al. Regulation of Manganese Superoxide Dismutase and Other Antioxidant Genes in Normal and Leukemic Hematopoietic Cells and Their Relationship to Cytotoxicity by Tumor Necrosis Factor, Blood, 82(4): 1142-1150, 1993.
Klingemann et al. "Ex Vivo Expansion of Natural Killer Cells for Clinical Applications", Cythotherapy, 6(1): 15-22, 2004.
Kobari et al. "CD133+ Cell Selection Is an Alternative to CD34+ Cell Selection for Ex Vivo Expansion of Hematopoietic Stem Cells", Journal of Hematotherapy & Stem Cell Research, 10(2): 273-281, 2001.
Kocher et al. "Neovascularization of Ischemic Myocardium by Human Bone-Marrow-Derived Angioblasts Prevents Cardiomyocyte Apoptosis, Reduces Remodeling and Improves Cardiac Function", Nature Medicine, XP002963458, 7(4): 430-436, 2001.
Koehl et al "Ex Vivo Expansion of Highly Purified NK Cells for Immunotherapy After Haploidentical Stem Cell Transplantation in Children", Klinische Paediatrie, 217: 345-350, 2005.
Koehler et al. "Defining Optimum Conditions for the Ex Vivo Expansion of Human Umbilical Cord Blood Cells Influences of Progenitor Enrichment, Interference With Feeder Layers, Early-Acting Cytokines and Agitation of Culture Vessels", Stem Cells, 17(1): 19-24, 1999.
Kohroki et al. "Induction of Differentiation and Apoptosis by Dithizone in Human Myeloid Leukemia Cell Lines", Leukemia Research, XP002264427, 22(5): 405-412, 1998.
Koizumi et al. "Large Scale Purification of Human Blood CD34+ Cells From Cryopreserved Peripheral Blood Stem Cells, Using a Nylon-Fiber Syringe System and Inununomagnetic Microspheres", Bone Marrow Transplantation, 26: 787-793, 2000.
Koller et al. "Large-Scale Expansion of Human Stem and Progenitor Cells From Bone Marrow Mononuclear Cells in Continous Perfusion Cultures", Blood, 82(2): 378-384, 1993.
Krause et al. "Multi-Organ, Multi-Lineage Engraftment by a Single Bone Marrow-Derived Stem Cell", Cell, 105(3): 369-377, 2001.
Kronenwett et al. "Oligodeoxyribonucleotide Uptake in Primary Human Hematopoietic Cells Is Enhanced by Cationic Lipids and Depends on the Hematopoietic Cell Subset", Blood, 91(3): 852-862, 1998.
Ku et al. "Committing Embryonic Stem Cells to Early Endocrine Pancreas in Vitro", Stem Cells, 22: 1205-1217, 2004.

(56) References Cited

OTHER PUBLICATIONS

Kumagai et al. "Ligation of CD38 Suppresses Human B Lymphopoiesis", Journal of Experimental Medicine, 181(3): 1101-1110, 1995.
Labrecque et al. "Impaired Granulocytic Differentiation in Vitro in Hematopoietic Cells Lacking Retinoic Acid Receptors ?1 and ?", Blood, 92(2): 607-615, Jul. 15, 1998.
Lagasse et al. "Purified Hematopoietic Stem Cells Can Differentiate Into Hepatocytes In Vivo", Nature Medicine, 6(11): 1229-1234, 2000. Abstract.
Lam et al. "Preclinical Ex Vivo Expansion of Cord Blood Hematopoietic Stem and Progenitor Cells: Duration of Culture; The Media, Serum Supplements, and Growth Factors Used; and Engraftment in NOD/SCID Mice", Transfusion, 41(12): 1567-1576, 2001. Abstract.
Lambeir et al. "Kinetic Investigation of Chemokine Truncation by CD26/DipeptidylPeptidase IV Reveals a Striking Selectivity Within the Chemokine Family", The Journal of Biological Chemistry, 276(32): 29839-29845, 2001.
Lange et al. "Biological and Clinical Advances in Stem Cell Expansion", Leukemia, 10: 943-945, 1996.
Lapidot et al. "Cytokine Stimulation of Multilineage Hematopoiesis From Immature Human Cells Engrafted in SCID Mice", Science, 255: 1137-1141, 1992. Abstract.
Larrick et al "PCR Amplification of Antibody Genes", Methods: A Companion to Methods in Enzymology, 2(2): 106-110, 1991.
Lassila et al. "Role for Lys-His-Gly-NH2 in Avian and Murine B Cell Development", Cellular Immunology, 122(2): 319-328, 1989.
Lau et al. "A Peptide Molecule Mimicking the Copper (II) Transport Site of Human Serum Albumin", Journal of Biological Chemistry, XP002264428, 249(18): 5878-5884, 1974.
Lavigne et al. "Enhanced Antisense Inhibition of Human Immunodeficiency Virus Type 1 in Cell Cultures by DLS Delivery System. A Comparative Study Between the Synthetic Site and Albumin", Biochemical and Biophysical Research Communications, 237: 566-571, 1997.
Lawlor et al. "Coordinate Control of Muscle Cell Survival by Distinct Insulin-Like Growth Factor Activated Signaling Pathways", The Journal of Cell Biology, 151(6): 1131-1140, 2000.
Lebkowski et al. "Rapid Isolation and Serum-Free Expansion of Human CD34+ Cells", Blood Cells, 20: 404-410, 1994.
Lee et al. "Clonal Expansion of Adult Rat Hepatic Stem Cell Lines by Suppression of Asymmetric Cell Kinetics (SACK)", Biotechnology and Bioengineering, 83(7): 760-771, Sep. 30, 2003.
Lee et al. "Effect of Vitamin D Analog, EB1089, on Hematopoietic Stem Cells From Normal and Myeloid Leukemic Blasts", Leukemia, 10: 1751-1757, 1996.
Lee et al. "Repair of Ischemic Heart Disease With Novel Bone Marrow-Derived Multipotent Stem Cells", Cell Cycle, 4(7): 861-864, 2005.
Lemarchand et al. "Adenovirus-Mediated Transfer of a Recombinant Human Alphal-Antitrypsin cDNA to Human Endothelial Cells", Proc. Natl. Acad. Sci. USA, 89: 6482-6486, 1992.
Leslie et al. "An Activating Mutation in the Kit Receptor Abolishes the Stroma Requirement for Growth of ELM Erythroleukemia Cells, But Does Not Prevent Their Differentiation in Response to Erythropoietin", Blood, 92(12): 4798-4807, 1998.
Lewandowski et al. "Phosphatidylinositol 3-Kinases Are Involved in the All-Trans Retinoic Acid-Induced Upregulation of CD38 Antigen on Human Haematopoietic Cells", British Journal of Hematology, 118(2): 535-544, 2002.
Li et al. "Activation of Phosphatidylinositol-3 Kinase (PI-3K) and Extracellular Regulated Kinases (Erk1/2) Is Involved in Muscarinic Receptor-Mediated DNA Synthesis in Neural Progenitor Cells", The Journal of Neuroscience, 21(5): 1569-1579, 2001.
Li et al. "Cell Life Versus Cell Longevity: Ther Mysteries Surrounding the NAD+ Precursor Nicotinamide", Current Medicinal Chemistry, XP002539111, 13(8): 883-895, Apr. 2006.
Lianguzova et al. "PI3-Kinase Inhibitors LY294002 and Wortmannin Have Different Effects on Proliferation of Murine Embryonic Stem Cells", Tsitologiia, 48(7): 560-568, 2006. Abstract.
Lonberg et al. "Antigen-Specific Human Antibodies From Mice Comprising Four Distinct Genetic Modifications", Nature, 368: 856-859, 1994.
Lonberg et al. "Human Antibodies From Transgenic Mice", International Review in Immunology, 13(1): 65-93, 1995. Abstract.
Lovejoy et al. "Novel 'Hybrid' Iron Chelators Derived From Aroylhydrazones and Thiosemicarbazones Demonstrate Selective Antiproliferative Activity Against Tumor Cells", Blood, 100(2): 666-676, 2002.
Lu et al. "Intravenous Administration of Human Umbilical Cord Blood Reduces Neurological Deficit in the Rat After Traumatic Brain Injury", Cell Transplantation, 11(3): 275-281, 2002. Abstract.
Luft "Making Sense Out of Antisense Oligodeoxynucleotide Delivery: Getting There Is Half the Fun", Journal of Molecular Medicine, 76: 75-76, 1998.
Lupi et al. "Endogenous ADP-Ribosylation of the G Protein? Subunit Prevents the Inhibition of Type 1 Adenylyl Cyclase", The Journal of Biological Chemistry, 275(13): 9418-9424, 2000.
Lutton et al "Zinc Porphyrins: Potent Inhibitors of Hematopoieses in Animal and Human Bone Marrow", Proc. Natl. Acad. Sci. USA, 94: 1432-1436, 1997.
Ma et al. "Inhibition of Phosphatidylinositol 3-Kinase Causes Apoptosis in Retinoic Acid Differentiated H1-60 Leukemia Cells", Cell Cycle, 3(1): 67-70, 2004.
Mader et al. "A Steroid-Inducible Promoter for the Controlled Overexpression of Cloned Genes in Eukaryotic Cells", Proc. Natl. Acad. Sci. USA, 90: 5603-5607, 1993.
Madlambayan et al. "Controlling Culture Dynamics for the Expansion of Hematopoietic Stem Cells", Journal of Hematotherapy and Stem Cell Research, 10(4): 481-492, Aug. 1, 2001. Abstract.
Manome et al. "Coinduction of C-Jun Gene Expression and Internucleosomal DNA Fragmentation by Ionizing Radiation", Biochemistry, 32: 10607-10613, 1993.
Mar et al. "A Conserved CATTCCT Motif Is Required for Skeletal Muscle-Specific Activity of the Cardiac Troponin T Gene Promoter", Proc. Natl. Acad. Sci. USA, 85: 6404-6408, 1988.
Marcinkowska "Does the Universal 'Signal Transduction Pathway of Differentiation' Exist? Comparison of Different Cell Differentiation Experimental Models With Differentiation of HL-60 Cells in Response to 1,25-Dihydroxyvitamin D3", Postepy Higieny i Medycyny, 53(2): 305-313, 1999.
Markel et al. "Natural Killer Lysis Receptor (NKLR)/NKLR-Ligand Matching as a Novel Approach for Enhancing Anti-Tumor Activity of Allogeneic NK Cells", PLoS One, 4(5): e5597-1-e5597-12, May 19, 2009.
Marks et al. "By-Passing Immunization. Human Antibodies From V-Gene Libraries Displayed on Phage", Journal of Molecular Biology, 222: 581-597, 1991.
Marks et al. "By-Passing Immunization: Building High Affinity Human Antibodies by Chain Shuffling", Biotechnology 10: 779-783, 1992.
Martelli et al. "Transplants Across Human Leukocyte Antigen Barriers", Seminars in Hematology, 39(1): 48-56, 2002.
Matuoka et al. "A Positive Role of Phosphatidylinositol 3-Kinase in Aging Phenotype Expression in Cultured Human Diploid Fibroblasts", Arch. Gerontol. Geriatry, 36:203-219, 2003.
Matzner et al. "Bone Marrow Stem Cell Gene Therapy of Arylsulfatase A-Deficient Mice, Using an Arylsulfatase a Mutant That Is Hypersecreted From Retrovirally Transduced Donor-Type Cells", Human Gene Therapy, 12: 1021-1033, 2001.
McGrath et al. "Embryonic Expression and Function of the Chemokine SDF-1 and Its Receptor, CXCR4", Developmental Biology, 213: 442-456, 1999.
McLaughlin et al. "Adeno-Associated Virus General Transduction Vectors: Analysis of Proviral Structures", Journal of Virology, 62(6): 1963-1973, 1988.
McNiece et al. "Action of Interleukin-3, G-CSF on Highly Enriched Human Hematopoietic Preogenitor Cells: Synergistic Interaction of GM-CSF Plus G-CSF", Blood, 74: 110-114, 1989.

(56) References Cited

OTHER PUBLICATIONS

McNiece et al. "CD34+ Cell Selection From Frozen Cord Blood Products Using the Isolex 300i and CliniMACS CD34 Selection Devices", Journal of Hematotherapy, 7: 457-461, 1998.

McNiece et al. "Ex Vivo Expansion of Cord Blood Mononuclear Cells on Mesenchymal Stem Cells", Cytotherapy, XP009069244, 6(4): 311-317, Jan. 1, 2004. Abstract.

Mehta et al. "Human CD38, A Cell-Surface Protein With Multiple Functions", The FASEB Journal, 10(12): 1408-1417, 1996.

Mehta et al. "Involvement of Retinoic Acid Receptor-?-Mediated Signaling Pathway in Induction of CD38 Cell-Surface Antigen", Blood, 89(10): 3607-3614, 1997. Abstract.

Mehta et al. "Retinoid-Mediated Signaling Pathways in CD38 Antigen Expression in Myeloid Leukemia Cells", Leukemia and Lymphoma, 32(5/6): 441-449, 1999.

Meissner et al. "Development of a Fixed Bed Bioreactor for the Expansion of Human Hematopoietic Progenitor Cells", Cytotechnology, 30: 227-234, 1999.

Merck & Co. "The Merck Index, An Encyclopedia of Chemicals, Drugs and Biologicals", 10th Ed.(3742): 549, 1983.

Meyer-Monard et al. "Clinical-Grade Purification of Natural Killer Cells in Haploidentical Hematopoietic Stem Cell Transplantation", Transfusion, 49: 362-371, Feb. 2009.

Mezey et al. "Turning Blood Into Brain: Cells Bearing Neuronal Antigens Generated In Vivo From Bone Marrow", Science, 290(5497): 1779-1782, 2000.

Migliaccio et al. "Long-Term Generation of Colony-Forming Cells in Liquid Culture of CD34+ Cord Blood Cells in the Presence of Recombinant Human Stem Cell Factor", Blood, 79: 2620-2627, 1992.

Miller "Progress Toward Human Gene Therapy", Blood, The Journal of the American Society of Hematology, 76(2): 271-278, 1990.

Miller et al. "Expansion In Vitro of Adult Murine Hematopoietic Stem Cells With Transplantable Lympho-Myeloid Reconstituting Ability", Proc. Natl. Acad. Sci. USA, 94: 13648-13653, 1997.

Miller et al. "Role of Monocytes in the Expansion of Human Activated Natural Killer Cells", Blood, 80(9): 2221-2229, Nov. 1, 1992.

Mills et al. "Regulation of Retinoid-Induced Differentiation in Embryonal Carcinoma PCC4.Aza 1 R Cells: Effects of Retinoid-Receptor Selective Ligands", Cell Growth Differ., 7(3): 327-337, 1996. Abstract.

Miraglia et al. "A Novel Five-Transmembrane Hematopoietic Stem Cell Antigen: Isolation, Characterization, and Molecular Cloning", Blood, 90(12): 5013-5021, 1997.

Mood et al. "Contribution of JNK, Mek, Mos and PI-3K Signalling to GVBD in Xenopus Oocytes", Cell. Signalling, 16(5): 631-342, 2004. Abstract.

Moore et al. "Ex Vivo Expansion of Cord Blood-Devined Stem Cells and Progenitons", Blood Cells, 20: 468-481, 1994.

Morier-Teissier et al. "Synthesis and Antitumor Properties of an Anthraquinone Bisubstituted by the Copper Chelating Peptide Gly-Gly-L-His", Journal of Medical Chemistry, 36: 2084-2090, 1993. Abstract.

Morimoto et al. "EDTA Induces Differentiation and Suppresses Proliferation of Promyelotic Leukemia Cell Line HL-60—Possible Participation of Zinc-", Biochemistry International, 28(2): 313-321, 1992.

Morita et al. "Heterogeneity and Hierarchy Within Most Primitive Hematopoietic Stem Cell Compartment", The Journal of Experimental Medicine, JEM, 207(6): 1173-1182, Jun. 7, 2010.

Morosetti et al. "Infrequent Alterations of the RAR? Gene in Acute Myelogenous Leukemias, Retinoic Acid-Resistant Acute Promyelocytic Leukemias, Myelodysplastic Syndromes, and Cell Lines", Blood, 87(10): 4399-4403, May 15, 1996.

Morrison "Success in Specification", Nature, 368(6474): 812-813, 1994.

Morrison et al. "Identification of a Lineage of Multipotent Hematopoietic Progenitors", Development, 124: 1929-1939, 1997.

Morrison et al. "The Long-Term Repopulating Subset of Hematopoietic Stem Cell Is Deterministic and Isolatable by Phenotype", Inununity, 1: 661-673, 1994. Abstract.

Mueller et al. "Heterozygous PU.1 Mutations Are Associated With Acute Myeloid Leukemia", Blood, 100(3): 998-1007, 2002.

Muench et al. "Interactions Among Colony-Stimulating Factors, IL-1?, IL-6, and Kit-Ligand in the Regulation of Primitive Murine Hematopoietic Cells", Experimental Hematology, 20: 339-349, 1992.

Mulloy et al. "Maintaining the Self-Renewal and Differentiation Potential of Human CD34+ Hematopoietic Cells Using a Single Genetic Element", Blood, 102(13): 4369-4376, 2003.

Munshi et al. "Evidence for a Casual Role of CD38 Expression in Granulocytic Differentiation of Human HL-60 Cells", The Journal of Biological Chemistry, 277(51) Issue of Dec. 20, pp. 49453-49458—2002.

Muramatsu et al. "Reversible Integration of the Dominant Negative Retinoid Receptor Gene for Ex Vivo Expansion of Hematopoietic Stem/Progenitor Cells", Biochemical & Biophysical Research Communications, 285(4): 891-896, 2001. Abstract.

Murray et al. "Modulation of Murine Lymphocyte and Macrophage Proliferation by Parenteral Zinc", Clinical and Experimental Immunology, 53(3): 744-749, 1983.

Murray et al. "Thrombopoietin, Flt3, and Kit Ligands Together Suppress Apoptosis of Human Mobilized CD34+ Cells and Recruit Primitive CD34+Thy-1+ Cells Into Rapid Division", Experimental Hematology, 27: 1019-1028, 1999.

Murry et al. "Haematopoietic Stem Cells Do Not Transdifferentiate Into Cardiac Myocytes in Myocardial Infarcts", Nature, 428: 664-668, Mar. 21, 2004.

Muzyczka "Use of Adeno-Associated Virus as a General Transduction Vector for Mammalian Cells", Current Topics in Microbiology and Immunology, 158: 97-129, 1992.

Nagaya et al. "Intravenous Administration of Mesenchymal Stem Cells Improves Cardiac Functions in Rats With Acute Myocardial Infarction Through Angiogenesis and Myogenesis", American Journal of Physiology—Heart Circulation Physiology, 287: H2670-H2676, 2004.

Narita et al. "Cardiomycyte Differentiation by GATA-4-Deficient Embryonic Stem Cells", Development, 122(19): 3755-3764, 1996.

Nguyen et al. "The Search for Endogenous Activators of the Aryl Hydrocarbon Receptor", Chemical Research in Toxicology, 21(1): 102-116, Jan. 2008.

Nicolau et al. "Liposomes as Carriers for In Vivo Gene Transfer and Expression", Methods in Enzymology, 149(Chap.16): 157-176, 1987.

Ohishi et al. "Delta-1 Enhances Marrow and Thymus Repopulating Ability of Human CD34+CD38- Cord Blood Cells", The Journal of Clinical Investigation, 110(8): 1165-1174, 2002.

Okazaki et al. "Characteristics and Partial Purification of a Novel Cytosolic, Magnesium-Independent, Neutral Sphingomyelinase Activated in the Early Signal Transduction of 1?,25-Dihydroxyvitamin D3-Induced HL-60 Cell Differentiation", The Journal of Biological Chemistry, 269(6): 4070-4077, 1994.

Okuno et al. "Differential Regulation of the Human and Murine CD34 Genes in Hematopoietic Stem cells", Proc. Natl. Acad. Sci, 99(9): 6246-6251, 2002.

Olivares et al. "Copper As an Essential Nutrient", The American Journal of Clinical Nutrition, 63: 791S-796S, 1996. Abstract.

Olsen et al. "Tissue-Specific Homing and Expansion of Donor NK Cells in Allogeneic Bone Marrow Transplantation", The Journal of Immunology, XP009147122, 183(5): 3219-3228, Sep. 2009.

Peled et al. "Cellular Copper Content Modulates Differentiation and Self-Renewal in Cultures of Cord Blood-Derived CD34+ Cells", British Journal of Haematology, 116(3): 655-661, 2002.

Peled et al. "Chelatable Cellular Copper Modulates Differentiation and Self-Renewal of Cord Blood-Derived Hematopoietic Progenitor Cells", Experimental Hematology, 33: 1092-1100, 2005.

Peled et al. "Copper Chelators Enable Long Term CFU and CD34+ Cells Expansions in Cultures Initiated With the Entire Mononuclear Cell (MNC) Fraction", Blood, 100(11), 2002. Abstract #4076.

(56) References Cited

OTHER PUBLICATIONS

Peled et al. "Copper Chelators Sustain Long-Term Expansion of Cord-Blood CD34+ Cultures Initiated With IL-3 and G-CSF—Late Acting, Differentiation-Inducing Cytokines", Blood, 96(1): 773a, Abstract 3343, 2000.
Peled et al. "Dependence of Human Stem Cell Engraftment and Repopulation of NOD/SCID Mice on CXCR4", Science, XP002180064, 283: 845-848, Feb. 5, 1999.
Peled et al. "Identification of a Serum-Derived Differentiation-Inducing Activity as the Copper-Binding Protein Ceruloplasmin", Blood, 92(10, Suppl.1, Part 1-2): 618A-619A, 1998.
Peled et al. "Linear Polyamine Copper Chelator Tetraethylenepentamine Augments Long-Term Ex Vivo Expansion of Cord Blood-Derived CD34+ Cells and Increases Their Engraftment Potential in NOD/SCID Mice", Experimental Hematology, 32: 547-555, 2004.
Peled et al. "Nicotinamide Modulates Ex-Vivo Expansion of Cord Blood Derived CD34+ Cells Cultures With Cytokines and Promotes Their Homing and Engraftment in SCID Mice", Blood, XP009134130, 108(11/Pt.1): 218A, #725, Nov. 1, 2006.
Peled et al. "Regulation of Long-Tenn Expansion of Hemopoietic Stem/Progenitor Cells (HPC) by Intracellular Copper Content", Blood, 96(11/Pt.1): 776a-777a, 2000.
Pera "Human Pluripotent Stem Cells: A Progress Report", Current Opinion in Genetics & Development, 11: 595-599, 2001.
Percival "Copper and Immunity", American Journal of Clinical Nutrition, 67(5 Suppl.): 1064S-1068S, 1998.
Percival "Neutropenia Caused by Copper Deficiency: Possible Mechanism of Action", Nutrition Reviews, 53(3): 59-66, 1995.
Percival et al. "Copper Is Required to Maintain Cu/Zn-Superoxide Dismutase Activity During HL-60 Cell Differentiation", Proc. Soc. Exp. Biol. Med., 203: 78-83, 1993.
Percival et al. "HL-60 Cells Can Be Made Copper Deficient by Incubating With Tetraethylenepentamine 1,2,3", Journal of Nutrition, 122(12): 2424-2429, 1992.
Perrotti et al. "Overexpression of the Zinc Finger Protein MZF1 Inhibits Hematopoietic Development From Embryonic Stem Cells: Correlation With Negative Regulation of CD34 and C-MYB Promoter Activity", Molecular and Cellular Biology, 15(11): 6075-6087, 1995.
Peters et al. "Long-Term Ex Vivo Expansion of Human Fetal Liver Primitive Haematopoietic Progenitor Cells in Stroma-Free Cultures", British Journal of Haematology, 119: 792-802, 2002.
Petersen et al. "Bone Marrow as a Potential Source of Hepatic Oval Cells", Science, 284(5417): 1168-1170, 1999. Abstract.
Petersen et al. "Hepatic Oval Cells Express the Hematopoietic Stem Cell Marker Thy-1 in the Rat", Hepatology, 27(2): 433-445, 1998.
Petti et al. "Complete Remission Through Blast Cell Differentiation in PLZF/RAR?-Positive Acute Promyelocytic Leukemia: In Vitro and In Vivo Studies", Blood, 100(3): 1065-1067, 2002.
Petzer et al. "Differential Cytokine Effects on Primitive (CD34+CD38-) Human Hematopoietic Cells: Novel Responses to Flt3-Ligand and Thrombopoietin", Journal of Experimental Medicine, 183: 2551-2558, 1996.
Petzer et al. "Self-Renewal of Primitive Human Hematopoietic Cells (Long-Term-Culture-Initiating Cells) In Vitro and Their Expansion in Defined Medium", Proc. Natl. Acad. Sci. USA, 93: 1470-1474, Feb. 1996.
Piacibello et al. "Extensive Amplification and Self-Renewal of Human Primitive Hematopoietic Stem Cells From Cord Blood", Blood, 89(8): 2644-2653, 1997.
Pickart et al. "Growth Modulating Plasma Tripeptide May Function by Facilitating Copper Uptake Into Cells", Nature, 288(18/25): 715-717, 1980. Abstract.
Podesta et al. "Cyclic ADP-Ribose Generation by CD38 Improves Human Hemopoietic Stem Cell Engraftment Into NOD/SCID Mice", The FASEB Journal, 17: 310-312, 2003.
Podesta et al. "Extracellular Cyclic ADP-Ribose Increases Intracellular Free Calcium Concentration and Stimulates Proliferation of Human Hematopoietic Progenitors", FASEB Journal, 14(5): 680-690, 2000.
Porter "The Hydrolysis of Rabbit?—Globulin and Antibodies With Crystalline Papain", Biochemical Journal, 73: 119-126, 1959.
Porter et al. "Graft-Versus-Leukemia Effect of Allogeneic Bone Marrow Transplantation and Donor Mononuclear Cell Infusions", Cancer Treatment & Research, 77: 57-85, 1997. Abstract.
Presta "Antibody Engineering", Current Opinion in Structural Biology, 2: 593-596, 1992.
Prockop et al. "Isolation and Characterization of Rapidly Self-Renewing Stem Cells From Cultures of Human Marrow Stromal Cells", Cytotherapy, 3(5): 393-396, 2001.
Protti et al. "Particulate Naturally Processed Peptides Prime a Cytotoxic Response Against Human Melanoma in Vitro", Cancer Research, 56: 1210-1213, 1996.
Psaltis et al. "Enrichment for STRO-1 Expression Enhances the Cardiovascular Paracrine Activity of Human Bone Marrow-Derived Mesenchymal Cell Populations", Journal of Cellular Physiology, 223: 530-540, 2010.
Puccetti et al. "AML-Associated Translocation Products Block Vitamin D3-Induced Differentiation by Sequestering the Vitamin D3 Receptor", Cancer Research, 62: 7050-7058, 2002.
Punzel et al. "The Type of Stromal Feeder Used in Limiting Dilution Assays Influences Frequency and Maintenance Assessment of Human Long-Term Culture Initiating Cells", Leukemia, 13: 92-97, 1999.
Purdy et al. "Large Volume Ex Vivo Expansion of CD34+-Positive Hematopoietic Progenitor Cells for Transplantation", Journal of Hematotherapy, 4: 515-525, 1995.
Purton et al. "All-Trans Retinoic Acid Delays the Differentiation of Primitive Hematopoietic Precursors (Lin c-kit+sca-l+) While Enhancing the Terminal Maturation of Committed Granulocyte/Monocyte Progenitors", Blood, 94(2); 483-495, 1999.
Purton et al. "All-Trans Retinoic Acid Enhances the Long-Term Repopulating Activity of Cultured Hematopoietic Stem Cells", Blood, 95(2): 470-477, 2000. Abstract.
Purton et al. "All-Trans Retinoic Acid Facilities Oncoretrovirus-Mediated Transduction of Hematopoietic Repopulating Stem Cells", J. Hematother. Stem Cell Res., 10(8): 815-825, 2001. Abstract.
Quantin et al. "Adenovirus as an Expression Vector in Muscle Cells In Vivo", Proc. Natl. Acad. Sci. USA, 89: 2581-2584, 1992.
Rajur et al. "Covalent Protein-Oligonucleotide Conjugates for Efficient Delivery of Antisense Molecules", Bioconjugate Chem., 8(6): 935-940, 1997.
Ramsfjell et al. "Distinct Requirements for Optimal Growth and In Vitro Expansion of Human CD34+CD38- Bone Marrow Long-Term Culture-Initiating Cells (LTC-IC), Extended LTC-IC, and Murine In Vivo Long-Term Reconstituting Stem Cells", Blood, 94(12): 4093-4102, 1999.
Rankin et al. "Quantitative Studies of Inhibitors of ADP-Ribosylation In Vitro and In Vivo", The Journal of Biological Chemistry, 264(8): 4312-4317, 1989.
Ratajczak et al. "Effect of Basic (FGF-2) and Acidic (FGF-1) Fibroblast Growth Factors on Early Haemopoietic Cell Development", British Journal of Hematology, 93: 772-782, 1996.
Ratajczak et al. "Hunt for Pluripotent Stem Cell—Regenerate Medicine Search for Almighty Cell", Journal of Autoimmunity, 30: 151-162, 2008.
Reeves et al. "High Zinc Concentrations in Culture Media Affect Copper Uptake and Transport in Differentiated Human Colon Adenocarcinoma Cells", Journal of Nutrition, 126(6): 1701-1712, 1996. Abstract.
Reid et al. "Interactions of Tumor Necrosis Factor With Granulocyte-Macrophage Colony-Stimulating Factor and Other Cytokines in the Regulation of Dendritic Cell Growth In Vitro From Early Bipotent CD34+ Progenitors in Human Bone Marrow", Journal of Immunology, 149(8): 2681-2688, 1992.
Reya "Regulation of Hematopoietic Stem Cell Self-Renewal", Recent Progress in Hormone Research, 58: 283-295, 2003.

(56) References Cited

OTHER PUBLICATIONS

Reyes et al. "Origin of Endothelial Progenitors in Human Postnatal Bone Marrow", Journal of Clinical Investigation, 109: 337-346, 2002.
Riechmann et al. "Reshaping Human Antibodies for Therapy", Nature, 332: 323-327, 1988.
Roach et al. "Methods for the Isolation and Maintenance of Murine Embryonic Stem Cells", Methods in Molecular Biology: Embryonic Stem Cells: Methods and Protocols, 185: 1-16, 2002.
Roberts "Mesenchymal Stem Cells", Vox Sanguinis, 87(Suppl.2): S38-S41, 2004.
Robertson et al. "Biology and Clinical Relevance of Human Natural Killer Cells", Blood, 76(12): 2421-2438, Dec. 15, 1990.
Robinson et al. "Ex Vivo Expansion of Umbilical Cord Blood", Cytotherapy, XP009120788, 7(3): 243-250, 2005.
Robinson et al. "Superior Ex Vivo Cord Blood Expansion Following Co-Culture With Bone Marrow-Derived Mesenchymal Stem Cells", Bone Marrow Transplantation, 37: 359-366, 2006.
Rosenberg Lymphokine-Activated Killer Cells: A New Approach to Immunotherapy of Cancer, Journal of the National Cancer Institute, JNCI, 75(4): 595-603, Oct. 1985.
Rosenberg et al. "Prospective Randomized Trial of High-Dose Interleukin-2 Alone or in Conjunction With Lymphokine-Activated Killer Cells for the Treatment of Patients With Advanced Cancer", Journal of the National Cancer Institute, 85(8): 622-632, Apr. 21, 1993.
Rosenfeld et al. "Adenovirus-Mediated Transfer of a Recombinant Alpha1-Antitrypsin Gene to the Lung Epithelium In Vivo", Science, 252: 431-434, 1991.
Rosenfeld et al. "In Vivo Transfer of the Human Cystic Fibrosis Transmembrane Conductance Regulator Gene to the Airway Epithelium", Cell, 68: 143-155, 1992.
Ross et al. "Chelometric Indicator Titrations With the Solid-State Cupric Ion-Selective Electrode", Analytical Chemistry, 41(13): 1900-1902, 1969.
Rowley et al. "Isolation of CD34+ Cells From Blood Stem Cell Components Using the Baxter Isolex System", Bone Marrow Transplantation, 21: 1253-1262, 1998.
Rubinstein et al. "Processing and Cryopreservation of Placental/Umbilical Cord Blood for Unrelated Bone Marrow Reconstitution", Proc. Natl. Acad. Sci. USA, 92: 10119-10122, 1995.
Rusten et al. "The RAR-RXR as Well as the RXR-RXR Pathway Is Involved Signaling Growth Inhibition of Human CD34+ Erythroid Progenitor Cells", Blood, 87(5): 1728-1736, 1996. Abstract.
Ryu et al. "Adenosine Triphosphate Induces Proliferation of Human Neural Stem Cells: Role of Calcium and P70 Ribosomal Protein S6 Kinase", Journal of Neuroscience Research, 72: 352-362, 2003.
Sammons et al. "Mechanisms Mediating the Inhibitory Effect of All-Trans Retinoic Acid on Primitive Hematopoietic Stem Cells in Human Long-Term Bone Marrow Culture", Stem Cells, 18(3): 214-219, May 2000.
Samulski et al. "Helper-Free Stocks of Recombinant Adeno-Associated Viruses: Normal Integration Does Not Require Viral Gene Expression", Journal of Virology, 63(9): 3822-3828, Sep. 1989.
Sandstrom et al. "Effects of CD34+ Cell Selection and Perfusion on Ex Vivo Expansion of Peripheral Blood Mononuclear Cells", Blood, 86(3): 958-970, 1995.
Santoro et al. "A General Purpose RNA-Cleaving DNA Enzyme", Proc. Natl. Acad. Sci. USA, 94(9): 4262-4266, Apr. 1997.
Sato et al. "In Vitro Expansion of Human Peripheral Blood CD34+ Cells", Blood, 82(12): 3600-3609, Dec. 15, 1993.
Sauve et al. "Mechanism-Based Inhibitors of CD38: A Mammalian Cyclic ADP-Ribose Synthetase", Biochemistry, 41(26): 8455-8463, Jul. 2, 2002.
Schechter et al. The Molecular Basis of Blood Diseases, p. 179-218, 1987. Abstract.
Schleinitz et al. "Natural Killer Cells in Human Autoimmune Diseases", Immunology, 131: 451-458, 2010.
Schmetzer et al. "Effect of GM-CSF, 1,25-Dihydmxycholecalciferol (Vit. D) and All-Trans-Retinocin Acid (ATRA) on the Proliferation and Differentiation of MDS-Bone Marrow (BM)-Cells In Vitro", Hematology, 2(1): 11-19, Jan. 1997.
Schwartz et al. "In Vitro Myelopoiesis Stimulated by Rapid Medium Exchange and Supplementation With Hematopoietic Growth Factors", Blood, 78(12): 3155-3161, Dec. 15, 1991.
Seed "An LFA-3 cDNA Encodes a Phospholipid-Linked Membrane Protein Homologous to Its Receptor CD2", Nature, 329(6142): 840-842, Oct. 29, 1987.
Segev et al. "Differentiation of Human Embryonic Stem Cells Into Insulin-Producing Clusters", Stem Cells, XP009038283, 22(3): 265-274, Jan. 1, 2004. Abstract.
Sekhar et al. "Retroviral Transduction of CD34-Enriched Hematopoietic Progenitor Cells Under Serum-Free Conditions", Human Gene Therapy, 7(1): 33-38, Jan. 1, 1996.
Selden "Transfection Using DEAE-Dextran", Short Protocols in Molecular Biology, Unit 9.2: 9-9-9-11, 1984.
Selden et al. "Optimization of Transfection", Short Protocols in Molecular Biology, Unit 9.4: 262-263, 1984.
Sergeant et al. "Iron and Copper Requirements for Proliferation and Differentiation of a Human Promyelocytic Leukemia Cell Line (HL-60)", Journal of Cellular Physiology, 163(3): 477-485, Jun. 1995.
Shimakura et al. "Murine Stromal Cell Line HESS-5 Maintains Reconstituting Ability of Ex Vivo-Generated Hematopoietic Stem Cells From Human Bone Marrow and Cytokine-Mobilized Peripheral Blood", Stem Cells, 18(3): 183-189, May 2000.
Shimizu et al. "Treatment and Management of Wilson's Disease", Pediatrics International, 41(4): 419-422, Aug. 1999. Abstract.
Shioda et al. "Anti-HIV-1 and Chemotactic Activities of Human Stromal Cell-Derived Factor 1Alpha (SDF-Alpha) and SDF-1Beta Are Abolished by CD26/Dipeptidyl Peptidase IV-Mediated Cleavage", Proc. Natl. Acad. Sci. USA, 95: 6331-6336, 1998.
Sieff et al. "Changes in Cell Surface Antigen Expression During Hemopoietic Differentiation", Blood, 60(3): 703-713, 1982. Abstract.
Siena et al. "Massive Ex Vivo Generation of Functional Dendritic Cells From Mobilized CD34+ Blood Progenitors for Anticancer Therapy", Experimental Hematology, 23: 1463-1471, 1995.
Sigurdsson et al. "Copper Chelation Delays the Onset of Prion Disease", The Journal of Biological Chemistry, 278(47): 46199-49202, Nov. 21, 2003.
Silvenoinen et al. "CD38 Signal Transduction in Human B Cell Precursors Rapid Induction of Tyrosine Phosphorylation, Activation of Syk Tyrosine Kinase and Phosphorylation of Phospholipase GGamma and Phosphatidylinositol 3-Kinase", Journal of Immunology, 156(1): 100-107, 1996. Abstract.
Simmons et al. "Identification of Stromal Cell Precursors in Human Bone Marrow by a Novel Monoclonal Antibody, STRO-1", Blood, 78(1): 55-62, 1991.
Simon et al. "Copper Deficiency and Sideroblastic Anemia Associated With Zinc Ingestion", American Journal of Hematology, 28(3): 181-183, Jul. 1988.
Slavin et al. "Donor Lymphocyte Infusion: The use of Alloreactive and Tumor-Reactiove Lymphocytes for Immunotherapy of Malignant and Nonmalignant Diseases in Conjunction With Allogeneic Stem Cell Transplantation", Stat-of-the-Art Review, Journal of Hematotherapy, 11: 265-276, 2002.
Slavin et al. "Treatment of Leukemia by Alloreactive Lymphocytes and Nonmyeloablative Stem Cell Transplantation", Journal of Clinical Immunology, 22(2): 64-69, Mar. 2002.
Smith "Embryo-Derived Stem Cells: of Mice and Men", Annual Reviews of Cell and Developmental Biology, 17: 435-462, 2001.
Smith "The World According to PARP", Trends in Biochemical Sciences, 26(3): 174-179, 2001.
Spencer et al. "Controlling Signal Transduction With Synthetic Ligands", Science, 262(5136): 1019-1024, Nov. 12, 1993.
Sprangrude et al. "Purification and Characterization of Mouse Hematopoietic Stem Cells", Science, 241(4861): 58-62, Jul. 1, 1988.
Struyf et al. "Natural Truncation of RANTES Abolishes Signaling Through the CC Chemokine Receptors CCR1 and CCR3, Impairs Its Chemotactic Potency and Generates a CC Chemokine Inhibitor", European Journal Immunology, 28: 1262-1271, 1998.

(56) References Cited

OTHER PUBLICATIONS

Suda et al. "A Study of Trientine Therapy in Wilson's Disease With Neurology Symptoms", No To Hattatsu, Brain and Development, 25(5): 429-34, Sep. 1993. Abstract.
Sylvester et al. "Stem Cells: Review and Update", Archives of Surgery, 139: 93-99, 2004.
Szilvassy et al. "Differential Homing and Engraftment Properties of Hematopoetic Progenitor Cells From Murine Bone Marrow Mobilized Peripheral Blood Cells and Fetal Liver", Blood, 98(7): 2108-2115, Oct. 2001.
Takeshita et al. "Selective Stimulation by Ceramide of the Expression of the Alpha Isoform of Retinoic Acid and Retinoid X Receptors in Osteoblastic Cells", Journal of Biological Chemistry, 275(41): 32220-32226, Published Online 2000.
Tashiro-Itoh et al. "Metallothionein Expression and Concentrations of Copper and Zinc Are Associated With Tumor Differentiation in Hepatocellular Carcinoma", Liver, 17: 300-306, 1997.
Tateishi-Yuyama et al. "Therapeutic Angiogenesis for Patients With Limb Ischaemia by Autologous Transplantation of Bone-Marrow Cells: A Pilot Study and a Randomised Controlled Trial", The Lancet, 360(9331): 427-435, Aug. 10, 2002.
Tateno et al. "Long-Term Cultivation of Adult Rat Hepatocytes That Undergo Multiple Cell Divisions and Express Normal Parenchymal Phenotypes", American Journal of Pathology,148(2): 383-392, Feb. 1996.
Thiotepa "Thiotepa Product Identification Sheet", Em Science, 6505-01-047-3872, 1990.
Todisco et al. "CD38 Ligation Inhibits Normal and Leukemic Myelopoiesis", Blood, 95(2): 535-542, 2000. Abstract.
Toegel et al. "Administered Mesenchymal Stem Cells Protect Against Ischemic Acute Renal Failure Through Differentiation-Independent Mechanisms", American Journal of Physiology—Renal Physiology, 289: F31-F42, 2005.
Tratschin et al. "A Human Parvovirus, Adeno-Associated Virus, as a Eucaryotic Vector: Transient Expression and Encapsidation of the Procaryotic Gene for Chloramphenicol Acetyltransferase", Molecular and Cellular Biology, 4(10): 2072-2081, Oct. 1984.
Tratschin et at "Adeno-Associated Virus Vector for High-Frequency Integration, Expression, and Rescue of Genes in Mammalian Cells", Molecular and Cellular Biology, 5(11): 3251-3260, Nov. 1985.
Tratschin et al. "Genetic Analysis of Adeno-Associated Virus: Properties of Deletion Mutants Constructed In Vitro and Evidence for an Adeno-Associated Virus Replication Function", Journal of Virology, 51(3): 611-619, Sep. 1984.
Trounson "The Derivation and Potential Use of Human Embryonic Stem Cells", Reproduction, Fertility and Development, 13: 523-532, 2001.
Tse et al. "Angiogenesis in Ischaemic Myocardium by Intramyocardial Autologous Bone Marrow Mononuclear Cell Implantation", Lancet, 361: 47-49, 2003.
Tuba et al. "Synthesis and Structure—Activity Relationship of Neuromuscular Blocking Agents", Current Medicinal Chemistry, 9(16): 1507-1536, 2002.
Turnpenny et al. "Evaluating Human Embryonic Germ Cells: Concord and Conflict as Pluripotent Stem Cells", Stem Cells, 24: 212-220, 2006.
Uchida et al. "Direct Isolation of Human Central Nervous System Stem Cells", Proc. Natl. Acad. Sci. USA, 97(26): 14720-14725, 2000.
Ueda et al. "ADP-Ribosylation", Annual Reviews of Biochemistry, 54: 73-100, 1985.
Ueno et al. "A Novel Retinoic Acid Receptor (RAR)-Selective Antagonist Inhibits Differentiation and Apoptosis of HL-60 Cells: Implications of RAR?-Mediated Signals in Myeloid Leukemic Cells", Leukemia Research, 22(6): 517-525, 1998.
Vaca et al. "Nicotinamide Induces Both Proliferation and Differentiation of Embryonic Stem Cells Into Insulin-Producing Cells", Transplantion Proceedings, XP002539110, 35(5): 2021-2023, Aug. 2003. Abstract.
Van Beusechem et al. "Long-Term Expression of human Adenosine Deaminase in Rhesus Monkeys Transplanted With Retrovirus-Infected Bone-Marrow Cells", Proc. Natl. Acad. Sci. USA, 89: 7640-7644, 1992.
Van Epps et al. "Harvesting, Characterization, and Culture of CD34+ Cells From Human Bone Marrow, Peripheral Blood, and Cord Blood", Blood Cells, XP009082098, 20(2-3): 411-423, 1994.
Vanham et al. "Decreased Expression of the Memory Marker CD26 on Both CD4+ and CD8+ T Lymphocytes of HIV-Infected Subjects", Journal of Acquired Immune Deficiency Syndromes, 6: 749-757, 1993.
Verfaillie "Can Human Hematopoietic Stem Cells Be Cultured Ex Vivo?", Stem Cells, 12(5): 466-476, 1994. Abstract.
Verfaillie "Direct Contact Between Human Primitive Hematopoietic Progenitors and Bone Marrow Stroma Is Not Required for Long-Term In Vitro Hematopoiesis", Blood, 79(11): 2821-2826, 1992.
Verhoeyen et al. "Reshaping Human Antiodies: Grafting An Antilysozyme Activity", Science, 239: 1534-1536, 1988.
Verlinden et al. "Interaction of Two Novel 14-Epivitamin D3 Analogs With Vitamin D3 Receptor-Retinoid X Receptor Heterodimers on Vitamin D3 Response Elements", Journal of Bone and Mineral Research, 16(4): 625-638, 2001.
Verneris et al. "The Phenotypic and Functional Characteristics of Umbilical Cord Blood and Peripheral Blood Natural Killer Cells", British Journal of Haematology, BJH, 147: 185-191, 2009.
Verneris et al. "The Phenotypic and Functional Characteristics of Umbilical Cord Blood and Peripheral Blood Natural Killer Cells", British Journal of Haematology, XP009146910, 147(2): 185-191, Oct. 2009.
Vilensky et al. "British Anti-Lewisite (Dimercaprol): An Amazing History", Annals of Emergency Medicine, 41(3): 378-383, 2003. Abstract.
Vir?g et al. "The Therapeutic Potential of Poly(ADP-Ribose) Polymerase Inhbititors", Pharmacological Reviews, 54(3): 375-429, 2002.
Vlahos et al. "A Specific Inhibitor of Phosphatidylinositol 3-Kinase 2-(4-Morpholinyl)-8 Phenyl-4H-1-Benzopyran-4-One (LY294002)", Journal of Biological Chemistry, 269(7): 5241-5248, Feb. 18, 1994.
Von Drygalski et al. "Murine Bone Marrow Cells Cultured Ex Vivo in the Presence of Multiple Cytokine Combinations Lose Radioprotective and Long-Term Engraftment Potential", Stem Cells and Development, 13: 101-111, 2004.
Wagers et al. "Little Evidence for Developmental Plasticity of Adult Hematopoietic Stem Cells", Science, 297(5590): 2256-2259, Sep. 27, 2002. Abstract.
Wall et al. "Inhibition of the Intrinsic NAD+ Glycohydrolase Activity of CD38 by Carbocyclic NAD Analogues", Biochemical Journal, 335(3): 631-636, 1998.
Walton et al. "Prediction of Antisense Oligonucleotide Binding Affinity to a Structured RNA Target", Biotechnology and Bioengineering, 65(1): 1-9, 1999.
Wang et al. "In Vitro Culture of Umbilical Cord Blood MNC and CD34+ Selected Cells", Sheng Wu Gong Cheng Xue Bao, 18(3): 343-347, 2002. Abstract.
Wang et al. "PH-Sensitive Immunoliposomes Mediate Target-Cell-Specific Delivery and Controlled Expression of a Foreign Gene in Mouse", Proc. Natl. Acad. Sci. USA, 84: 7851-7855, Nov. 1987.
Wasa et al. "Copper Deficiency With Pancytopenia During Total Parenteral Nutrition", Journal of Parenteral and Enteral Nutrition, 18(2): 190-192, 1994.
Weissmann "Translating Stem and Progenitor Cell Biology to the Clinic: Barriers and Opportunities", Science, 287(5457): 1442-1446, Feb. 25, 2000.
Wendling et al. "Retinoid X Receptor Are Essential for Early Mouse Development and Placentogenesis", Proc. Natl. Acad. Sci. USA, 96(2): 547-551, Jan. 19, 1999.
Whitlow et al. "Single-Chain Fv Proteins and Their Fusion Proteins", Methods: A Companion to Methods in Enzymology, 2(2): 97-105, Apr. 1991.

(56) References Cited

OTHER PUBLICATIONS

Wick et al. "New Ways in Hepatocyte Cultures: Cell Immobilisation Technique", ALTEX (Alternative zu Tierexperimenten), 14(2): 51-56, 1997. Abstract.

Williams et al. "Selection and Expansion of Peripheral Blood CD34+ Cells in Autologous Stem Cell Transplantation for Breast Cancer", Blood, 87(5): 1687-1691, 1996.

Wilson et al. "Hepatocyte-Directed Gene Transfer In Vivo Leads to Transient Improvement of Hypercholesterolentia in Low Density Lipoprotein Receptor-Deficient Rabbits", The Journal of Biological Chemistry, 267(2): 963-967, Jan. 15, 1992.

Wilson et al. "Retrovirus-Mediated Transduction of Adult Hepatocytes", Proc. Natl. Acad. Sci. USA, 85: 3014-3018, May 1988.

Wolff et al. "Direct Gene Transfer Into Mouse Muscle In Vivo", Science, 247: 1465-1468, Mar. 23, 1990.

Wondisford et al. "Cloning of the Human Thyrotropin ?-Subunit Gene and Transient Expression of Biologically Active Human Thyrotropin After Gene Transfection", Molecular Endocrinology, 2: 32-39, 1988.

Wu et al. "Receptor-Mediated Gene Delivery and Expression In Vivo", The Journal of Biological Chemistry, 263(29): 14621-14624, Oct. 15, 1988.

Wulf et al. "Somatic Stem Cell Plasticity: Current Evidence and Emerging Concepts", Experimental Hematology, 29: 1361-1370, 2001.

Xia et al. "Surface Fucosylation of Human Cord Blood Cells Augments Binding to P-Selectin and E-Selectin and Enhances Engraftment in Bone Marrow", Blood, XP002429129, 104(10): 3091-3096, Nov. 15, 2004.

Yang et al. "In Vitro Trans-Differentiation of Adult Hepatic Stem Cells Into Pancreatic Encocrine Hormone-Producing Cells", Proc. Natl. Acad. Sci. USA, 99(12): 8078-8083, 2002.

Yang et al. "Mesenchymal Stem/Progenitor Cells Developed in Cultures From UC Blood", Cythotherapy, 6(5): 476-486, 2004.

Yau et al. "Endogenous Mono-ADP-Ribosylation Mediates Smooth Muscle Cell Proliferation and Migration Via Protein Kinase Induction of C-Fos Expression", European Journal of Biochemistry, 270: 101-110, 2003.

Yin et al. "AC133, A Novel Marker for Human Hematopoietic Stem and Progenitor Cells", Blood, 90(12): 5002-5012, Dec. 15, 1997.

Yla-Herttuala et al. "Gene Transfer As a Tool to Induce Therapeutic Vascular Growth", Nature Medicine, 9(6): 694-701, 2003.

Yoon et al. "Clonally Expanded Novel Multipotent Stem Cells From Human Bone Marrow Regenerate Myocardium After Myocardial Infarction", The Journal of Clinical Investigation, 115(2): 326-338, Feb. 2005.

Yu et al. "CD94 Surface Density Identifies a Functional Intermediary Between the CD56[Bright] and CD56[Dim] Human NK-Cell Subsets", Blood, 115(2): 274-281, Jan. 14, 2010.

Zhang et al. "Flavonoids as Aryl Hydrocarbon Receptor Agonists/Antagonists: Effect of Structure and Cell Context", Environmental Health Perspectives, 111(16): 1877-1882, Dec. 2003.

Zhang et al. "Human Placenta-Derived Mesenchymal Progenitor Cells Support Culture Expansion of Long-Term Culture-Initiating Cells From Cord Blood CD34+ Cells", Experimental Hematology, 32: 657-664, Jul. 2004.

Zidar et al. "Observations on the Anemia and Neutropenia of Human Copper Deficiency", American Journal of Hematology, 3: 177-185, 1977.

Zimmerman et al. "Large-Scale Selection of CD34+ Peripheral Blood Progenitors and Expansion of Neutrophil Precursors for Clinical Applications", Journal of Hematotherapy, 5: 247-253, 1996.

Zocchi et al. "Ligand-Induced Internalization of CD38 Results in Intracellular Ca2+ Moblization: Role of NAD+ Transport Across Cell Membranes", The FASEB Journal, 13(2): 273-283, 1999.

Zon et al. "Developmental Biology of Hematopoiesis", Blood, 86(8): 2876-2891, 1995.

Zucchini et al. "Natural Killer Cells in Immunodefense Against Infective Agents", Expert Reviews of Anti-Infective Therapy, 6(6): 867-885, Dec. 2008.

Zulewski et al. "Multipotential Nestin-Positive Stem Cells Isolated From Adult Pancreatic Islets Differentiate Ex Vivo Into Pancreatic Endocrine, Exocrine, and Hepatic Phenotypes", Diabetes, 50: 521-533, 2001.

DOD "Tetraethylene Pentamine DOD Hazardous Material Information", 6810-00f017710, 1991.

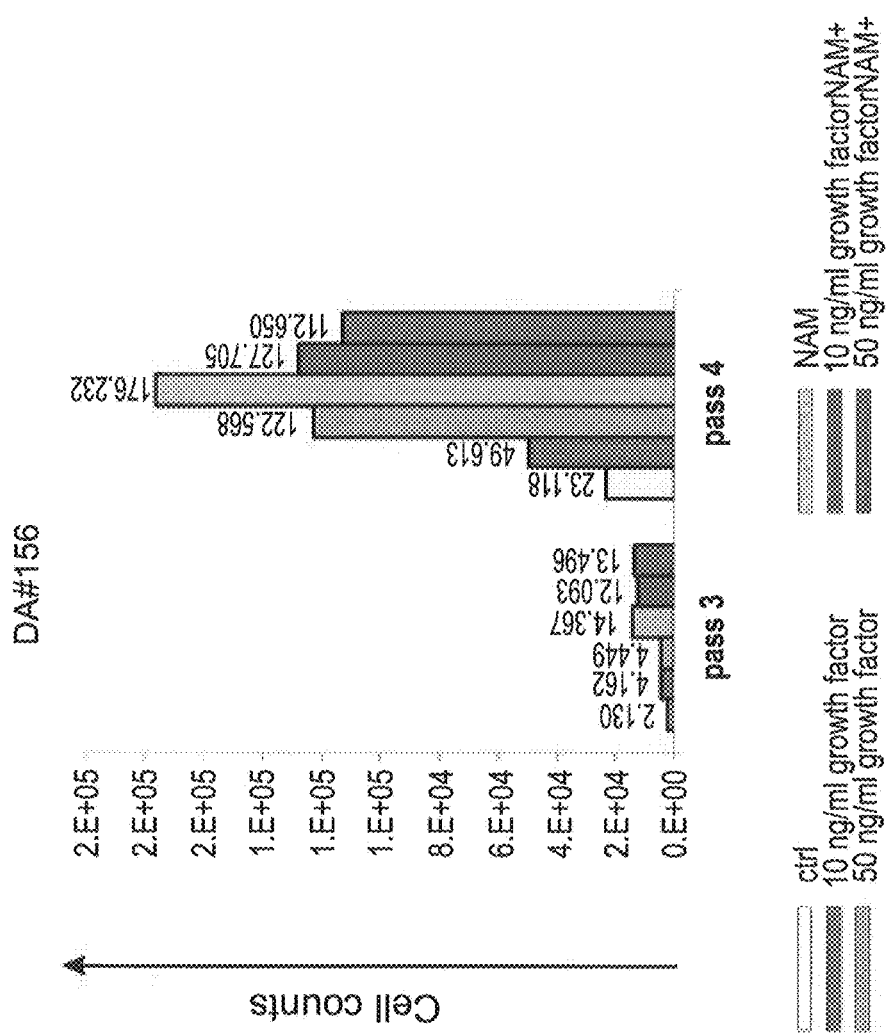

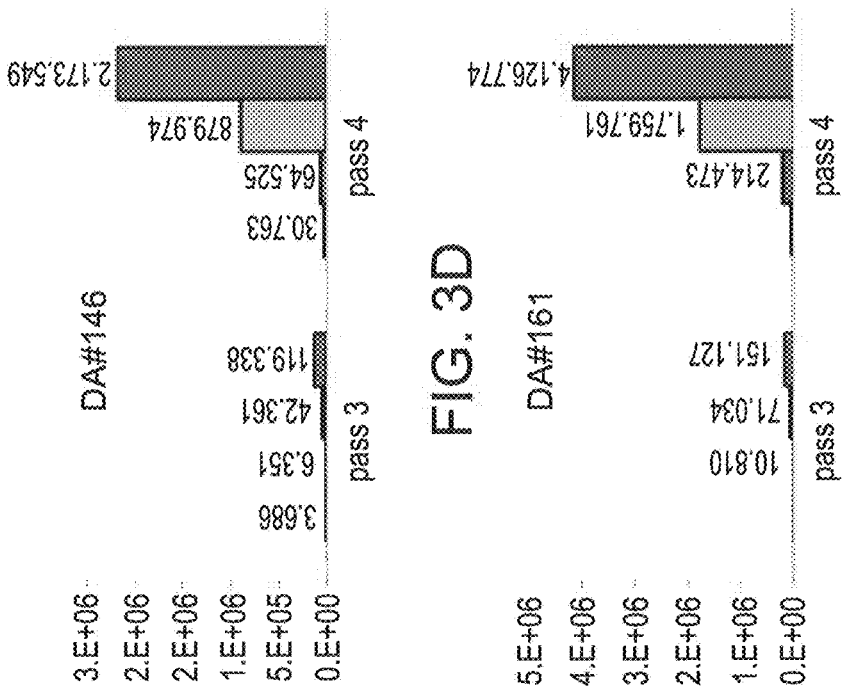
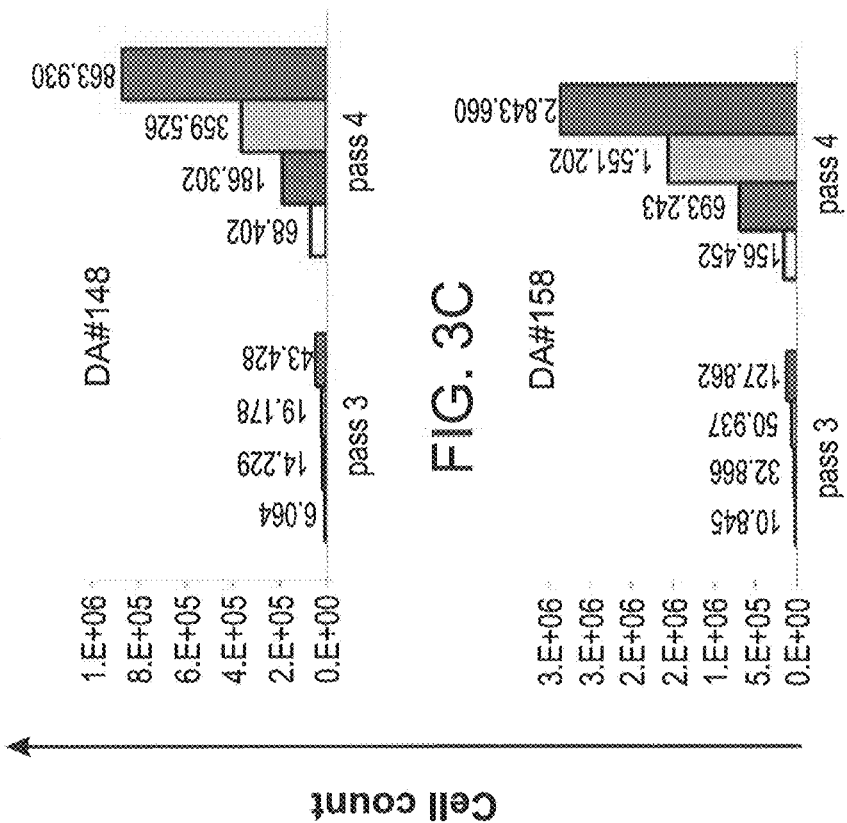

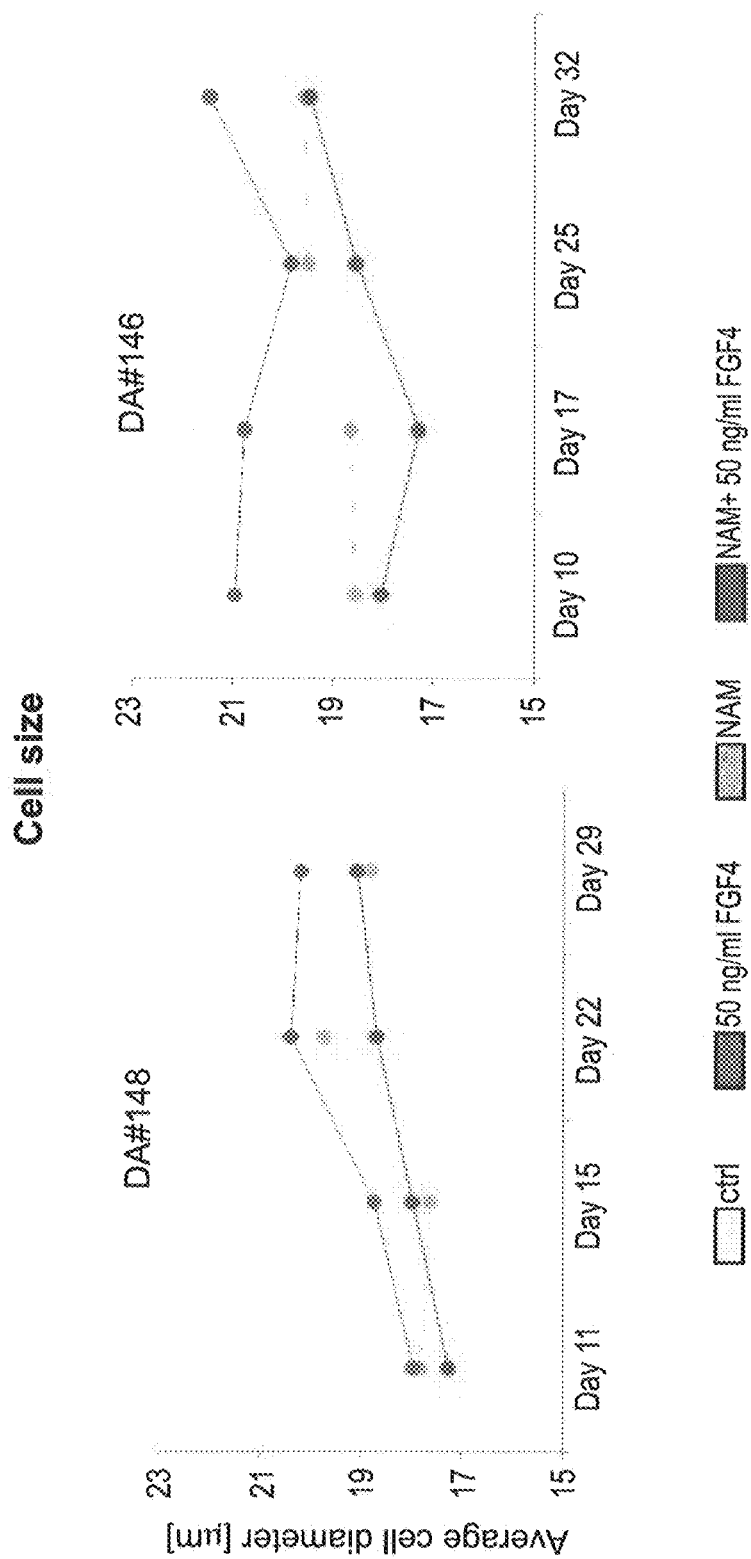

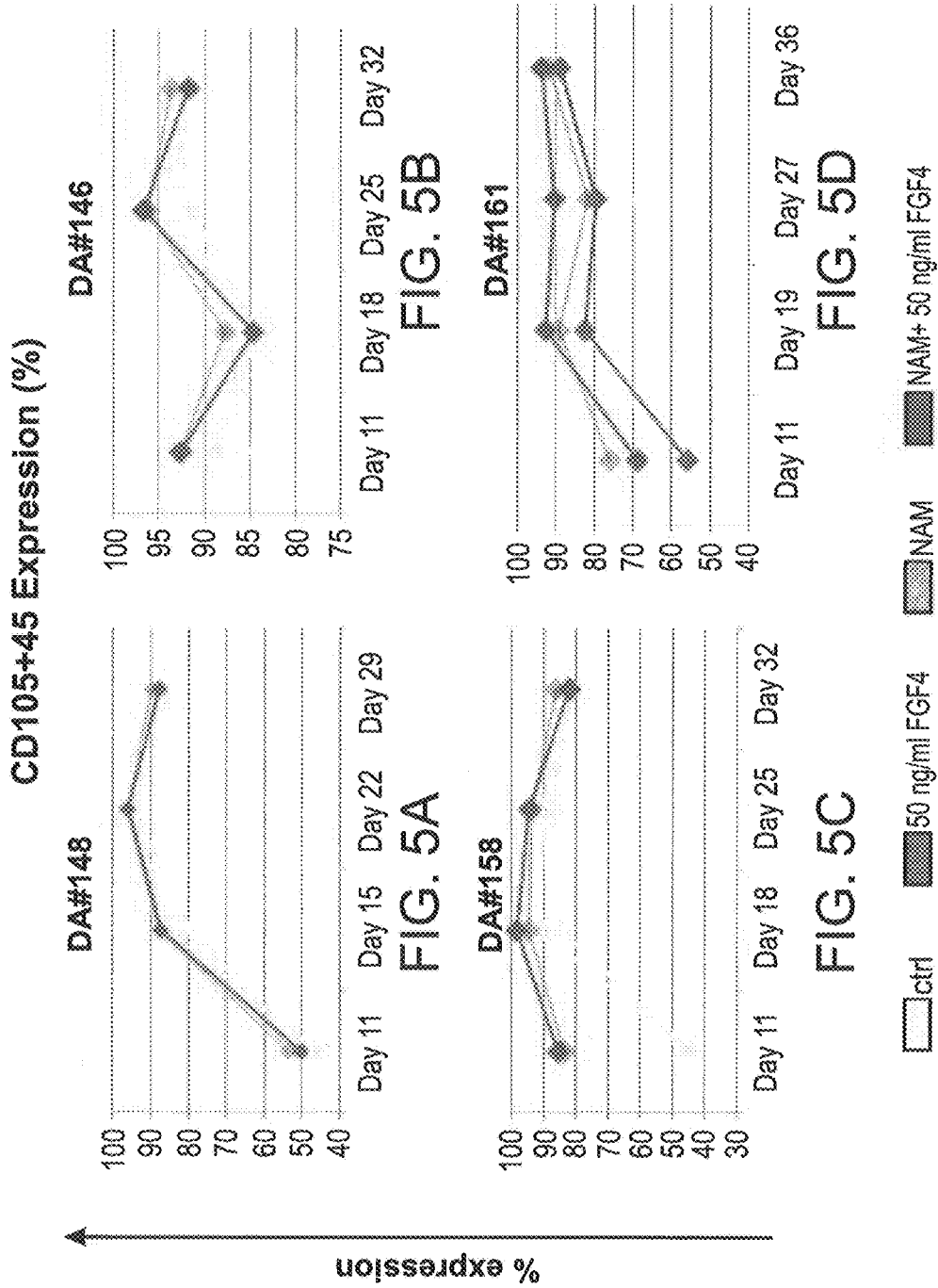

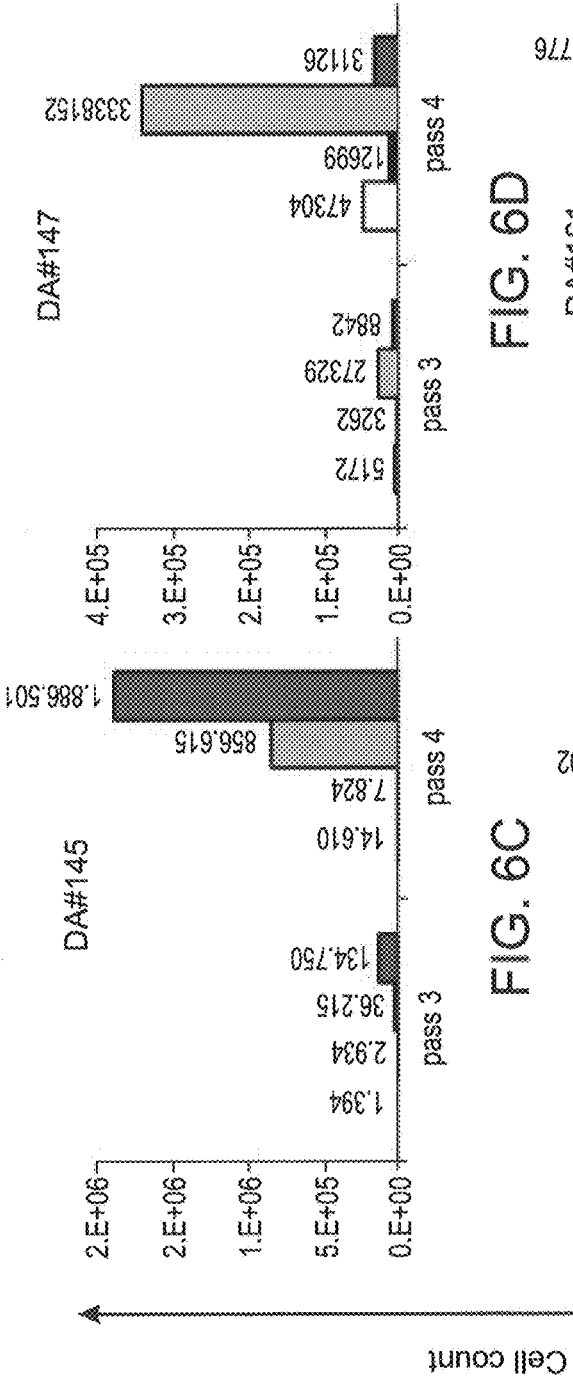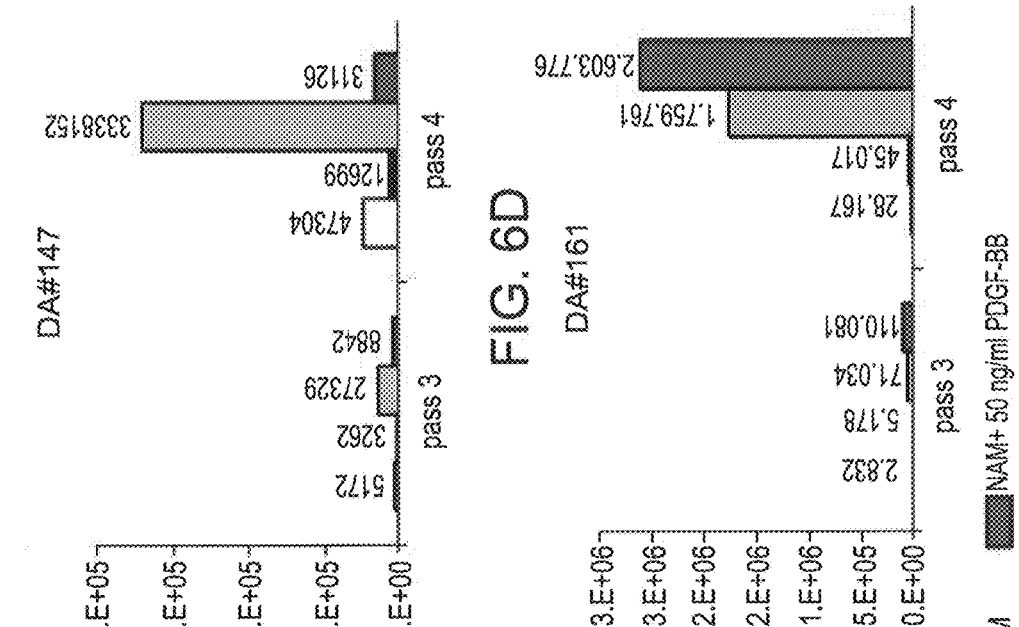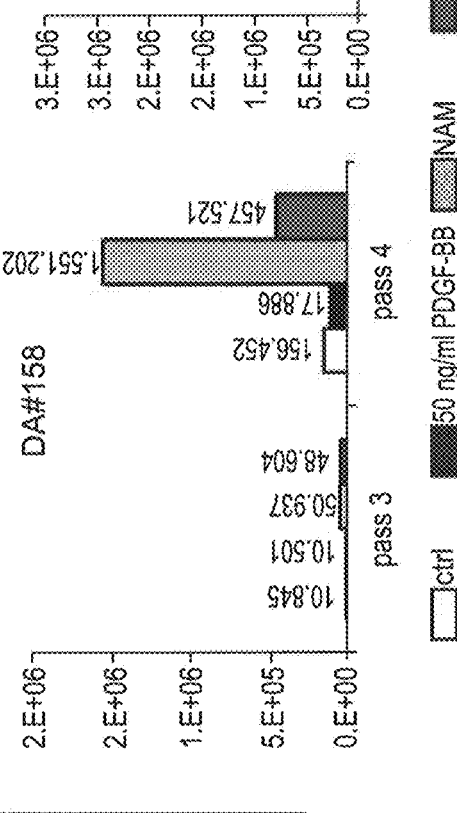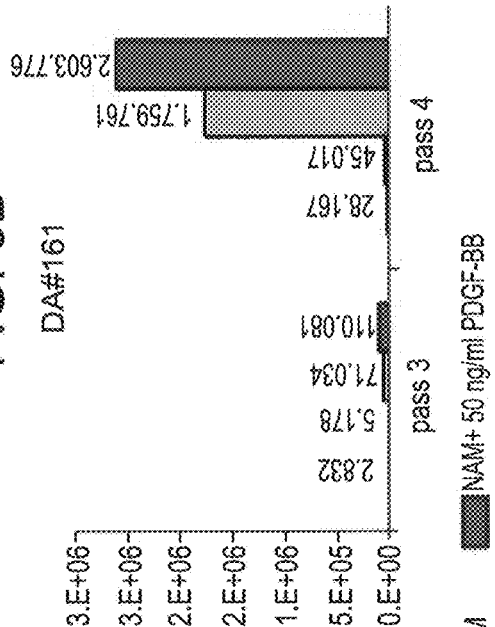

DA#145

DA#147

DA#158

DA#161

□ ctrl  ▨ 50 ng/ml PDGF-BB  ▨ NAM  ▨ NAM+ 50 ng/ml PDGF-BB

% expression

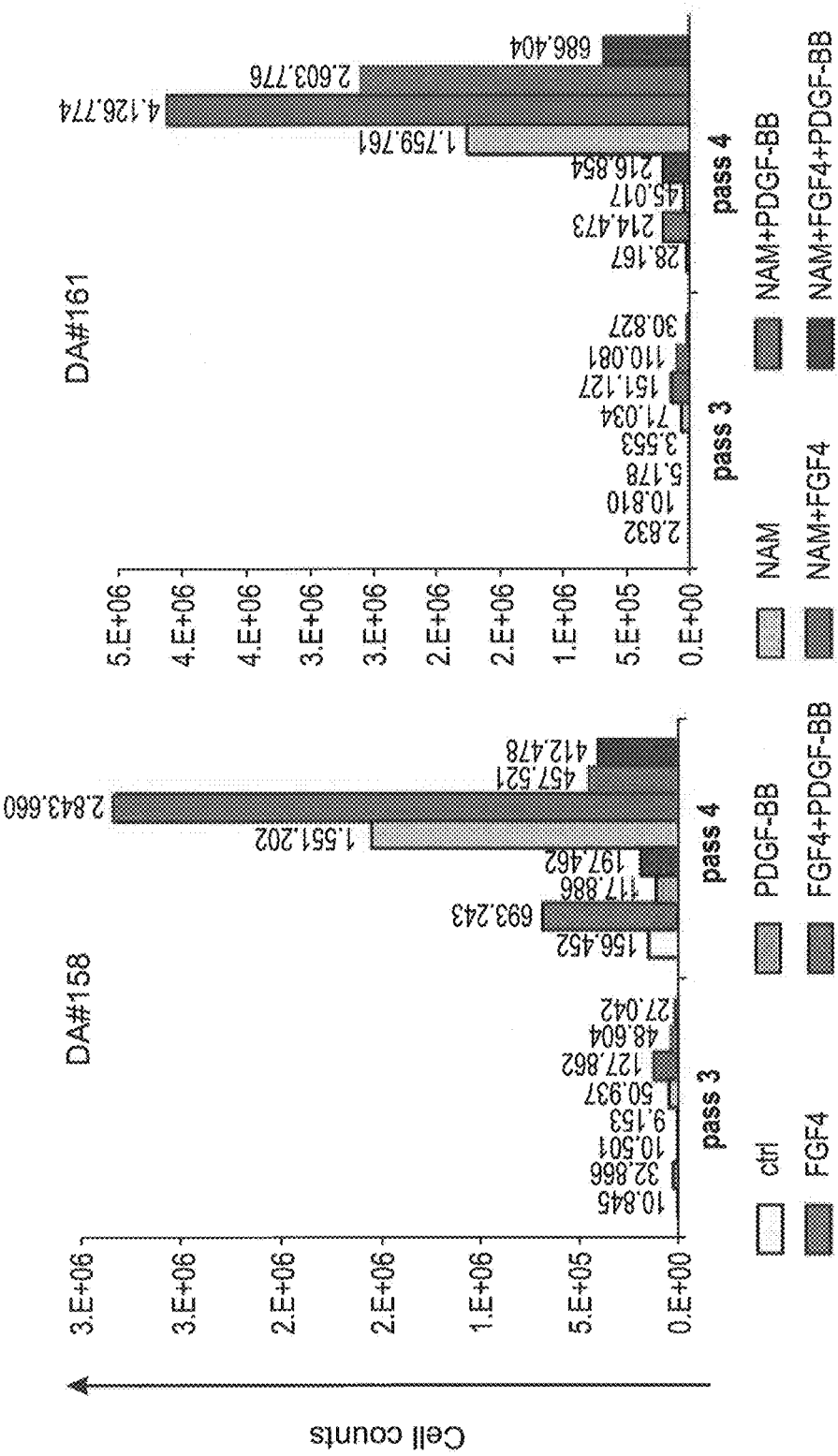

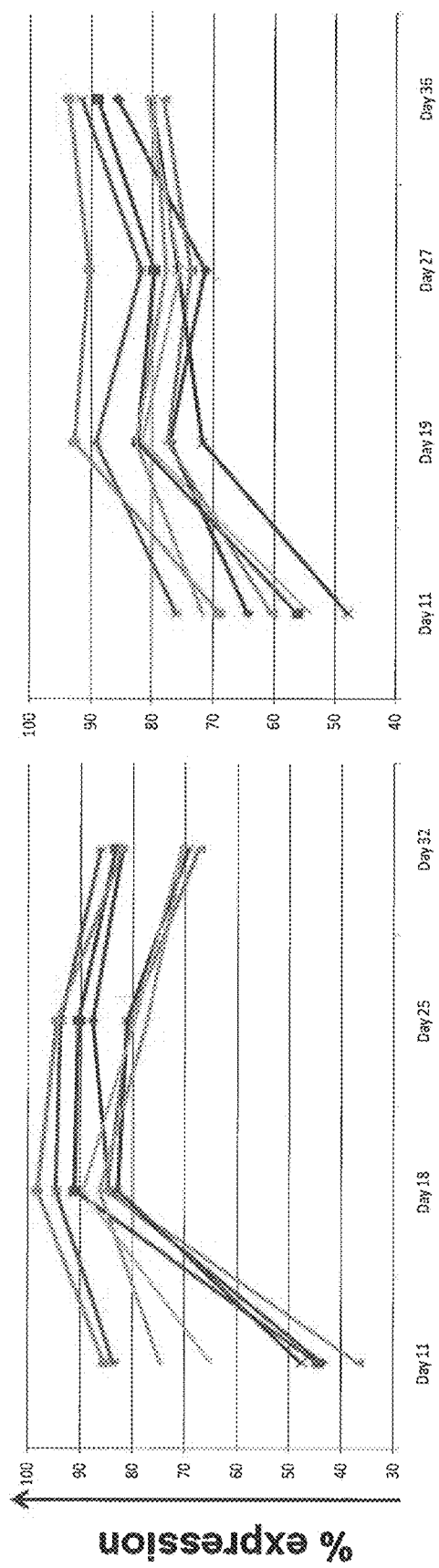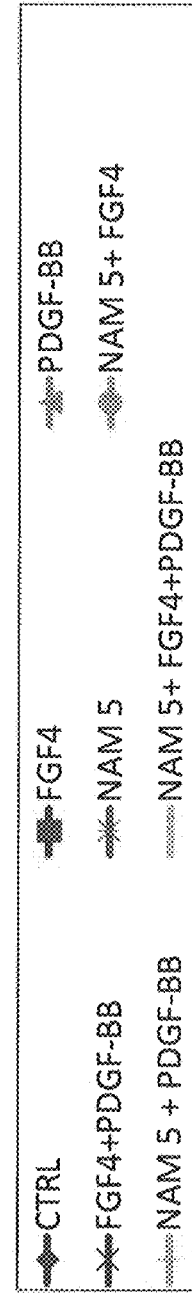
FIG. 9A
FIG. 9B

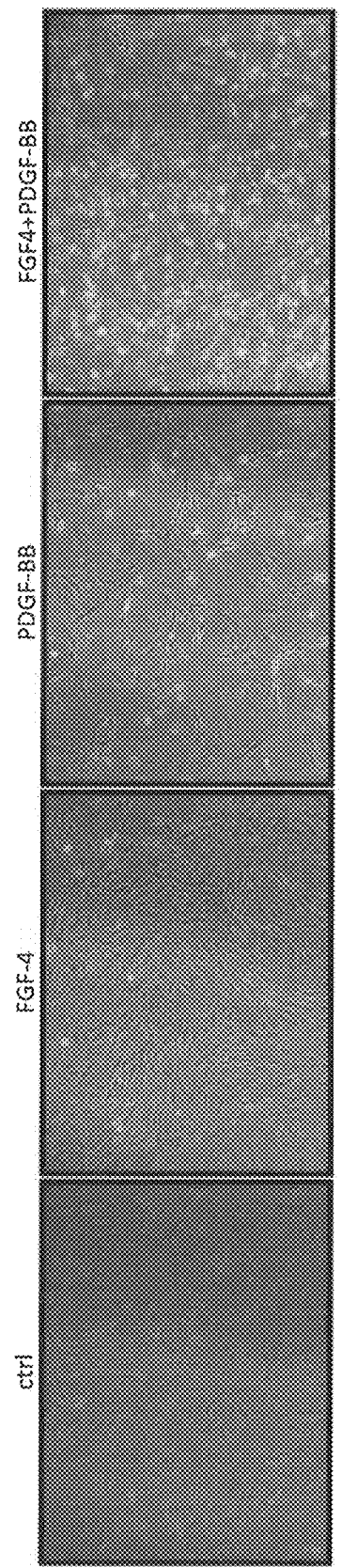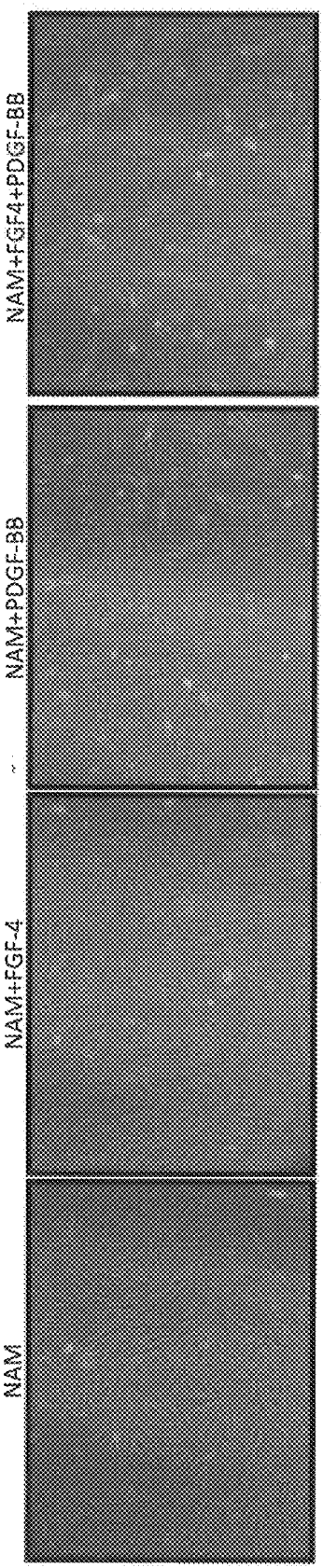

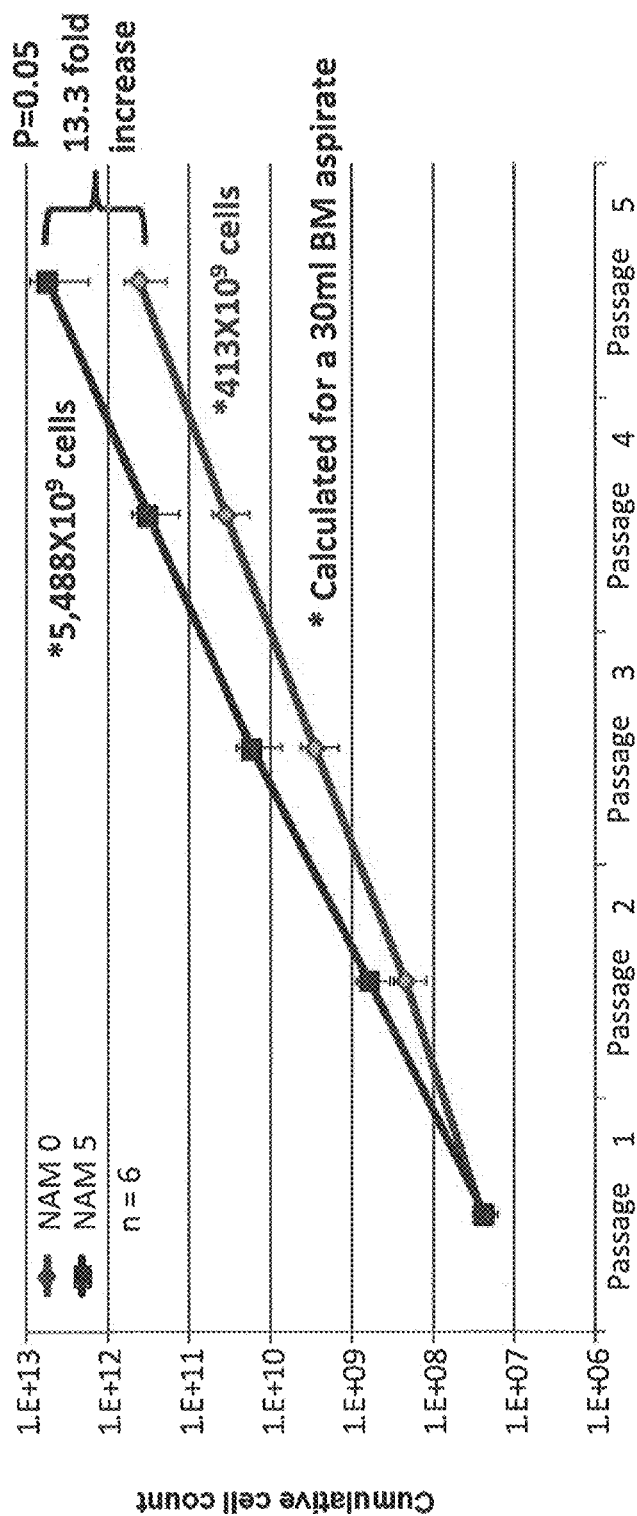

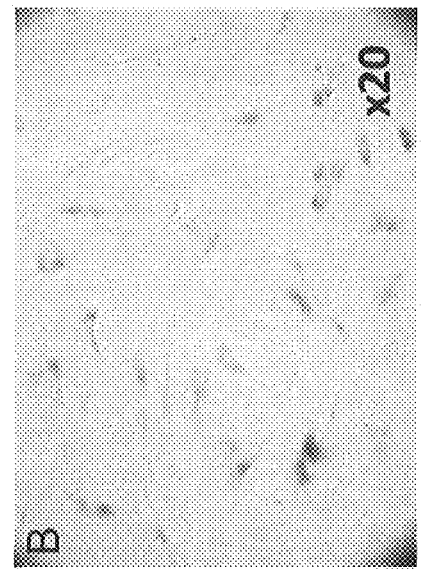
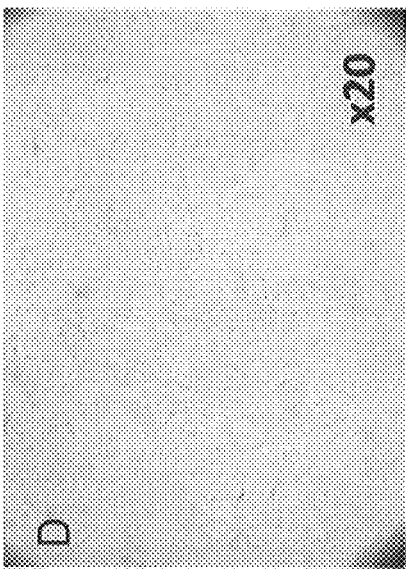
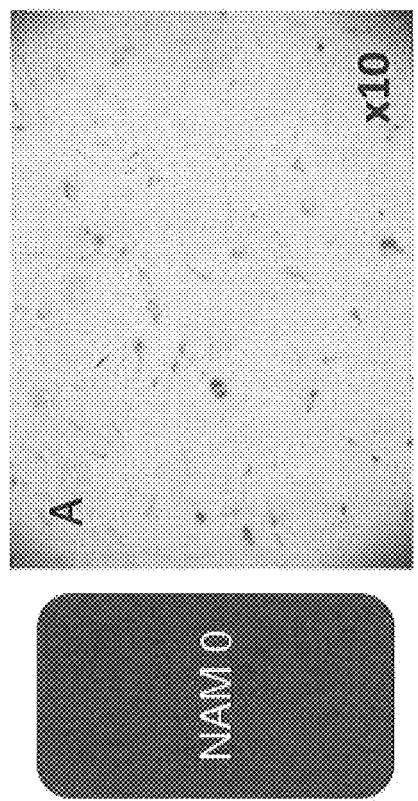
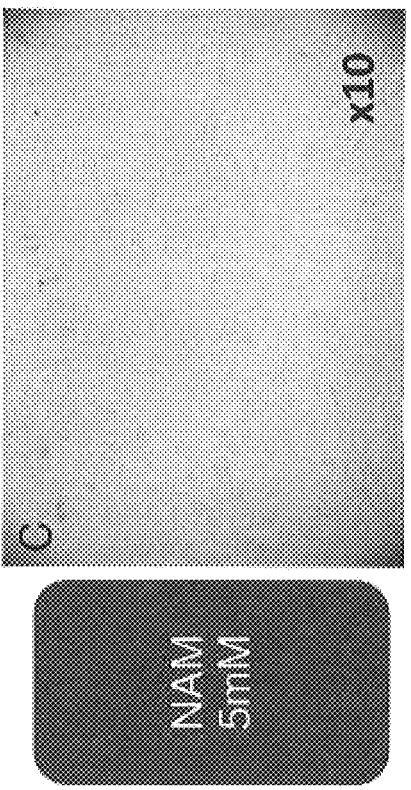
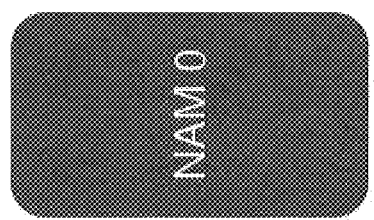
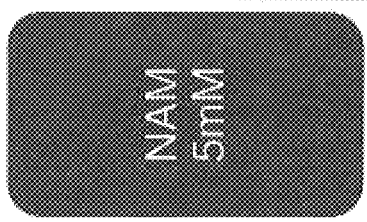
FIG. 23A  FIG. 23B  FIG. 23C  FIG. 23D

NAM 0

NAM 5

The influence of FGF4 on ex-vivo expanded CD133+ cells differentiation

The influence of FGF4 on ex-vivo expanded CD133+ cells differentiation

The influence of FGF4 on ex-vivo expanded CD133+ cells differentiation

The influence of FGF4 on ex-vivo expanded CD133+ cells differentiation

CULTURING OF MESENCHYMAL STEM CELLS WITH FGF4 AND NICOTINAMIDE

This application is a national stage application, filed under 35 U.S.C. § 371, of International Application No. PCT/IL2013/050136, filed Feb. 13, 2013, which claims priority to and benefit of provisional application U.S. Ser. No. 61/597,899 filed on Feb. 13, 2012, and provisional application U.S. Ser. No. 61/597,909 filed on Feb. 13, 2012, the contents of which are herein incorporated by reference in their entireties.

FIELD AND BACKGROUND OF THE INVENTION

The present invention, in some embodiments thereof, relates to methods of expanding mesenchymal stem cells and cell populations generated thereby.

Mesenchymal stem cells (MSCs) are non-hematopoietic cells that are capable of differentiating into specific types of mesenchymal or connective tissues including adipose, osseous, cartilaginous, elastic, neuronal, hepatic, pancreatic, muscular, and fibrous connective tissues. The specific differentiation pathway which these cells enter depends upon various influences from mechanical influences and/or endogenous bioactive factors, such as growth factors, cytokines, and/or local microenvironmental conditions established by host tissues.

MSCs reside in a diverse host of tissues throughout the adult organism and possess the ability to 'regenerate' cell types specific for these tissues. Examples of these tissues include adipose tissue, umbilical cord blood, periosteum, synovial membrane, muscle, dermis, pericytes, blood, bone marrow and trabecular bone.

The multipotent character of mesenchymal stem cells make these cells an attractive therapeutic tool and candidate for transplantation, capable of playing a role in a wide range of clinical applications in the context of both cell and gene therapy strategies. Mesenchymal cells may be used to enhance hematopoietic engraftment post-transplantation, to correct inherited and acquired disorders of bone and cartilage, for implantation of prosthetic devices in connective and skeletal tissue, and as vehicles for gene therapy.

In culture, expanded MSC express a panel of key markers including CD105 (endoglin, SH2), CD73 (ecto-5' nucleotidase, SH3, SH4), CD166 (ALCAM), CD29 ($\beta$1-integrin), CD44 (H-CAM), and CD90 (Thy-1). In contrast to hematopoietic stem cells they lack CD45, CD34 and CD133 expression.

MSC can be identified by their ability to form colony forming units-fibroblast (CFU-F) in vitro. However, these cells are heterogeneous with respect to their proliferation and differentiation capacity. At least two morphologically distinct MSC populations have been identified that differ not only in size but also in their cell division rate and differentiation capacity. In addition, analysis of single cell-derived MSC colonies from adult bone marrow revealed differential capacity of colonies to undergo osteogenic, adipogenic, and chondrogenic differentiation.

In most cases, unfractionated bone marrow-derived cells are used as the starting population for the culture of MSC. This isolation method relies on the adherence of fibroblast-like cells to a plastic surface and the removal of non-adherent hematopoietic cells. The resulting cells are poorly defined and give rise not only to heterogeneous MSC populations but also to osteoblasts and/or osteoprogenitor cells, fat cells, reticular cells, macrophages, and endothelial cells. To define the starting population more precisely, surface markers such as SH2 (CD105), SH3/SH4 (CD73), SSEA-4 and the low affinity nerve growth factor receptor (CD271), which enrich for MSC, have been employed [Simmons P. J et al. (1991) Blood 78:55-62; Conconi M T et al., (2006) Int J Mol Med 18:1089-96; Gang E J et al., (2007) Blood 109:1743-51; Liu P G, (2005); Zhongguo Shi Yan Xue Ye Xue Za Zhi 13:656-9; Quirici N, et al., (2002) Exp. Hematol 30:783-91].

Another example of a cell surface antigen which has been targeting for isolating homogeneous populations of mesenchymal stem cells is stromal precursor antigen-1 (STRO-1). The STRO-1 antigen is expressed on the surface of approximately 10-20% of adult human BM that includes all CFU-F, Glycophorin-A nucleated red cells, and a small subset of CD19 B-cells, but is not expressed on hematopoietic stem and progenitor cells (HSC) (Simmons and Torok-Storb, 1991). STRO-1 is widely regarded as a marker of early mesenchymal/stromal precursor cells, because it has been strongly linked to mesenchymal cell clonogenicity, plasticity, and other progenitor cell characteristics [Psaltis et al., (2010), Journal of Cellular Physiology, 530-540]. High co-expression of STRO-1 (STRO-1Bright) with other surface markers, such as CD106, CD49a, CD146 or STRO-3 has been shown to greatly increase the cloning efficiency of BM MNC (Gronthos et al., 2008, Methods Molecular Biology, 449:45-57]. Freshly isolated STRO-1$^{Bright}$ BM MNC also possess other hallmark features characteristic of multipotent stem cells, including in vivo quiescence, high telomerase activity, and an undifferentiated phenotype. Moreover, this population of cells lacks hematopoietic stem cell (CD34), leukocyte (CD45), and erythroid (Glycophorin-A) associated markers.

More recently, platelet derived growth factor receptor-$\beta$ (PDGF-RB; CD140b) was identified as a selective marker for the isolation of clonogenic MSC [Buhring H J, (2007) Ann N Y Acad Sci 1106:262-71]. Other reports demonstrated a 9.5-fold enrichment of MSC in bone marrow cells with prominent aldehyde dehydrogenase activity [Gentry T et al., (2007) Cytotherapy 9:259-74].

Even though MSCs multiply relatively easily in vitro, their proliferative potential and their stem cell characteristics are continuously decreased during prolonged culture. For example, it has been shown that expansion in culture leads to premature senescence (the process of aging characterized by continuous morphological and functional changes). Cells became much larger with irregular and flat shape and the cytoplasm became more granular. These senescence-associated effects are continuously acquired from the onset of in vitro culture (PLoS ONE, May 2008|Volume 3|Issue 5|e2213). As a result, the successful manufacturing for commercialization of large batches from one donor of homogenous MSCs that preserve their characteristics following expansion in culture remains a challenge.

Due to the low or absent expression of MHC molecules, especially class II on mesenchymal stem cells, these cells may be considered immune privileged, thus paving the way for allogeneic transplantation of such cells for the treatment of a wide range of disorders. Accordingly, improved methods of expanding banks of mesenchymal stem cells have become an important factor for commercializing their use.

The role of growth factors in increasing proliferation and survival in MSCs has been widely studied over the past few years and many factors have been proposed for increasing the expansion efficiency of these cells.

For example, many protocols relating to the expansion of MSCs include culturing in the presence of basic fibroblast growth factor (b-FGF) (Vet Res Commun. 2009 December; 33(8):811-21). It has been shown that b-FGF not only maintains MSC proliferation potential, it also retains osteogenic, adipogenic and chondrogenic differentiation potentials through the early mitogenic cycles.

Vascular endothelial growth factor (VEGF) has also been shown to increase MSC proliferation [Pons et al., Biochem Biophys Res Commun 2008, 376:419-422].

Exogenous addition of Hepatocyte growth factor (HGF) to MSC populations has been shown to affect proliferation, migration and differentiation (Furge et al., Oncogene 2000, 19:5582-5589].

Another proposed growth factor for increasing the expansion of MSCs is Platelet derived growth factor (PDGF) shown to be a potent mitogen of MSCs [Kang et al., J Cell Biochem 2005, 95:1135-1145].

Epidermal growth factor (EGF) and heparin-binding EGF have both been shown to promote ex vivo expansion of MSCs without triggering differentiation into any specific lineage [Tamama et al., Stem Cells 2006, 24:686-695; Krampera et al., Blood 2005, 106:59-66]. In addition to its mitogenic effect on MSCs, EGF also increases the number of colony-forming units by 25% [Tamama et al., J Biomed Biotechnol 2010, 795385].

Other have suggested the use of Wnt signalling agonists for expanding MSCs based on experiments which study Wnt signaling proliferation in MSCs. Canonical Wnt signalling was shown to maintain stem cells in an undifferentiated but self-renewing state. Addition of Wnt3a by activating the canonical Wnt pathway increased both proliferation and survival while preventing differentiation into the osteoblastic lineage in MSCs [Boland et al., J Cell Biochem 2004, 93:1210-1230].

The choice of growth factors to be used on MSCs was initially determined based on previously existing knowledge about the effect of a particular growth factor on cell morphogenesis. This was done with the dual pursuit of expanding MSCs and causing them to differentiate into the lineage that it was known to favor. Transforming growth factor beta (TGFβ), for example, is known to influence cells from the chondrogenic lineage in vivo, promoting initial stages of mesenchymal condensation, prechondrocyte proliferation, production of extracellular matrix and cartilage-specific molecule deposition, while inhibiting terminal differentiation. When applied to MSCs, cells show increased proliferation and a bias towards the chondrogenic lineage [Bonewald et al., J Cell Biochem 1994, 55:350-357; Longobardi L, J Bone Miner Res 2006, 21:626-636.

BMP-3, another member of the transforming growth factor beta family, known to enhance bone differentiation was shown to increase MSC proliferation threefold [Stewart A et al., Cell Physiol 2010, 223:658-666].

Nicotinamide (NA), the amide form of niacin (vitamin B3), is a base-exchange substrate and a potent inhibitor of NAD(+)-dependent enzymes endowed with mono- and poly-ADP-ribosyltransferase activities. ADP-ribosylation is implicated in the modification of a diverse array of biological processes (Corda D, Di Girolamo M. 2003; 22(9):1953-1958; Rankin P W, et al., J Biol Chem. 1989; 264:4312-4317; Banasik M. et al., J Biol Chem. 1992; 267:1569-1575; Ueda K, Hayaishi O, Annu Rev Biochem. 1985; 54:73-100; Smith S. Trends Biochem Sci. 2001; 26:174-179; Virág L, Szabó C. Pharm. Reviews. 2002; 54:375-429).

WO 07/063545 discloses the use of nicotinamide for the expansion of hematopoietic stem and/or progenitor cell populations.

WO 03/062369 discloses the use of nicotinamide, and other inhibitors of CD38, for the inhibition of differentiation in ex-vivo expanding stem and progenitor cells. However, WO 03/062369 does not teach administration of nicotinamide for particular time intervals.

U.S. Patent Application No. 20050260748 teaches isolation and expansion of mesenchymal stem cells with nicotinamide in the presence of a low calcium concentration.

Additional background art includes Farre et al., Growth Factors, 2007 April; 25(2):71-6.

SUMMARY OF THE INVENTION

According to an aspect of some embodiments of the present invention there is provided a method of culturing mesenchymal stem cells (MSCs) comprising culturing a population of the MSCs in a medium comprising nicotinamide and fibroblast growth factor 4 (FGF4), thereby culturing MSCs.

According to an aspect of some embodiments of the present invention there is provided a method of expanding a population of mesenchymal stem cells, the method comprising culturing a seeded population of mesenchymal stem cells for a period of time sufficient for cell expansion, wherein for at least a portion of the period of time the culturing is effected in a medium devoid of nicotinamide; and for at least a second portion of the period of time, the culturing is effected in a medium comprising nicotinamide and FGF4, thereby generating an expanded population of mesenchymal stem cells.

According to an aspect of some embodiments of the present invention there is provided a method of generating cells useful for transplantation into a subject, the method comprising:

(a) culturing mesenchymal stem cells according to the methods described herein to generate a population of cultured mesenchymal stem cells;

(b) contacting the population of cultured mesenchymal stem cells with a differentiating agent, thereby generating cells useful for transplantation into a subject.

According to an aspect of some embodiments of the present invention there is provided a method of generating cells useful for transplantation, the method comprising:

(a) expanding mesenchymal stem cells according to the methods described herein; and (b) contacting the mesenchymal stem cells with a differentiating agent, thereby generating cells useful for transplantation.

According to an aspect of some embodiments of the present invention there is provided an isolated population of mesenchymal stem cells generated according to the methods described herein.

An isolated population of differentiated cells generated according to the methods described herein.

According to an aspect of some embodiments of the present invention there is provided a method of treating a disease or disorder, the method comprising transplanting to a subject in need thereof a therapeutically effective amount of the isolated population of cells described herein, thereby treating the disease or disorder.

According to an aspect of some embodiments of the present invention there is provided a cell culture comprising mesenchymal stem cells and a medium which comprises nicotinamide and FGF4.

According to some embodiments of the invention, the medium comprises DMEM.

According to some embodiments of the invention, the medium comprises serum or platelet lysate.

According to some embodiments of the invention, the mesenchymal stem cells are derived from a tissue selected from the group consisting of bone marrow, adipose tissue, placenta and umbilical cord blood.

According to some embodiments of the invention, the nicotinamide is selected from the group consisting of nicotinamide, a nicotinamide analog, a nicotinamide metabolite, a nicotinamide analog metabolite and derivatives thereof.

According to some embodiments of the invention, the culturing is effected on a plastic surface.

According to some embodiments of the invention, the population of MSCs is comprised in a heterogeneous population of cells.

According to some embodiments of the invention, at least 70% of the heterogeneous population of cells are MSCs.

According to some embodiments of the invention, the calcium concentration of the medium is greater than 1.8 mM.

According to some embodiments of the invention, the culturing is effected for at least 1 week.

According to some embodiments of the invention, the culturing is effected for at least 3 passages.

According to some embodiments of the invention, the concentration of the nicotinamide is 1-20 mM.

According to some embodiments of the invention, the medium is devoid of platelet derived growth factor (PDGF).

According to some embodiments of the invention, the expanding is effected under conditions that do not induce differentiation of the mesenchymal stem cells.

According to some embodiments of the invention, the seeded population of mesenchymal stem cells were seeded in an absence of nicotinamide.

According to some embodiments of the invention, the seeded population of mesenchymal stem cells were seeded in a presence of nicotinamide.

According to some embodiments of the invention, the medium is devoid of platelet derived growth factor (PDGF).

According to some embodiments of the invention, the medium devoid of nicotinamide is devoid of FGF4.

According to some embodiments of the invention, the medium devoid of nicotinamide comprises FGF4

According to some embodiments of the invention, the culturing in the medium comprising nicotinamide is effected prior to the culturing in the medium devoid of nicotinamide.

According to some embodiments of the invention, the culturing in the medium devoid of the nicotinamide is effected prior to the culturing in the medium comprising nicotinamide.

According to some embodiments of the invention, the culturing in the medium comprising nicotinamide is effected for at least one day.

According to some embodiments of the invention, the culturing in the medium comprising nicotinamide is effected for at least one week.

According to some embodiments of the invention, the culturing in the medium devoid of nicotinamide is effected for at least one day.

According to some embodiments of the invention, the culturing in the medium devoid of nicotinamide is effected for at least one week.

According to some embodiments of the invention, the culturing in the medium comprising nicotinamide is effected in a medium comprising calcium, wherein a concentration of the calcium is greater than 1.8 mM.

According to some embodiments of the invention, the culturing in the medium devoid of nicotinamide is effected in a medium comprising calcium, wherein a concentration of the calcium is greater than 1.8 mM.

According to some embodiments of the invention, the differentiation agent comprises a growth factor.

According to some embodiments of the invention, the differentiation agent comprises a polynucleotide which encodes the differentiation agent.

According to some embodiments of the invention, the polynucleotide encodes bone morphogenic protein 2 (BMP2).

According to some embodiments of the invention, the isolated population of mesenchymal stem cells is substantially homogeneous.

According to some embodiments of the invention, at least 40% of the cells express VCAM1/CD106.

According to some embodiments of the invention, at least 90% of the cells have a diameter less than 20 μm.

According to some embodiments of the invention, the isolated population of mesenchymal stem cells are less granular than mesenchymal stem cells generated under identical conditions but in an absence of nicotinamide.

According to some embodiments of the invention, less than 30% of the cells express CD45, more than 95% of the cells express CD90 and more than 90% of the cells express CD105 and CD44.

According to some embodiments of the invention, the disease or disorder is selected from the group consisting of a bone or cartilage disease, a neurodegenerative disease, a cardiac disease, a hepatic disease, cancer, nerve damage, autoimmune disease, GvHD, wound healing and tissue regeneration.

According to some embodiments of the invention the mesenchymal stem cells cultured with nicotinamide and/or nicotinamide and FGF4 secrete increased levels of growth factors, and reduced levels of pro-inflammatory factors into the medium.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a bar graph illustrating that basic fibroblast growth factor (bFGF) has a negative effect on the ability of nicotinamide to increase proliferation of mesenchymal stem cells.

Figure 2A:
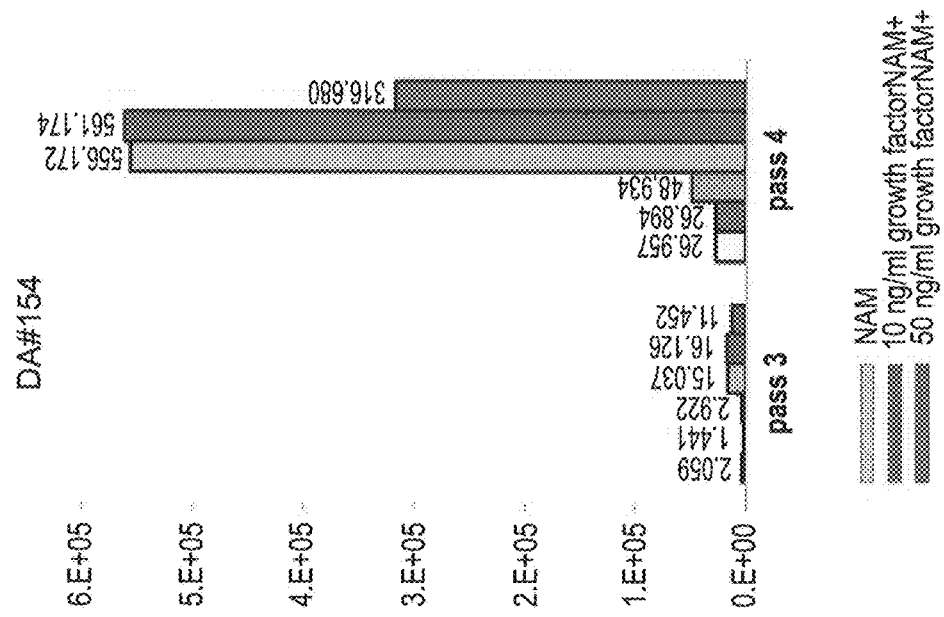
Figure 2B:
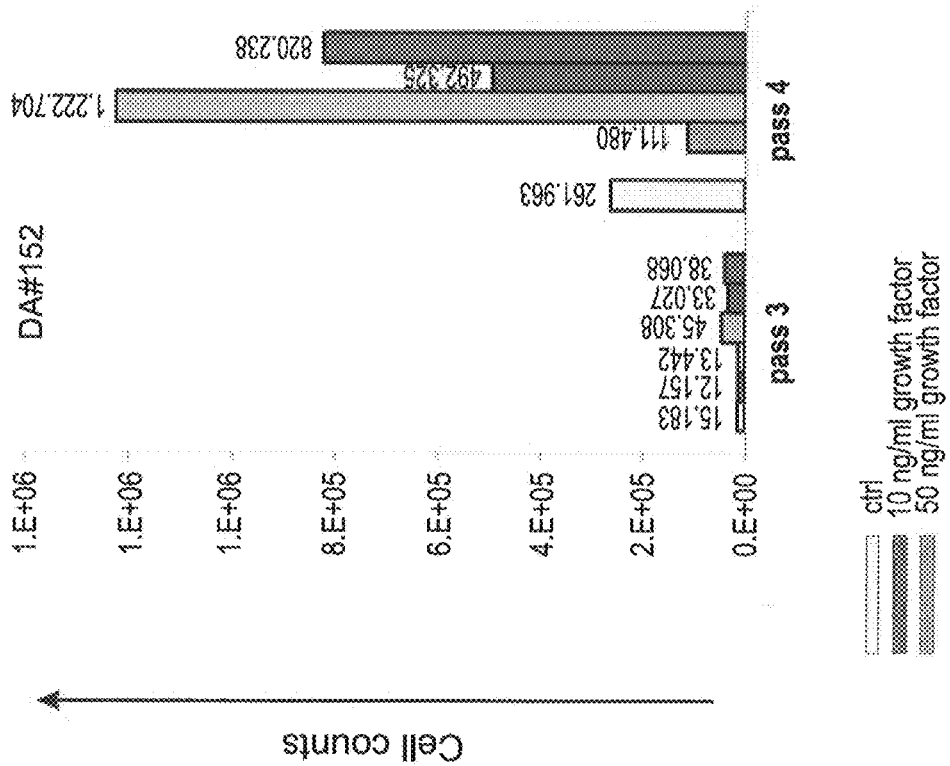
Figure 7A:
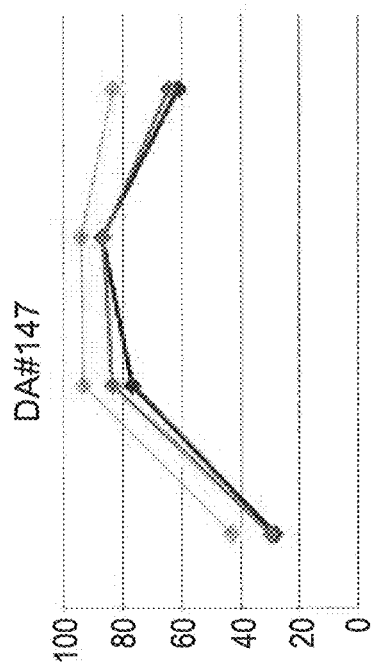
Figure 7B:
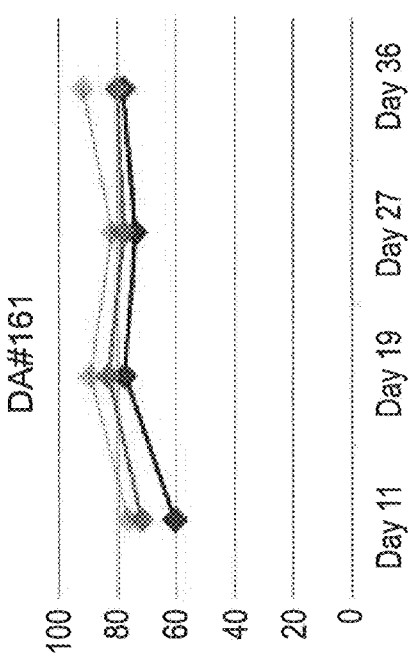
Figure 7C:
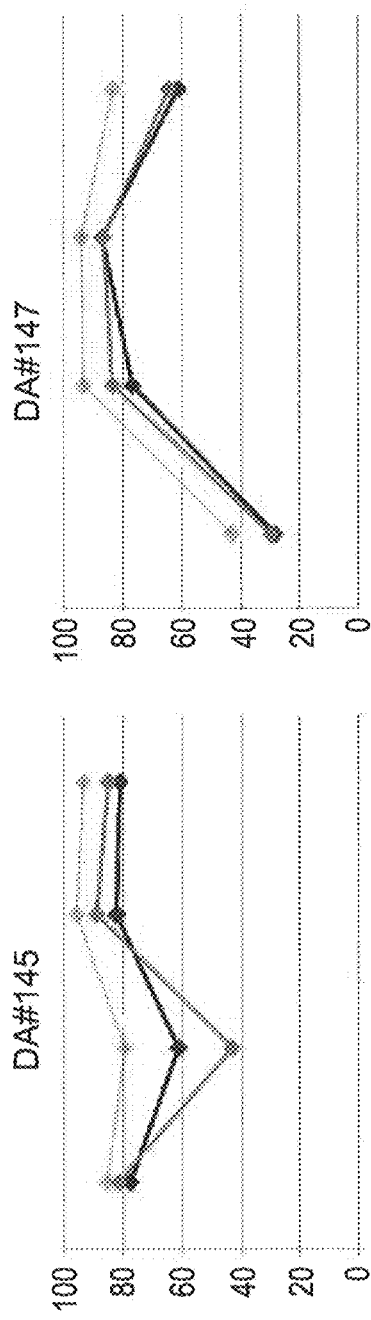
Figure 7D:
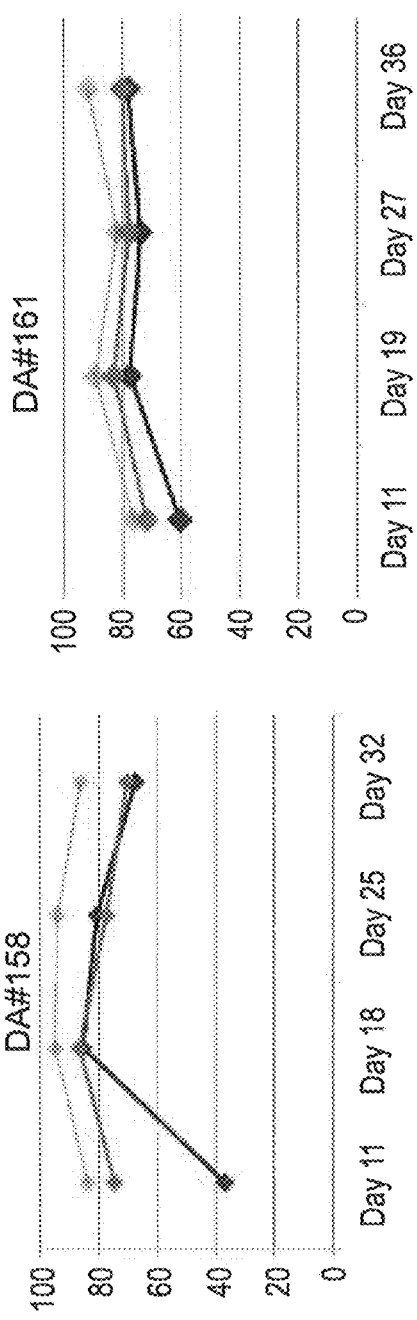

FIGS. 2A-B illustrate that heparin-binding EGF-like growth factor (HB-EGF) has a negative effect on the ability of nicotinamide to increase proliferation of two different batches of mesenchymal stem cells.

FIGS. 3A-D are bar graphs illustrating the synergistic activity of nicotinamide (NAM) and FGF4 on expansion of mesenchymal stem cells. Four different batches of MSC cultures were treated with FGF4 (50 ng/ml), NAM (5 mM) or a combination of FGF4+NAM. Cumulative cell counts at the indicated passages are shown.

FIGS. 4A-B are graphs illustrating that nicotinamide (NAM) preserves the undifferentiated state of MSCs cultured with FGF4. Two different batches of MSC cultures were treated with FGF4 (50 ng/ml), NAM (5 mM) or a combination of FGF4+NAM. Cell size was analyzed by Cedex cell counter.

FIGS. 5A-D are graphs illustrating that cells expanded with a combination of NAM+FGF4 are undifferentiated MSCs (CD105+CD45−). Four different batches of MSC cultures were treated with FGF4 (50 ng/ml), NAM (5 mM) or a combination of FGF4+NAM. Percent of MSC (CD105+CD45−) was analyzed by FACS.

FIGS. 6A-D are bar graphs illustrating inconsistent results obtained following expansion of MSC with NAM+PDGF-BB. Four different batches of MSC cultures were treated with PDGF-BB (50 ng/ml), NAM (5 mM) or a combination of PDGF-BB+NAM. Cumulative cell counts at the indicated passages are shown.

FIGS. 7A-D are graphs illustrating that MSC cultures treated with PDGF-BB or a combination of PDGF-BB+NAM comprise a higher fraction of cells other than MSCs that contaminates the cultures as compared to MSC cultured in the absence of PDGF-BB. Four different batches of MSC cultures were treated with PDGF-BB (50 ng/ml), NAM (5 mM) or a combination of PDGF-BB+NAM. Percent of MSC (CD105+CD45−) was analyzed by FACS.

FIGS. 8A-B are bar graphs illustrating a consistent synergistic effect between NAM and FGF4 in contrast to the absence of a synergistic or additive effect between FGF4 and PDGF-BB. Further, a combination of NAM, FGF4 and PDGF-BB had an adverse effect on MSC expansion. MSC cultures were treated with PDGF-BB (50 ng/ml), FGF4 (50 ng/ml) and NAM (5 mM) or a combination of two or three factors, as indicated. Cumulative cell counts at the indicated passages are shown.

FIGS. 9A-B are graphs illustrating that PDGF-BB supports expansion of cells other than MSCs in MSC cultures. This effect is not alleviated by NAM and/or FGF4. MSC cultures were treated with PDGF-BB (50 ng/ml), FGF4 (50 ng/ml) and NAM (5 mM) or a combination of two or three factors, as indicated. Percent of MSC (CD105+CD45−) was analyzed by FACS.

FIGS. 10A-H are photographs of day 34 MSC cultures illustrating that PDGF-BB supports expansion of cells other than MSC in MSC cultures. This effect is not alleviated by NAM and/or FGF4. MSC cultures were treated with PDGF-BB (50 ng/ml), FGF4 (50 ng/ml) and NAM (5 mM) or a combination of two or three factors, as indicated.

Figure 11:
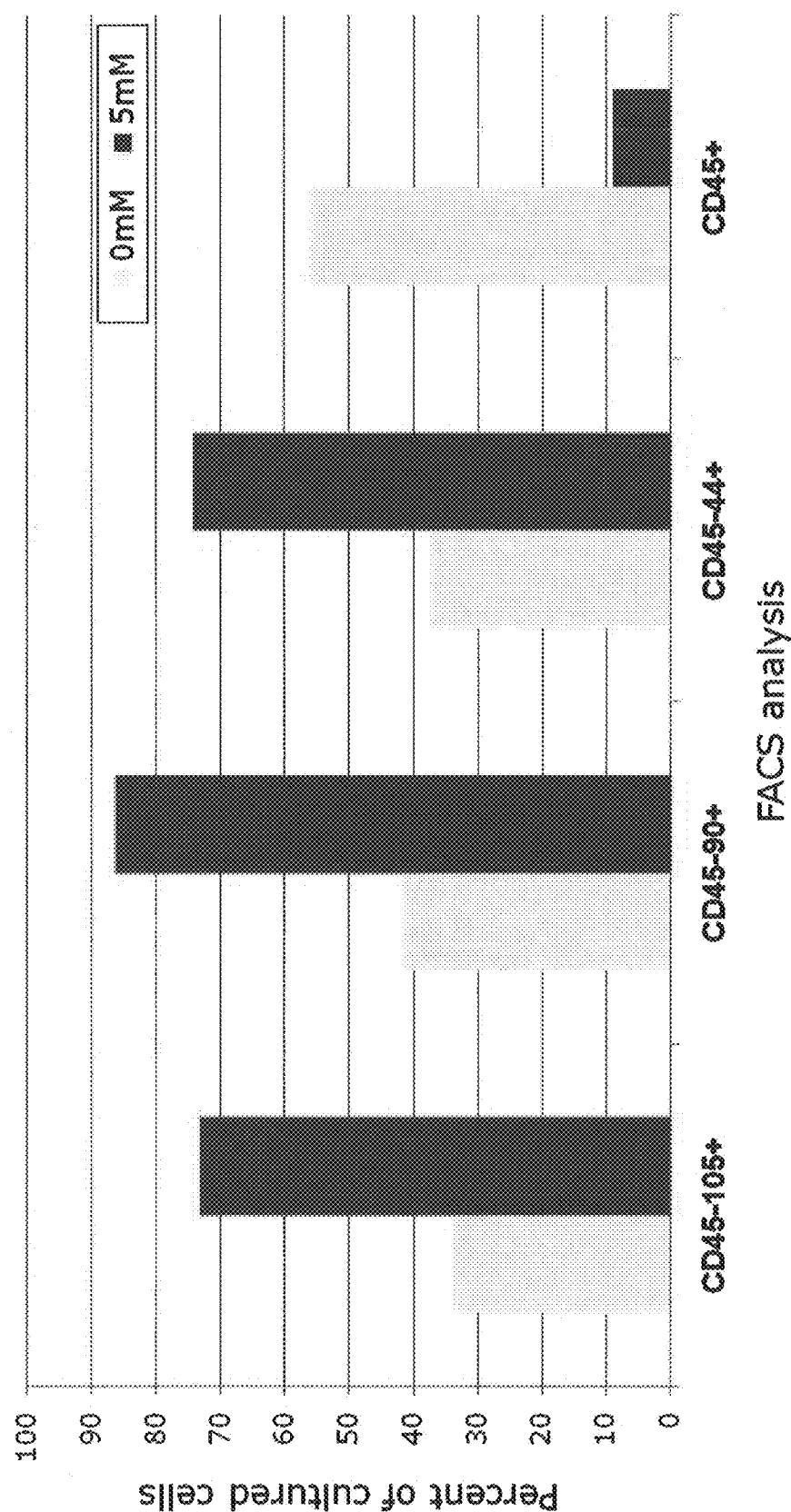

FIG. 11 is a bar graph illustrating % of BM derived adherent cells expressing mesenchymal stem cells markers in culture seeded+/−NAM, prior to the first passage. Mononuclear cells were isolated from bone marrow using Ficoll and the "plastic adherence" method in the presence or absence of Nicotinamide. Non-adherent cells were washed away 3-4 days later and the media was replaced every 3-4 days. FACS analysis was performed in order to obtain expression levels of surface molecules prior to the first passage (8 days post-seeding).

Figure 12A:
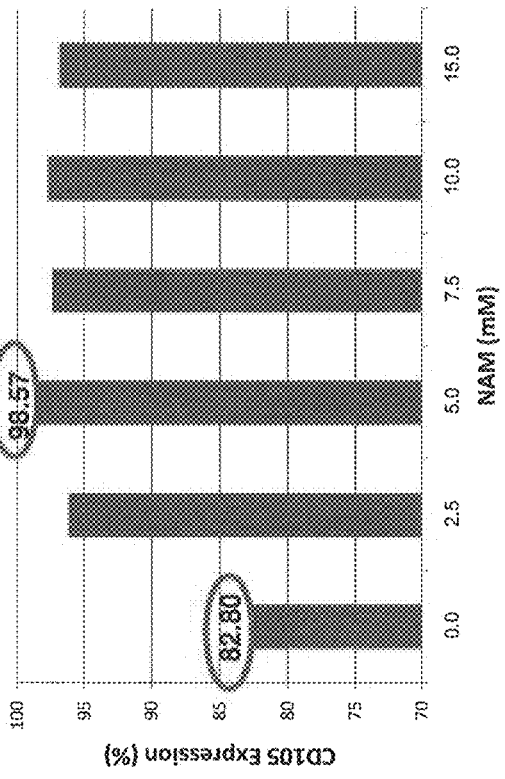
Figure 12C:
Figure 12B:
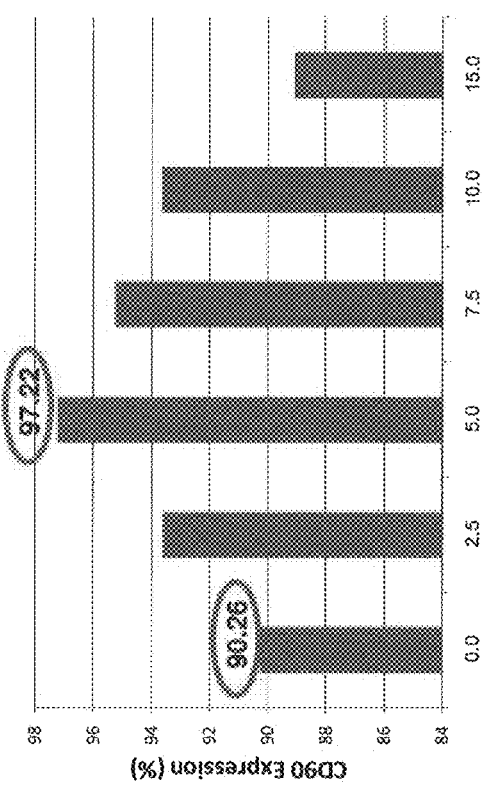

FIGS. 12A-C are graphs illustrating phenotypic characterization of adipose tissue derived mesenchymal stem cells after six passages in different concentrations of nicotinamide.

Figure 13:
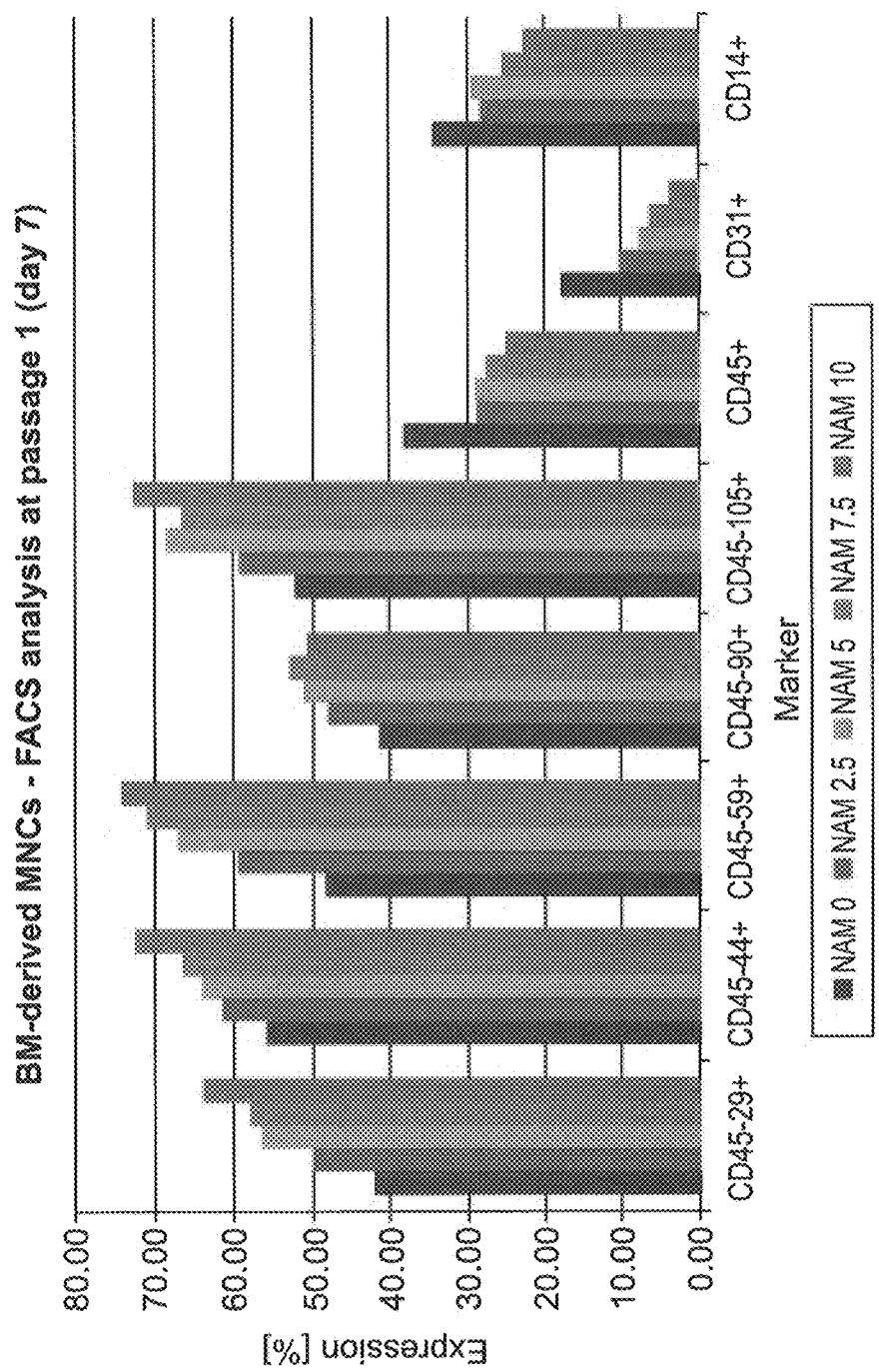

FIG. 13 is a bar graph illustrating phenotypic characterization of bone marrow derived mesenchymal stem cells following the first passage of cultures treated+/−different concentration of nicotinamide. Mononuclear cells were isolated from bone marrow using Ficoll and the "plastic adherence" method. Non-adherent cells were washed away 3-4 days later and the media was replaced every 3-4 days. FACS analysis was performed in order to obtain expression levels of surface molecules following the first passage (8 days post-seeding).

Figure 14:
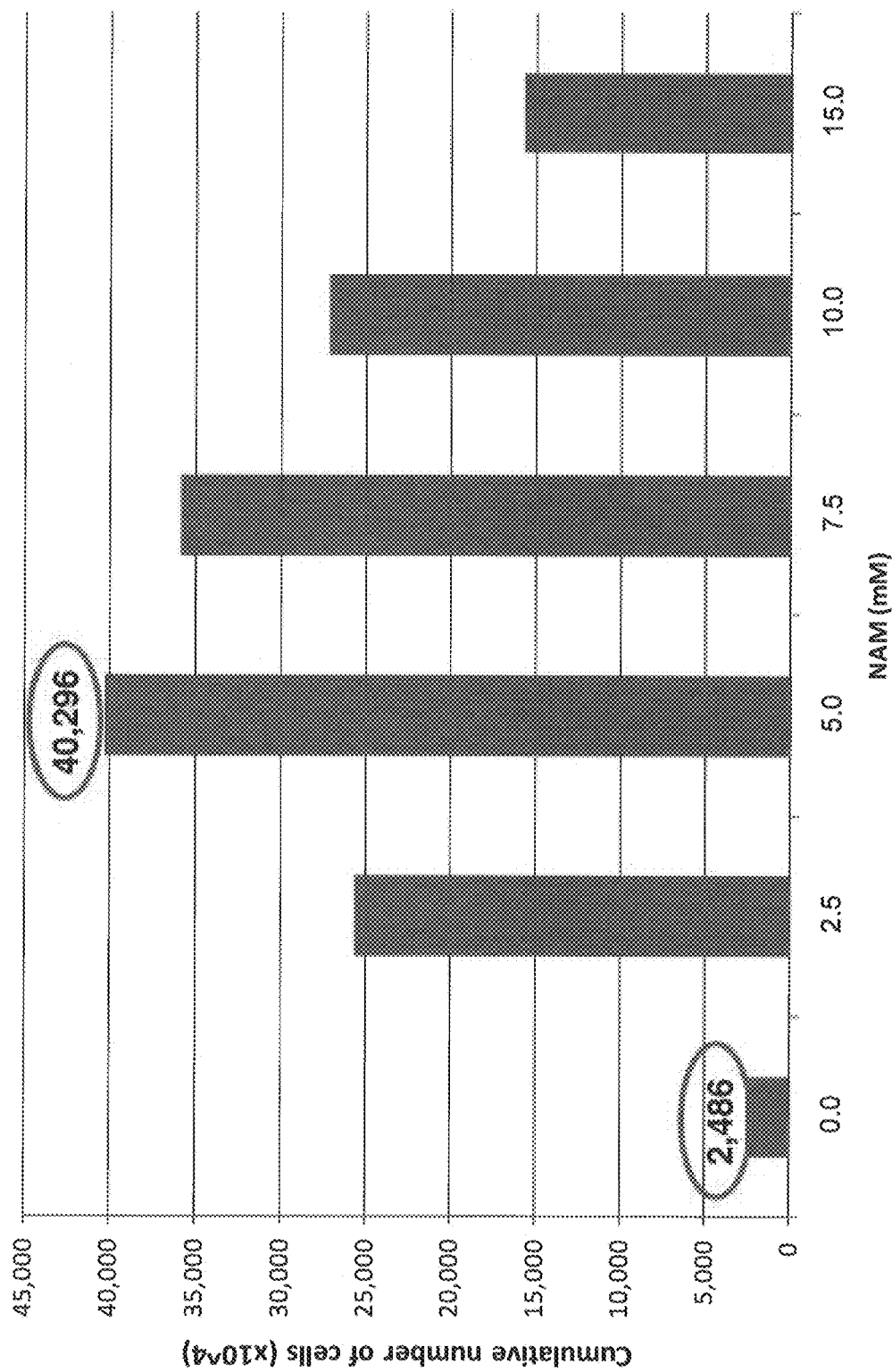

FIG. 14 is a bar graph illustrating the effect of different concentrations of nicotinamide (added at passage 3, and at each subsequent passage) on the number of MSC at passage 6. Nicotinamide substantially improved adipose derived mesenchymal stem cell expansion in culture.

Figure 15:
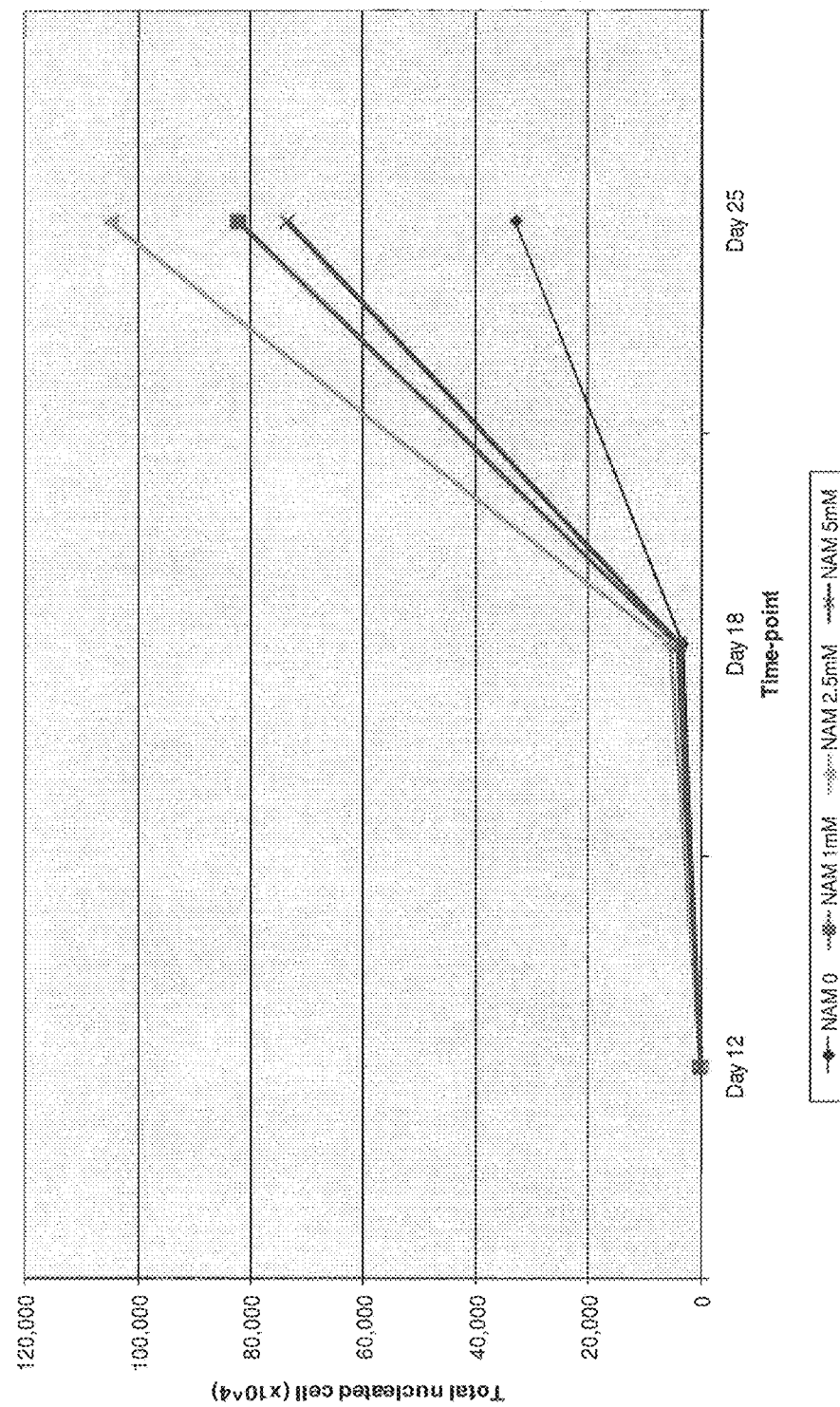

FIG. 15 is a graph illustrating the effect of nicotinamide on bone marrow derived mesenchymal stem cell expansion. Nicotinamide was added from the initiation of the culture and at each subsequent passage.

Figure 16:
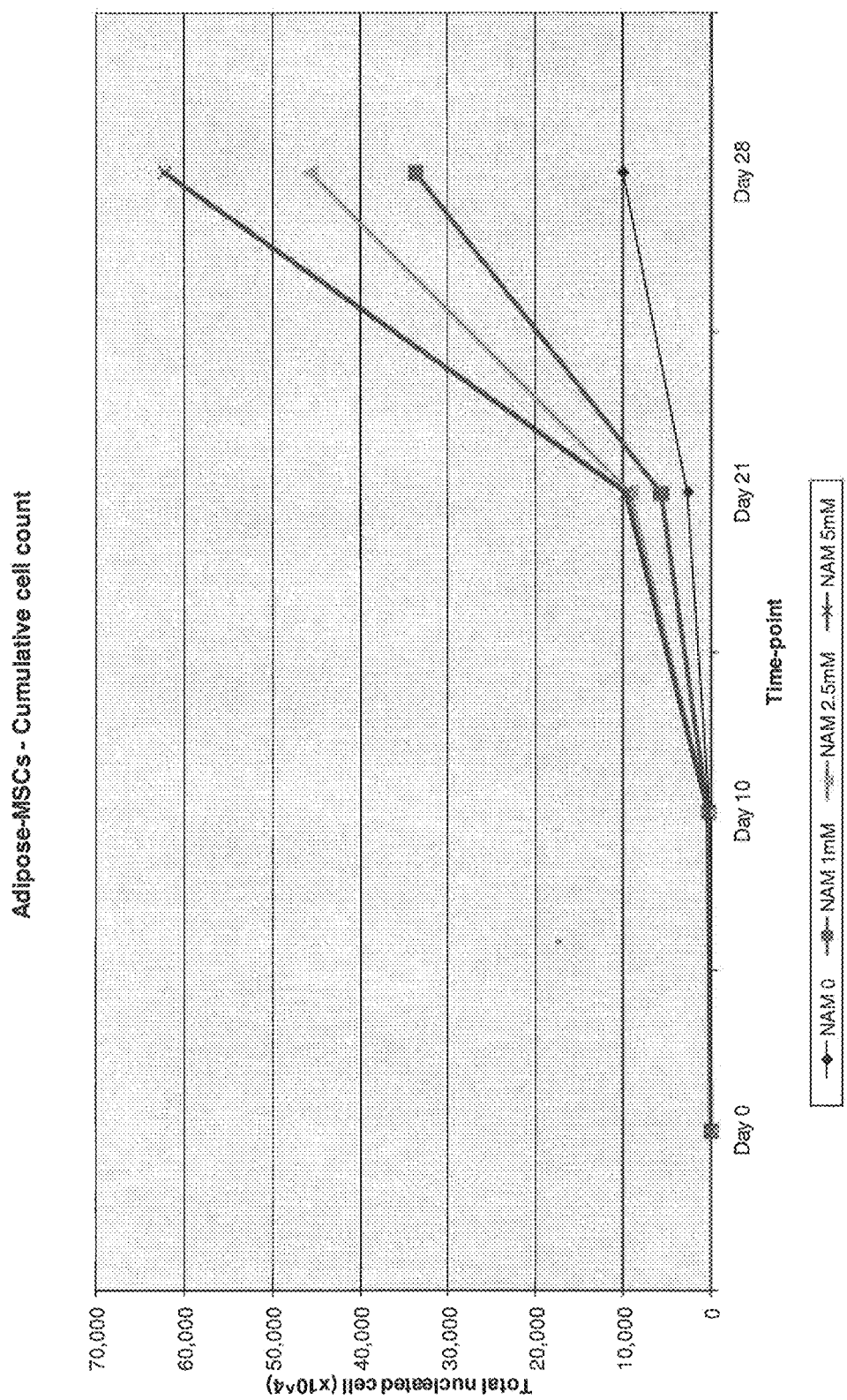

FIG. 16 is a graph illustrating the effect of different concentrations of nicotinamide on adipose derived mesenchymal stem cell expansion. Nicotinamide was added from passage 3 and at each subsequent passage.

Figures 17A, 17B:
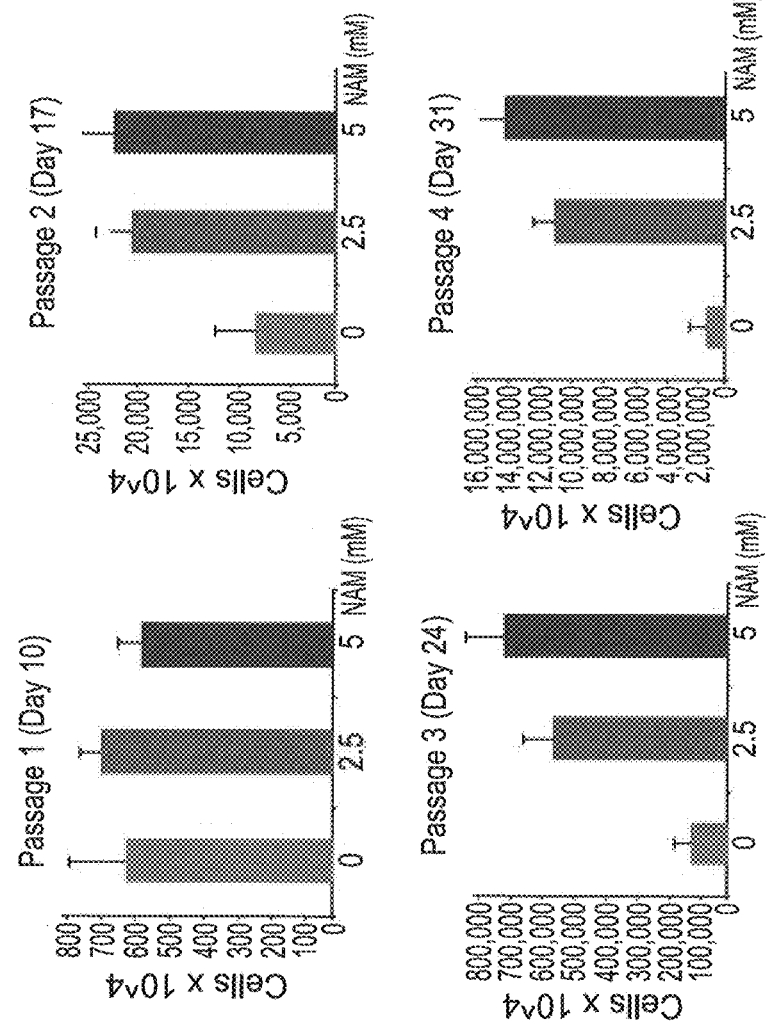

FIGS. 17A-B illustrate that mesenchymal stem cells cultured in nicotinamide, expand more rapidly than mesenchymal stem cells cultured under identical conditions, but in the absence of nicotinamide.

FIG. 18 is a graph illustrating the effect of nicotinamide on the cumulative cell count of mesenchymal stem cells cultured in a large batch.

Figure 19:
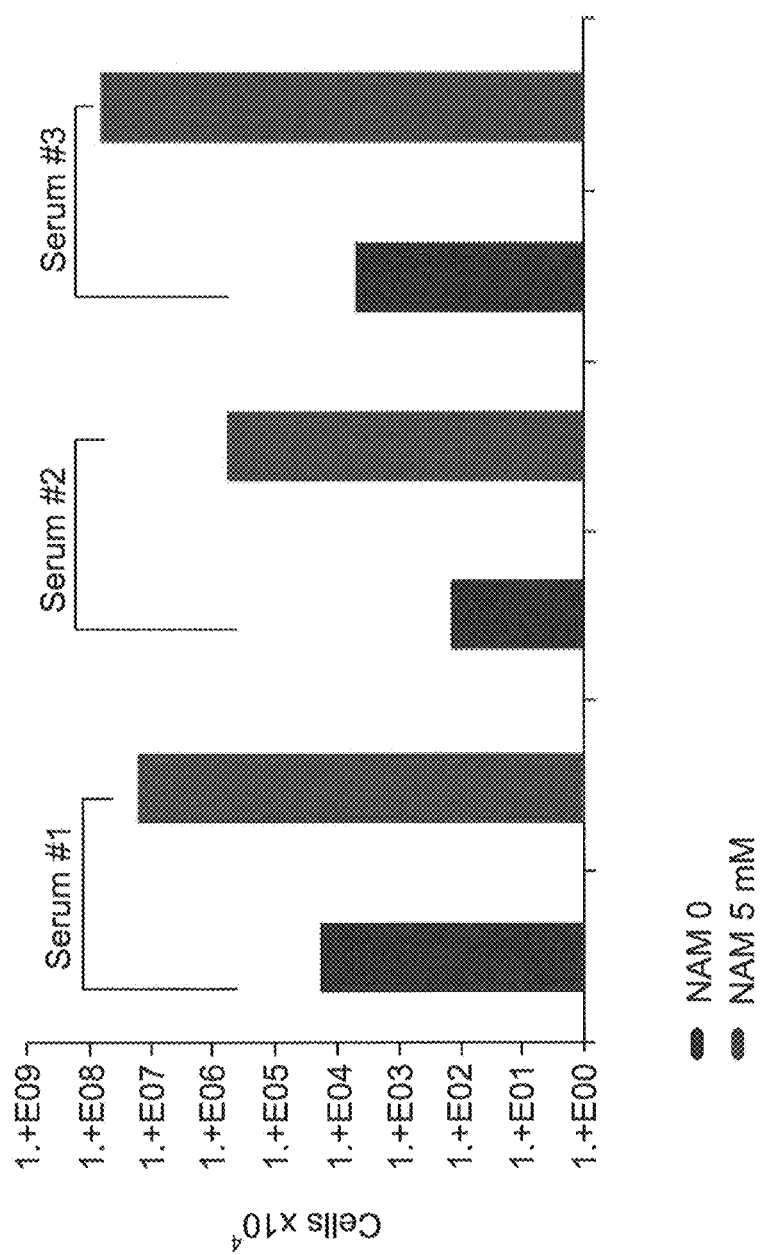

FIG. 19 is a bar graph illustrating the results of one of two experiments performed illustrating that the effect of nicotinamide on mesenchymal stem cell proliferation is not dependent on the particular batch of serum used.

Figures 20A, 20B, 20C:
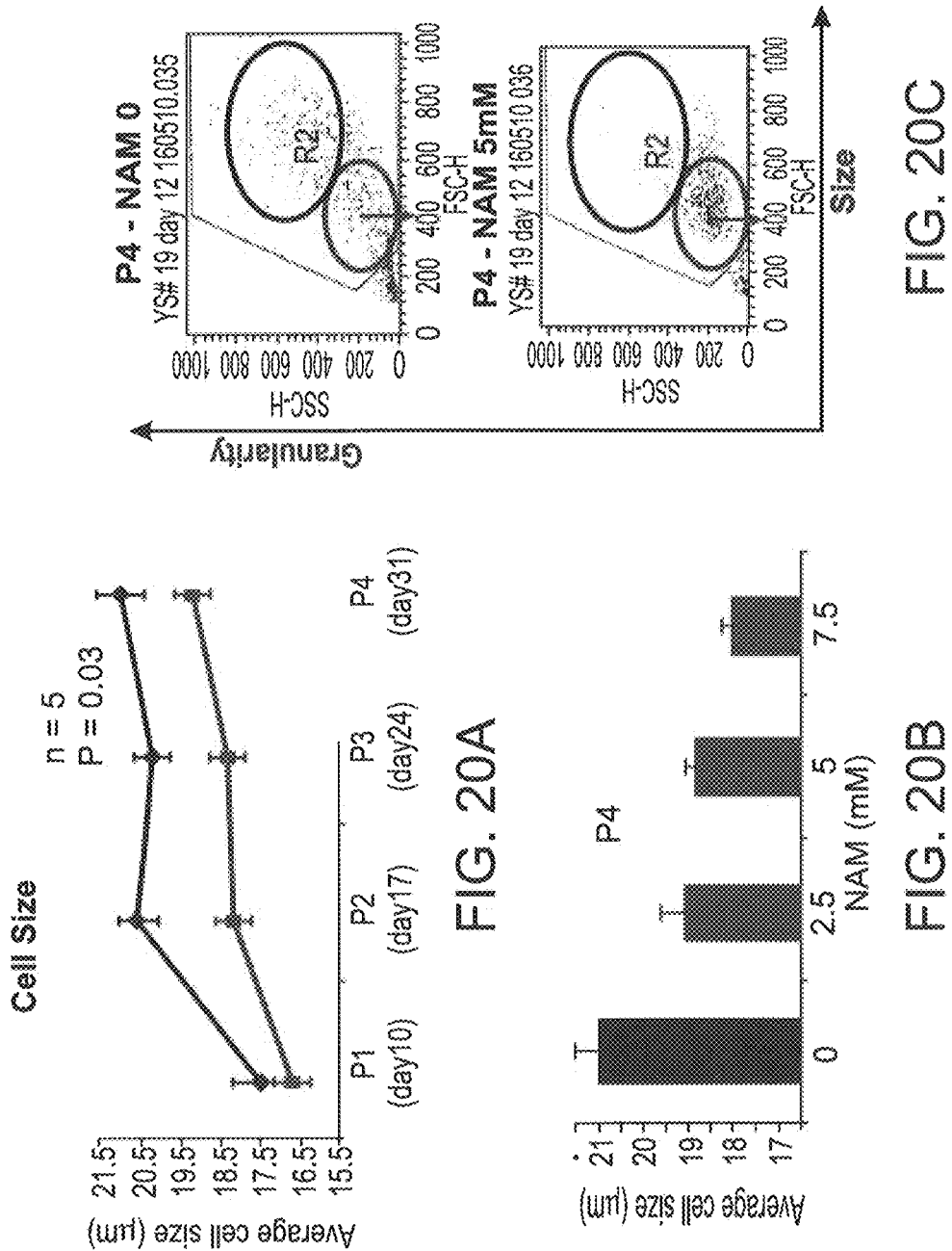

FIGS. 20A-C are graphs and plots illustrating the beneficial effect of culturing in the presence of nicotinamide on cell size and granularity. FIG. 20C shows that cells grown in the presence of nicotinamide are smaller and less granular (most of the cells are in the red circle), as oppose to cells grown without nicotinamide which are larger and more granular (black circle). For FIG. 20A, the concentration of nicotinamide used was 5 mM.

Figure 21B:
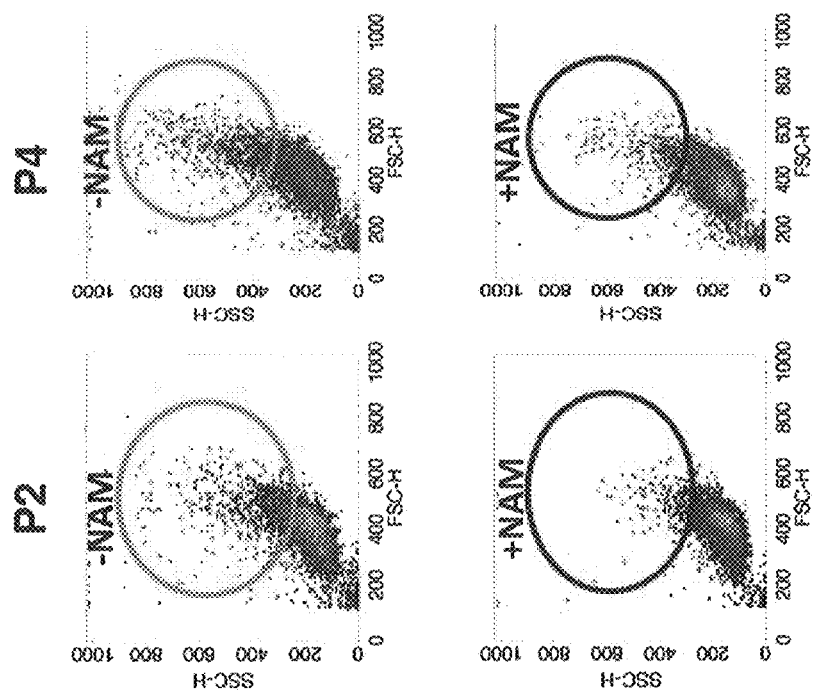
Figure 21A:
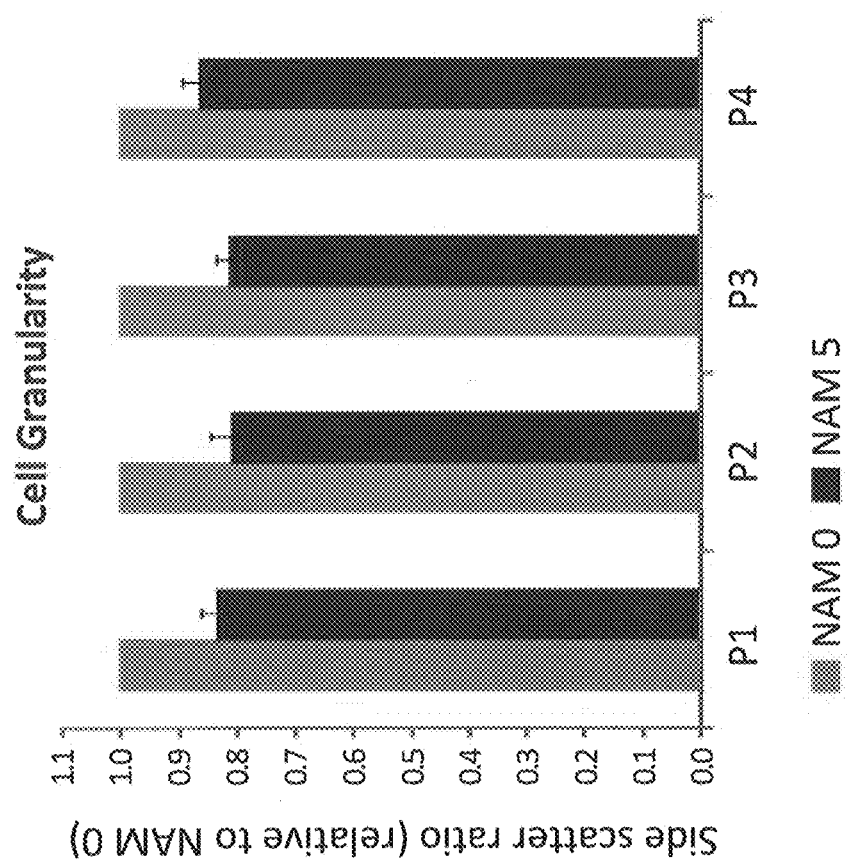

FIGS. 21A-B are graphs and plots illustrating that mesenchymal stem cells grown in the presence of nicotinamide are less granular than mesenchymal stem cells grown in the absence of nicotinamide under identical conditions.

Figure 22:
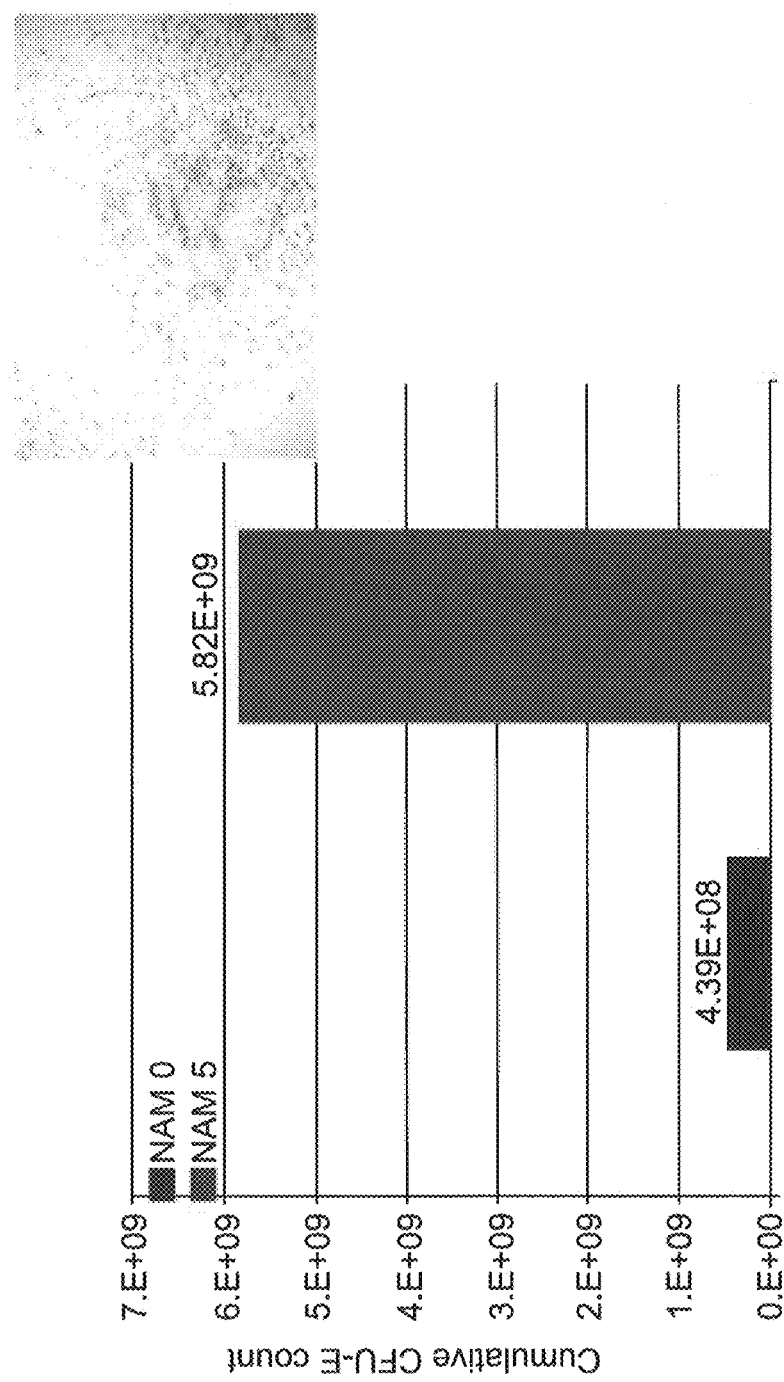

FIG. 22 is a graph illustrating that culturing MSCs in the presence of nicotinamide (5 mM) increases the cumulative CFU-F count.

FIGS. 23A-D are photographs illustrating that nicotinamide reduces the amount of senescence of mesenchymal stem cells. Bone marrow-derived mesenchymal stem cells were cultured for 5 passages+/−5 mM NAM. The cells were fixated and X-Gal staining was performed to detect senescent cells (blue stain).

Figure 24A:
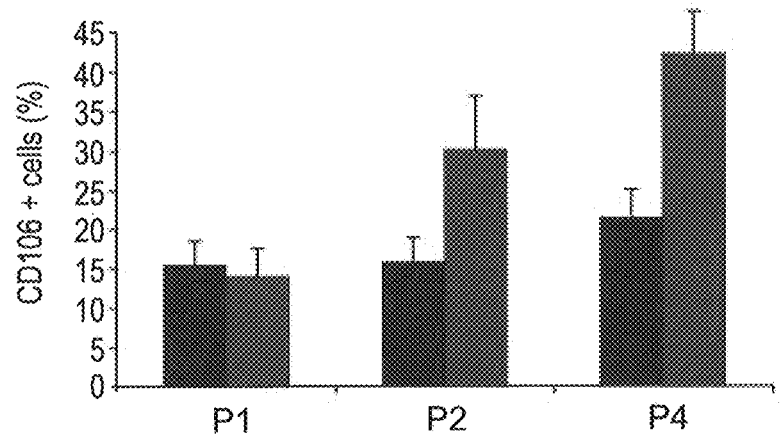
Figure 24B:
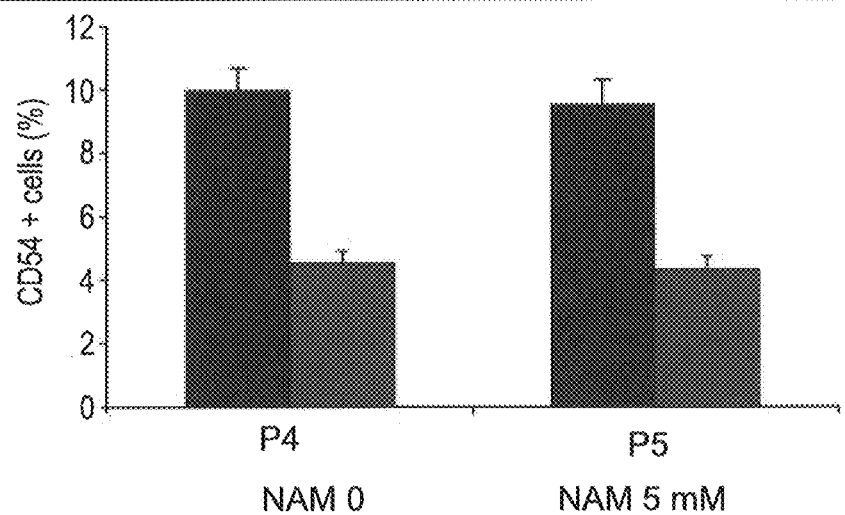
Figure 25A:
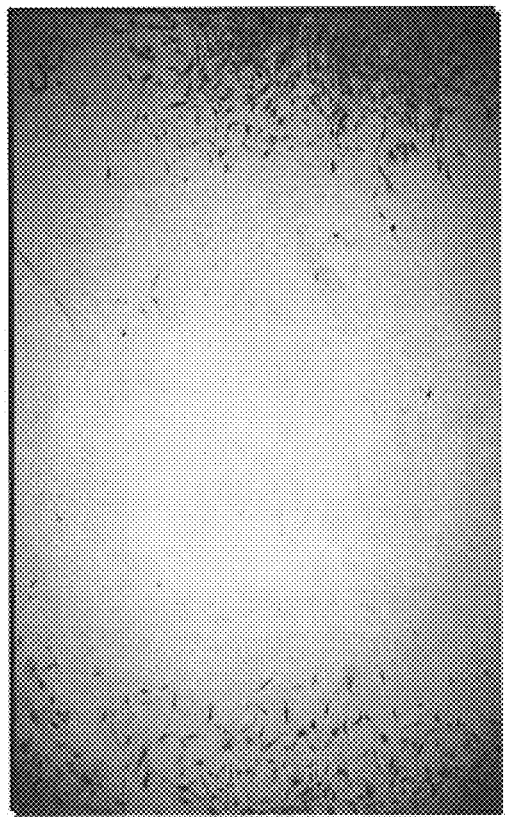
Figure 25B:
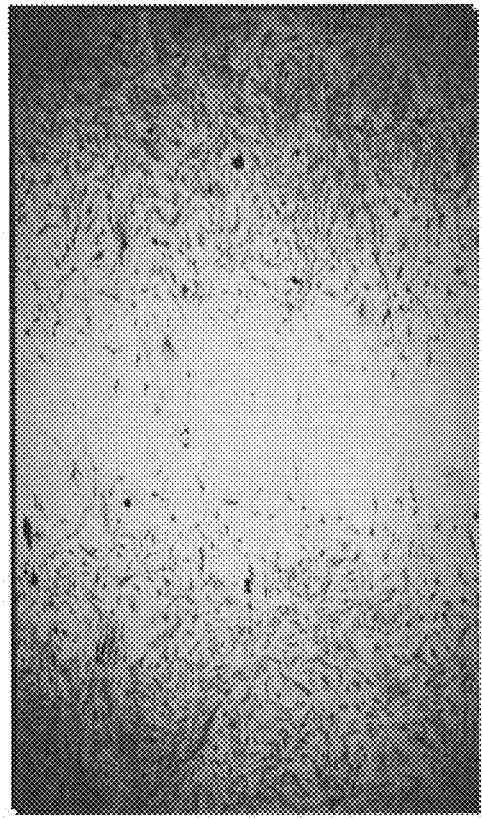

FIGS. 24A-B are bar graphs illustrating that nicotinamide modulates expression of surface markers on mesenchymal stem cells—VCAM1/CD106 (FIG. 24A) and CD54 (FIG. 24B). Note the enhanced expression of VCAM1/CD106 and reduced expression of CD54 in cells grown in the presence of nicotinamide;

FIGS. 25A-B are photographs illustrating results of an in vitro wound healing assay which was performed on MSCs cultured with (FIG. 25B) or without (FIG. 25A) nicotinamide at passage 3. Wound healing was observed 4 days post wound formation.

Figure 26:
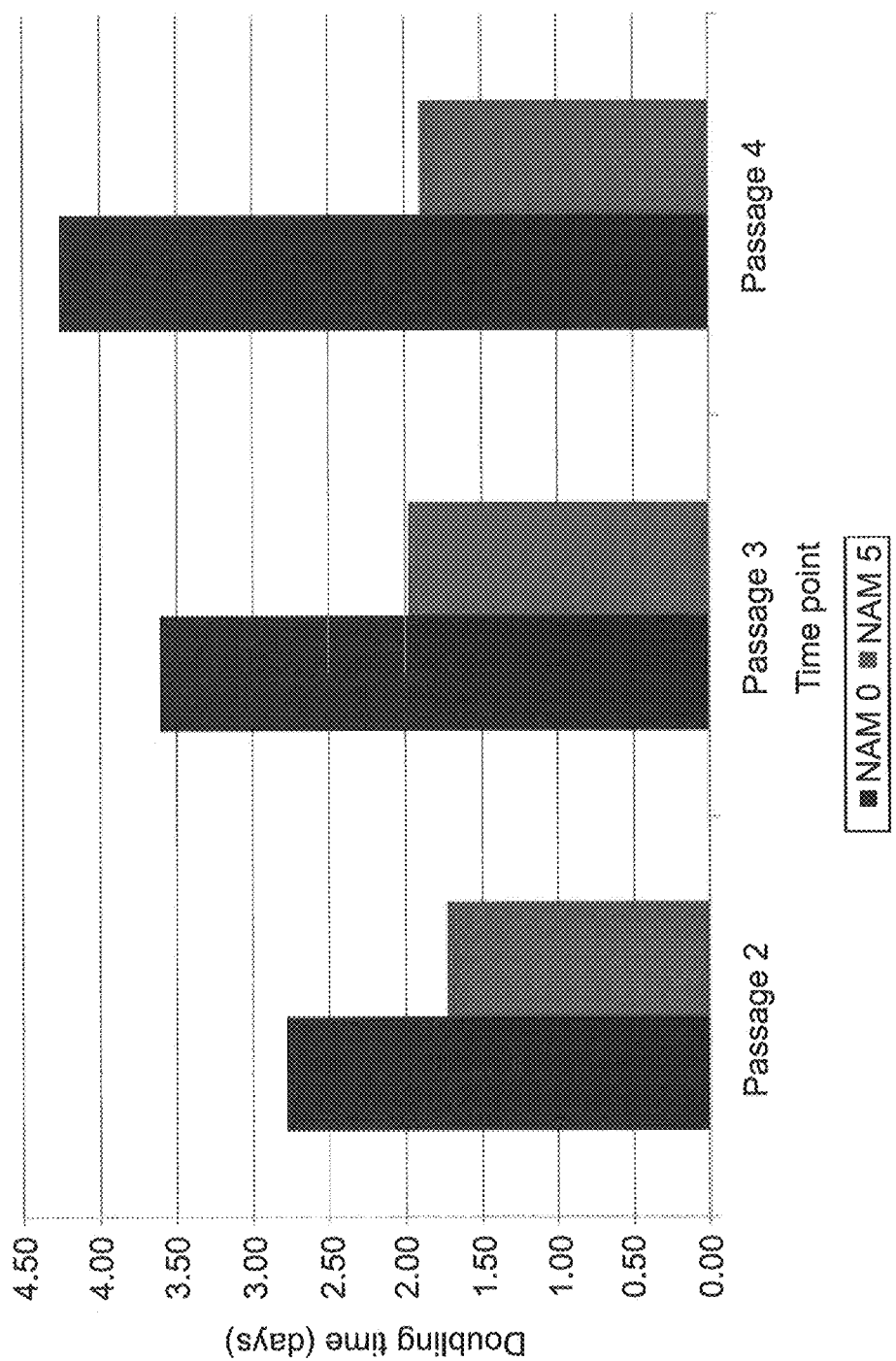

FIG. 26 is a graph illustrating the effect of nicotinamide on bone marrow derived mesenchymal stem cell Doubling Time. Nicotinamide was added from the initiation of the culture and at each subsequent passage.

Figure 27:
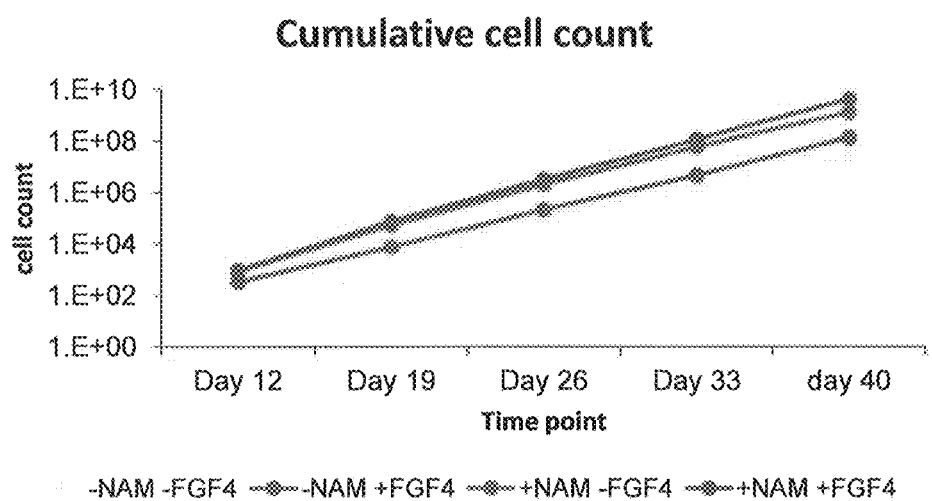
Figure 28:
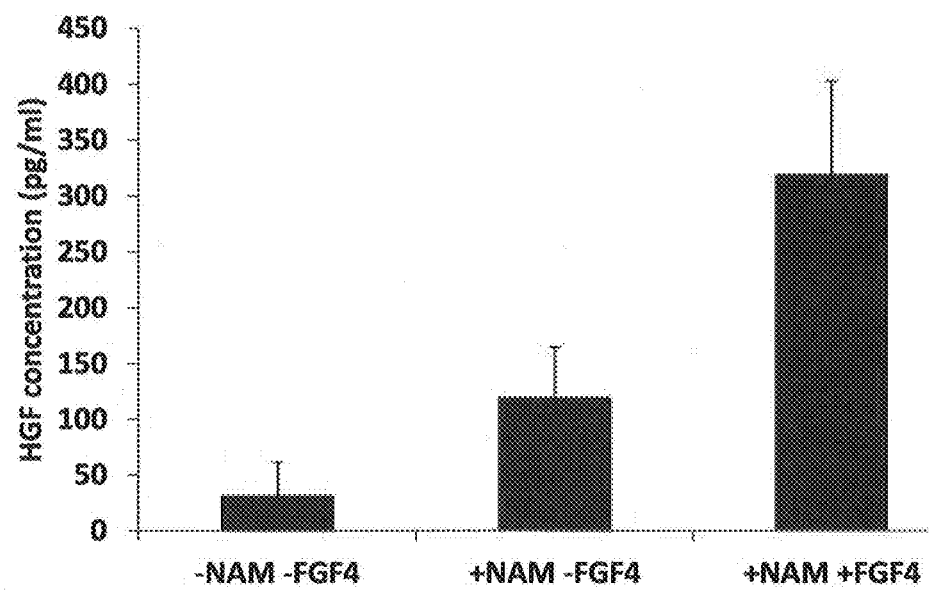
Figure 29:
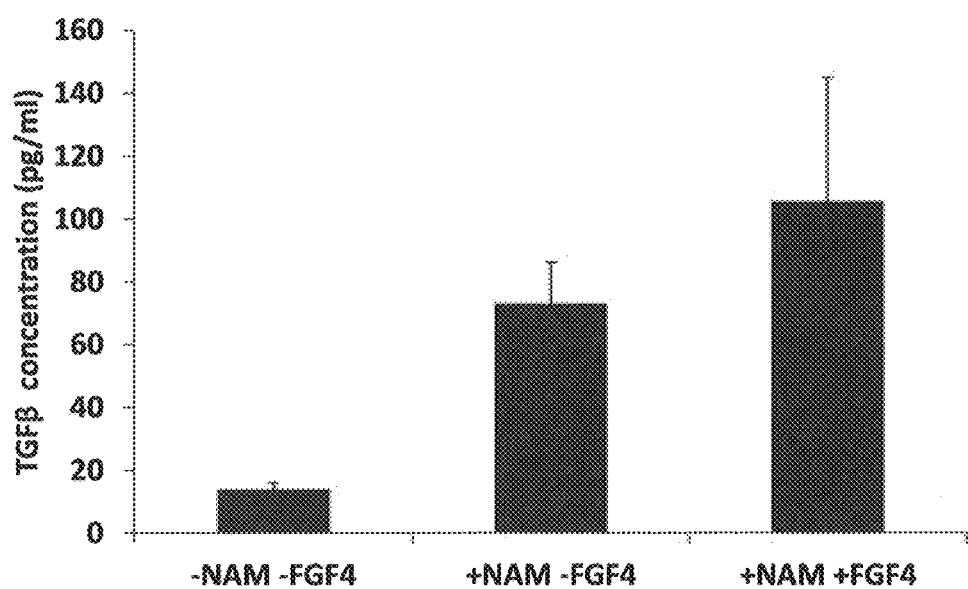
Figure 30:
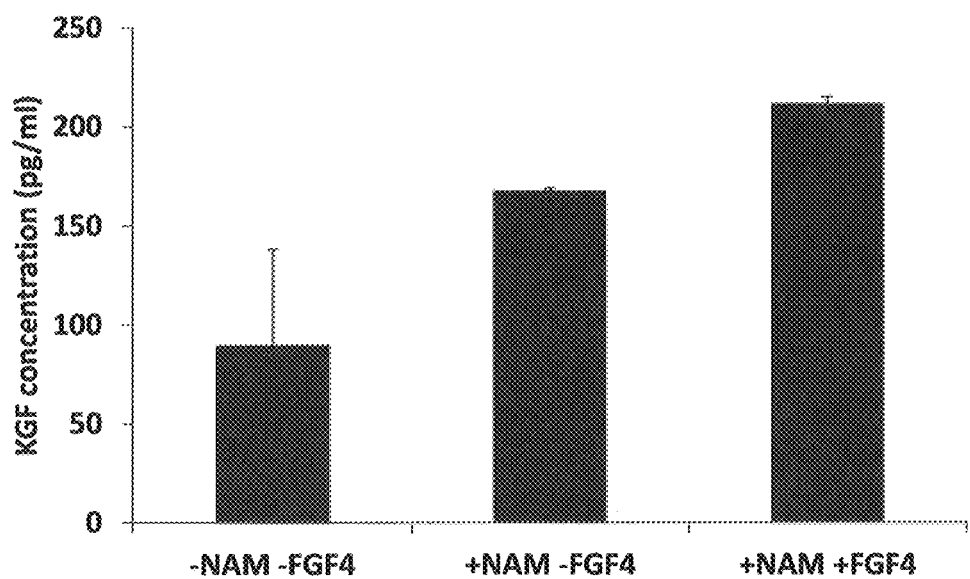
Figure 31:
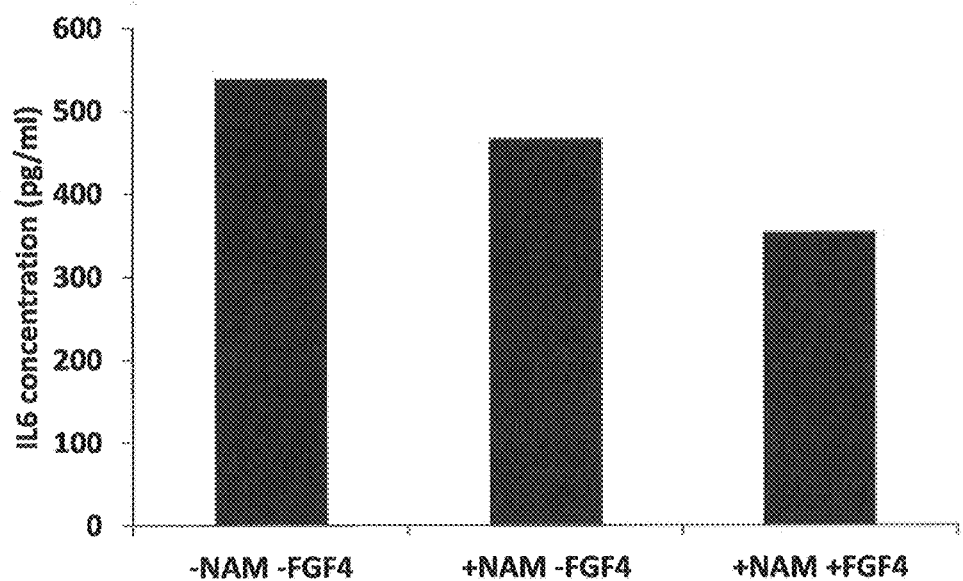
Figure 32:
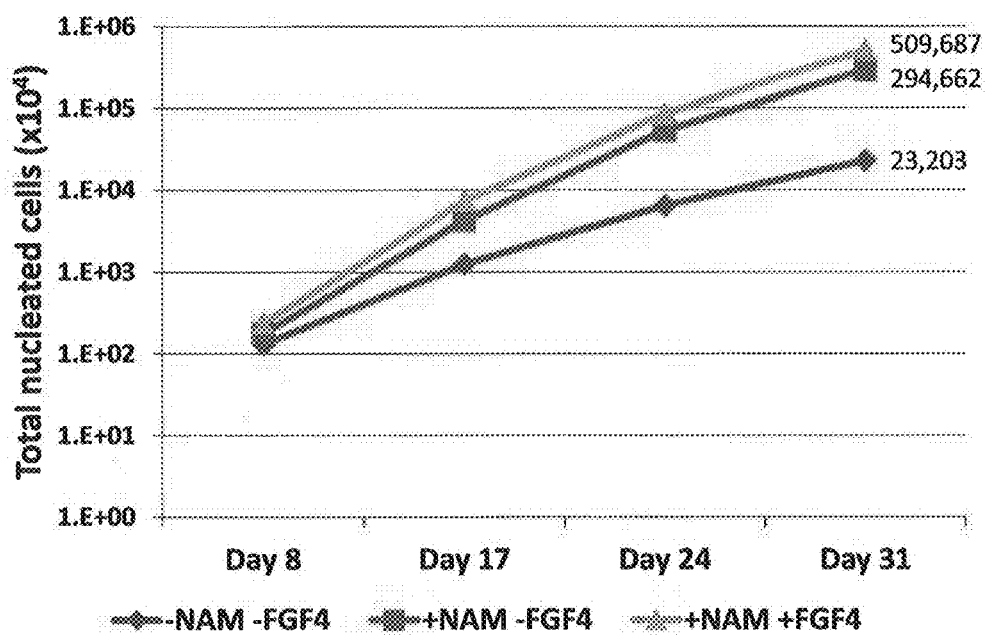
Figure 33:
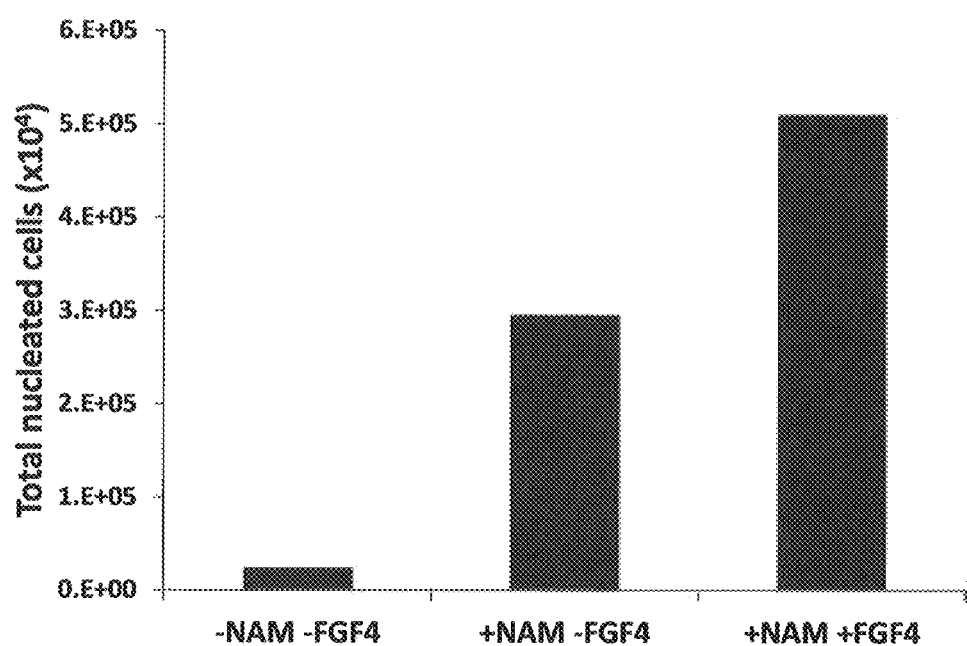
Figure 34:
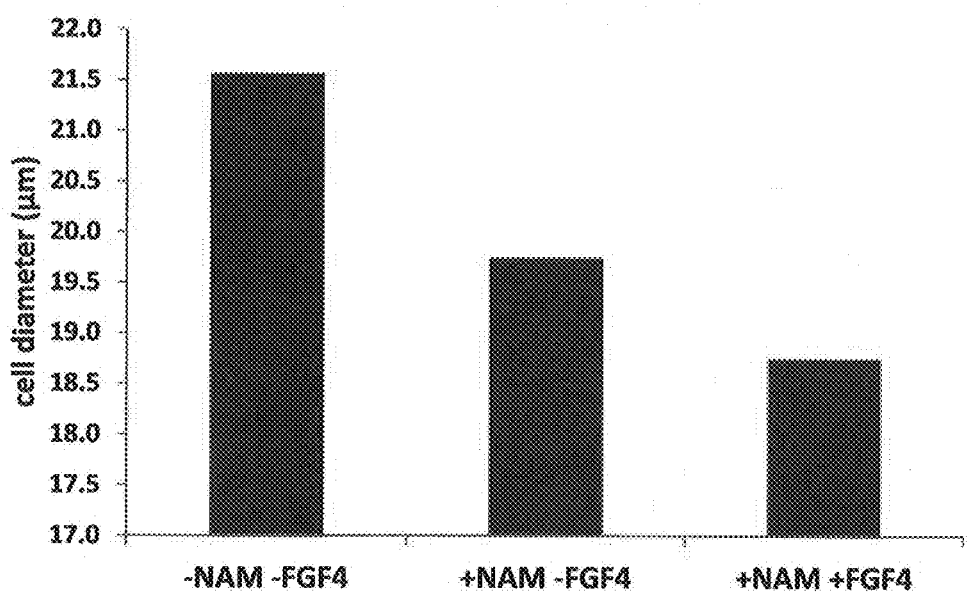
Figure 35:
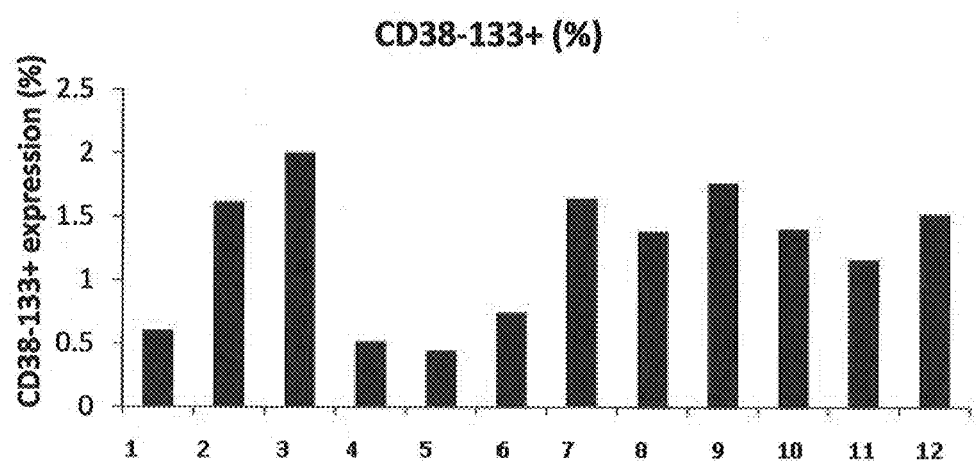

FIG. 27 is a graph illustrating the effect of nicotinamide, with and without FGF4 on bone marrow-derived MSC proliferation, through 5 passages of culture. Bone-marrow derived mesenchymal stem cells were isolated using Ficoll and plastic adherence method, and cultured for several passages with fetal bovine serum. −NAM−FGF4=controls (light blue circles), −NAM+FGF4=culture with 50 ng/ml FGF4 (dark blue circles), +NAM−FGF4=culture with 5 mM NAM (pink circles), +NAM+FGF4=culture with 50 ng/ml FGF4 and 5 mM NAM (red circles). Note the synergic effect of Nicotinamide and FGF4 added together throughout all passages of MSC proliferation;

FIG. 28 is a bar graph illustrating enhancement of Hepatocyte Growth Factor (HGF) content of conditioned medium from nicotinamide and FGF4-treated MSC cultures. Bone marrow mesenchymal stem cells were isolated using Ficoll and plastic adherence method, and cultured for several passages with fetal bovine serum, with added nicotinamide and FGF4 (+NAM+FGF4), with added nicotinamide (+NAM−FGF4) and without added nicotinamide or FGF (−NAM−FGF4). Twenty four hours before passage 4, the media was changed and fresh media without fetal bovine serum or FGF4 was added. The cultured media from passage 4 cultures was collected and assayed for HGF content by ELISA. −NAM, −FGF4=control; +NAM−FGF4=5 mM NAM, +NAM+FGF4=5 mM NAM+50 ng/ml FGF4. Note the significant effect of combined FGF4 and nicotinamide on HGF secretion;

FIG. 29 is a bar graph illustrating enhancement of Transforming Growth Factor-β (TGFβ) content of conditioned medium from nicotinamide and FGF4-treated MSC cultures. Bone marrow mesenchymal stem cells were isolated and cultured as in FIG. 28 above. Cultured media was changed to medium without fetal bovine serum or FGF4 24 hours prior to passage 4, collected from the passage 4 cultures and assayed for TGFβ content by ELISA. −NAM, −FGF4=control; +NAM−FGF4=5 mM NAM, +NAM+FGF4=5 mM NAM+50 ng/ml FGF4. Note the significant effect of combined FGF4 and nicotinamide on TGFβ secretion;

FIG. 30 is a bar graph illustrating enhancement of Keratinocyte Growth Factor (KGF) content of conditioned medium from nicotinamide and FGF4-treated MSC cultures. Bone marrow mesenchymal stem cells were isolated and cultured as in FIG. 28 above. Cultured media was changed to medium without fetal bovine serum or FGF4 24 hours prior to passage 4, collected from the passage 4 cultures and assayed for KGF content by ELISA. −NAM, −FGF4=control; +NAM−FGF4=5 mM NAM, +NAM+FGF4=5 mM NAM+50 ng/ml FGF4. Note the significant effect of combined FGF4 and nicotinamide on KGF secretion;

FIG. 31 is a bar graph illustrating reduction of cytokine IL-6 (IL-6) content of conditioned medium from nicotinamide and FGF4-treated MSC cultures. Bone marrow mesenchymal stem cells were isolated and cultured as in FIG. 28 above. Cultured media was changed to medium without fetal bovine serum or FGF4 24 hours prior to passage 4, collected from the passage 4 cultures and assayed for IL-6 content by ELISA. −NAM, −FGF4=control; +NAM−FGF4=5 mM NAM, +NAM+FGF4=5 mM NAM+50 ng/ml FGF4. Note the significant reduction by combined FGF4 and nicotinamide on IL-6 secretion;

FIG. 32 is a graph illustrating the effect of nicotinamide, with and without FGF4 on adipose-derived MSC proliferation, through 4 passages of culture. Adipose derived mesenchymal stem cells were isolated using collagenase digestion and plastic adherence method, and cultured for several passages with fetal bovine serum. −NAM−FGF4=controls (blue diamonds), +NAM−FGF4=culture with 5 mM NAM (red squares), +NAM+FGF4=culture with 50 ng/ml FGF4 and 5 mM NAM (green triangles). Note the synergic effect of Nicotinamide and FGF4 added together on adipose-derived MSC proliferation;

FIG. 33 is a graph detailing the effect of nicotinamide, with and without FGF4 on nucleated cell proliferation in adipose-derived MSC proliferation at passage 4. Adipose-derived mesenchymal stem cells were isolated and cultured as described in FIG. 32. −NAM−FGF4=controls, +NAM−FGF4=culture with 5 mM/ml NAM, +NAM+FGF4=culture with 50 ng/ml FGF4 and 5 mM/ml NAM. Note the synergic effect of nicotinamide and FGF4 together on proliferation of total nucleated cells in the culture;

FIG. 34 is a bar graph illustrating the beneficial effect of culturing adipose derived MSCs in the presence of nicotinamide and FGF4 on the size of the cultured mesenchymal stem cells. Adipose-derived mesenchymal stem cells were isolated and cultured as described in FIG. 32. Cell size was analyzed by Cedex cell counter. −NAM−FGF4=controls, +NAM−FGF4=culture with 5 mM/ml NAM, +NAM+FGF4=culture with 50 ng/ml FGF4 and 5 mM/ml NAM. Note that smaller size of MSC cells grown in the presence of nicotinamide, and even smaller MSCs grown with nicotinamide and FGF4;

FIG. 35 is a bar graph showing the effect of nicotinamide with and without FGF4 on differentiation of ex-vivo expanded hematopoietic cells. Umbilical cord-derived early progenitor (CD 133+) hematopoietic cells were isolated using CD133 microbeads and CliniMACS (Milentyi, Inc), and cultured for 3 weeks in MEMα supplemented with 50 ng/ml early acting cytokines and fetal bovine serum, ±2.5 or 5 mM nicotinamide (NAM), ±10, 50 or 200 ng/ml FGF4. After three weeks culture CD38-CD133+ cells were stained and counted by FACS. Column 1=Control: −NAM, −FGF4, Column 2=+2.5 mM NAM, Column 3=+5 mM NAM, Column 4=+10 ng/ml FGF4, Column 5=+50 ng/ml FGF4, Column 6=+200 ng/ml FGF4, Column 7=+2.5 mM NAM, +10 ng/ml FGF4, Column 8=+2.5 mM NAM, +50 ng/ml FGF4, Column 9=+2.5 mM NAM, +200 ng/ml FGF4, Column 10=+5 mM NAM, +10 ng/ml FGF4, Column 11=+5 mM NAM, +50 ng/ml FGF4, Column 12=+5 mM NAM, +200 ng/ml FGF4.

Figure 36:
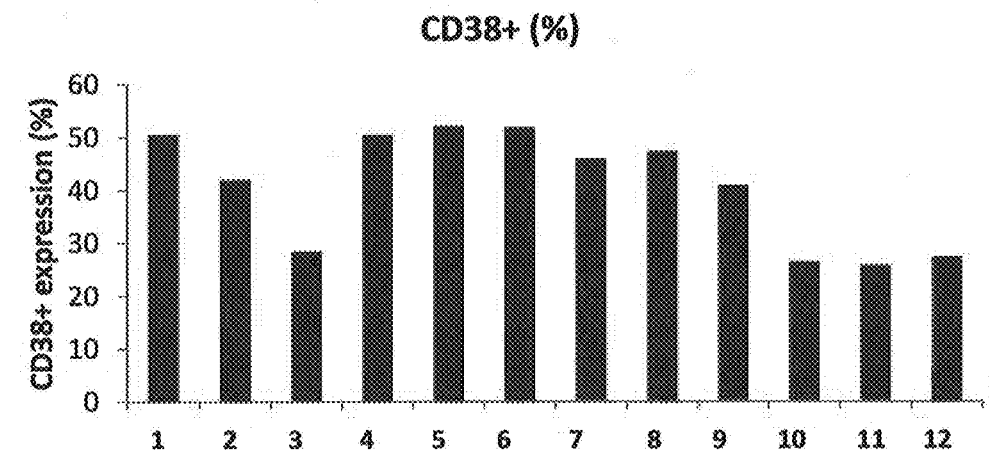
Figure 37:
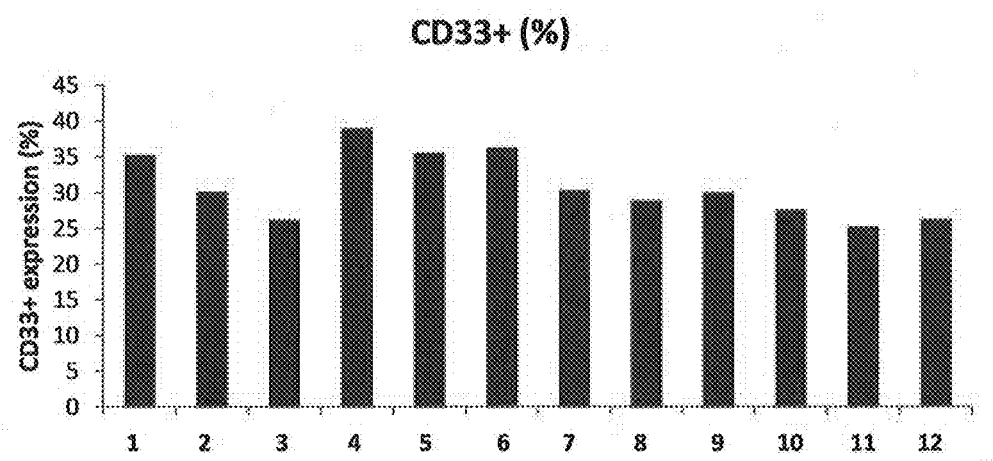
Figure 38:
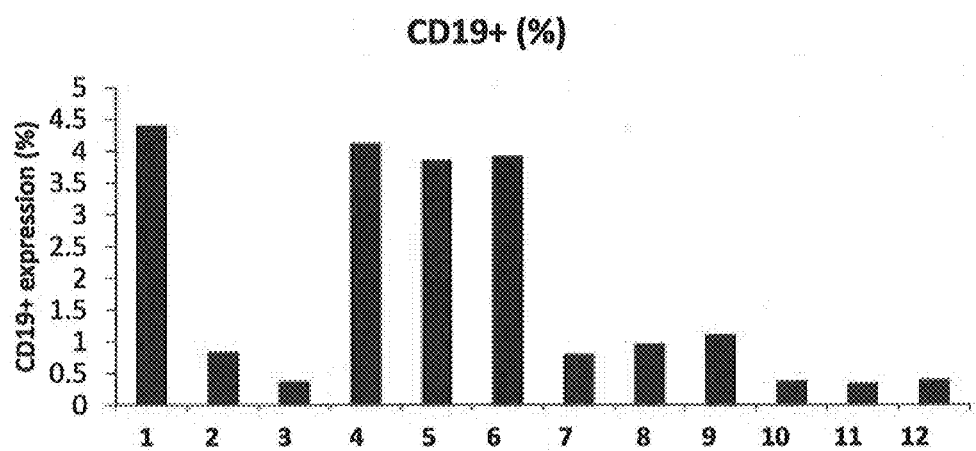

Note the significantly greater fraction of undifferentiated early progenitors (CD38− CD133+) in the nicotinamide-treated cultures (columns 2 and 3), absence of any significant effect of FGF4 alone (columns 4-6) and absence of any significant effect of FGF4 on the nicotinamide-mediated inhibition of hematopoietic progenitor cell differentiation (columns 7-12);

FIG. 36 is a bar graph showing the effect of nicotinamide with and without FGF4 on differentiation of ex-vivo expanded hematopoietic cells. Umbilical cord-derived progenitor (CD 133+) hematopoietic cells were isolated and cultured, with and without nicotinamide and FGF4, as in FIG. 35. After three weeks culture CD38+ cells were stained and counted by FACS. Columns 1-12 as in FIG. 35. Note the significant inhibition of differentiation (CD38+ cells) in the nicotinamide-treated cultures (columns 2 and 3), absence of any significant effect of FGF4 alone on differentiation (columns 4-6) and absence of any significant effect of FGF4 on the nicotinamide-mediated inhibition of hematopoietic progenitor cell differentiation (columns 7-12);

FIG. 37 is a bar graph showing the effect of nicotinamide with and without FGF4 on myeloid lineage differentiation of ex-vivo expanded hematopoietic cells. Umbilical cord-derived progenitor (CD 133+) hematopoietic cells were isolated and cultured, with and without nicotinamide and FGF4, as in FIG. 35. After three weeks culture myeloid lineage differentiated (CD33+) cells were stained and counted by FACS. Columns 1-12 as in FIG. 35. Note the significant inhibition of myeloid lineage differentiation (CD33+ cells) in the nicotinamide-treated cultures (columns 2 and 3), moderate enhancement of myeloid lineage differentiation by FGF4 alone (columns 4-6) and absence of any significant effect of FGF4 on the nicotinamide-mediated inhibition of myeloid lineage hematopoietic cell differentiation (columns 7-12);

FIG. 38 is a bar graph showing the effect of nicotinamide with and without FGF4 on lymphoid lineage differentiation of ex-vivo expanded hematopoietic cells. Umbilical cord-derived progenitor (CD 133+) hematopoietic cells were isolated and cultured, with and without nicotinamide and FGF4, as in FIG. 35. After three weeks culture lymphoid lineage differentiated (CD19+) cells were stained and counted by FACS. Columns 1-12 as in FIG. 35. Note the striking inhibition of lymphoid lineage differentiation (CD19+ cells) in the nicotinamide-treated cultures (columns 2 and 3), absence of any significant effect on lymphoid lineage differentiation by FGF4 alone (columns 4-6) and absence of any significant effect of FGF4 on the nicotinamide-mediated inhibition of lymphoid lineage hematopoietic cell differentiation (columns 7-12);

DESCRIPTION OF SPECIFIC EMBODIMENTS OF THE INVENTION

The present invention, in some embodiments thereof, relates to methods of expanding mesenchymal stem cells and cell populations generated thereby.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The multipotent character of mesenchymal stem cells (MSCs) make these cells an attractive therapeutic tool and candidate for transplantation, capable of playing a role in a wide range of clinical applications in the context of both cell and gene therapy strategies. For example, mesenchymal stem cells may be used to enhance hematopoietic engraftment post-transplantation, to aid in tissue re-generation, to promote wound healing and to correct for a myriad of other inherited and acquired disorders. Efficient mesenchymal stem cell expansion protocols that do not have deleterious effects on the differentiation potential and target tissue engraftment potential of the cells are crucial to the success of any of these strategies.

In addition, MSCs are attractive for clinical therapy in regenerative medicine and inflammatory conditions due to their ability to differentiate, provide trophic support, and modulate the innate immune response. The therapeutic potential of MSC is being tested in multiple clinical trials for indications such as bone and cartilage repair, cardiac regeneration, critical limb ischemia, acute ischemic conditions, diabetes, Crohn's disease and graft vs host disease.

MSCs are immune-privileged and can be transplanted without the need for HLA matching between the donor and the recipient and therefore can be manufactured at large scale and marketed as an off-the-shelf cell product. The success of large scale batch production from one donor is highly dependent on donor and serum selection, the potential of seeded cells for prolonged expansion in culture and the duration of the manufacturing. Even though MSC multiply relatively easily in vitro, their proliferative potential is continuously decreased and their doubling time increases during culture. As a result, the successful manufacturing for commercialization of large batches of homogenous MSCs from one donor remains a challenge.

Whilst studying the effect of growth factors on MSC expansion, the present inventors found that growth factors such as basic FGF (bFGF), HB-EGF or platelet derived growth factor (PDGF) have a non-reproducible or even negative effect when cultured in the presence of nicotinamide on mesenchymal stem cell proliferation (FIGS. 1, 2, 6).

In sharp contrast, FGF4 surprisingly demonstrated a reproducible, synergistic activity together with nicotinamide on mesenchymal stem cell expansion/proliferation As illustrated in FIGS. 3A-D, the present inventors demonstrated that nicotinamide potentiates the effect of FGF4 on the proliferation of mesenchymal stem cells.

In addition, the present inventors demonstrated an unexpected effect of nicotinamide on cell size of mesenchymal stem cells cultured with FGF4.

As illustrated in FIGS. 4A-B, MSCs generated by culturing in nicotinamide and FGF4 are smaller than mesenchymal stem cells cultured according to identical methods, but in the presence of FGF4 alone and similar to MSC cultured with nicotinamide alone. For example, between days 10-32, the mesenchymal stem cells which are cultured in nicotinamide and FGF4 are less than about 20 μm in diameter, whereas cells grown in the presence of FGF4, but the absence of nicotinamide are greater than 20 μm in diameter. Thus, nicotinamide imposed an undifferentiated state on MSC cultured with FGF4.

Whilst further reducing the present invention to practice, the present inventors demonstrated that percent of cells expressing the MSC marker, CD105+CD45− is preserved in cultures treated with nicotinamide and FGF4 (FIGS. 5A-D).

Further, the present inventors have found that the use of nicotinamide during particular stages of the selection and expansion protocol was advantageous to mesenchymal stem cell populations. Thus, for example, seeding mesenchymal stem cells in the presence of nicotinamide and high calcium concentrations increased their seeding efficacy, as noted by analyzing marker phenotype of the cells (FIGS. 11-13).

Mesenchymal stem cells could be successfully expanded for at least six passages in the presence of nicotinamide without induction of differentiation, as illustrated by the surface marker composition of the cells (FIGS. 12A-C). Further, it was shown that nicotinamide promoted expansion of a more homogeneous, less granular population of MSCs (FIGS. 20A-C and 21A-B).

The present inventors experimentally showed that MSCs cultured with nicotinamide proliferate more rapidly and as a result, their doubling time (see FIG. 26) is decreased and the cultures reach confluence in a substantially shorter period of time (FIGS. 14-17, 26 and 27). The proliferative effect of nicotinamide was also demonstrated in large cultures of MSCs (FIG. 18). Further, the effect was not restricted to selected batches of serum (FIG. 19), a substantial advantage for the manufacturing of larger batches of MSCs. Yet further, the present inventors have shown that the proliferative effects of nicotinamide in combination with fibroblast growth factor 4 (FGF4) are not observed for stem cells of non-mesenchymal origin, for example, hematopoietic stem or progenitor cells (e,g, CD133+) (see Example 10, and FIGS. 35-38 herein). Indeed, FGF4 alone or in combination with nicotinamide was without any effect on proliferation or differentiation of ex-vivo cultured hematopoietic stem or progenitor cells (see FIGS. 35-38, lanes 1 and 4-12)

Thus, according to one aspect of the present invention there is provided a method of culturing mesenchymal stem cells (MSCs) comprising culturing a population of the MSCs in a medium comprising nicotinamide and fibroblast growth factor 4 (FGF4).

Yet further, the present inventors have now found that culturing a mixed population of mesenchymal stem cells in the presence of nicotinamide enhances the mesenchymal stem cell phenotype, such that subsequent selection or pre-selection with a mesenchymal stem cell marker provides for a more homogeneous population of mesenchymal stem cells, thereby providing a method for obtaining enriched populations of mesenchymal stem cell subsets. This was substantiated by the present inventors when they showed that culturing MSCs in the presence of nicotinamide increases expression of a particular adhesion molecule— Vascular cell adhesion protein 1 (VCAM1/CD106; see FIG. 24A). Conversely, the present inventors have shown that culturing MSCs in the presence of nicotinamide decreased expression of a marker for cell senescence (CD54; see FIG. 24B) thereby providing a method for obtaining enriched populations of mesenchymal stem cell by depleting the cell population for non-relevant cells.

The use of a selection or sorting step further enhances the stringency of sorting and selection specificity for MSCs and furthermore potentially reduces possible contamination from the starting material.

Thus, according to one aspect of the present invention there is provided a method of isolating mesenchymal stem cells (MSCs) from a mixed population of cells, comprising:

(a) culturing the mixed population of cells in a medium comprising nicotinamide; and (b) selecting cells based on the expression of a cell surface molecule from the mixed population of cells, thereby selecting MSCs from a mixed population of cells.

The term "mesenchymal stem cell" or "MSC" is used interchangeably for adult cells which are not terminally differentiated, which can divide to yield cells that are either stem cells, or which, irreversibly differentiate to give rise to cells of a mesenchymal cell lineage, e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines.

MSC cultures utilized by some embodiments of the invention preferably include three groups of cells which are defined by their morphological features: small and agranular cells (referred to as RS-1, hereinbelow), small and granular cells (referred to as RS-2, hereinbelow) and large and moderately granular cells (referred to as mature MSCs, hereinbelow). The presence and concentration of such cells in culture can be assayed by identifying a presence or absence of various cell surface markers, by using, for example, immunofluorescence, in situ hybridization, and activity assays.

When MSCs are cultured under the culturing conditions of some embodiments of the invention they exhibit negative staining for the hematopoietic stem cell markers CD34, CD11B, CD43 and CD45. A small fraction of cells (less than 10%) may be dimly positive for CD31 and/or CD38 markers. In addition, mature MSCs may be dimly positive for the hematopoietic stem cell marker, CD117 (c-Kit), moderately positive for the osteogenic MSCs marker, Stro-1 [Simmons, P. J. & Torok-Storb, B. (1991). Blood 78, 5562] and positive for the thymocytes and peripheral T lymphocytes marker, CD90 (Thy-1). On the other hand, the RS-1 cells are negative for the CD117 and Stro1 markers and are dimly positive for the CD90 marker, and the RS-2 cells are negative for all of these markers.

Mesenchymal cells cultured under the culturing conditions of some embodiments of the invention can secrete biologically active factors into the medium. The present inventors have observed that medium collected from mesenchymal cells cultured with nicotinamide comprises elevated levels of growth factors and cytokines (e.g. hepatocyte growth factor, keratinocyte growth factor, transforming growth factor beta) and reduced levels of pro-inflammatory factors (e.g. IL6) (see Example 8 and FIGS. 28-31). Addition of FGF4 to the medium further increased the levels of growth factors in the medium, whilst further reducing the levels of IL6 in the culture medium. Isolated culture medium was observed to have a strong anti-inflammatory effect, as well as enhancing proliferation of cells in culture. Thus, the mesenchymal cells cultured under the culturing conditions secrete biologically active factors having anti-inflammatory and cell proliferative-enhancing activity into the medium.

According to a preferred embodiment of this aspect of the present invention, the mesenchymal stem cells are human.

According to another embodiment of this aspect of the present invention, the mesenchymal stem cells are isolated from newborn humans.

Mesenchymal stem cells may be isolated from various tissues including but not limited to bone marrow, peripheral blood, blood, placenta (e.g. fetal side of the placenta), cord blood, umbilical cord, amniotic fluid, placenta and from adipose tissue.

A method of isolating mesenchymal stem cells from peripheral blood is described by Kassis et al [Bone Marrow Transplant. 2006 May; 37(10):967-76]. A method of isolating mesenchymal stem cells from placental tissue is described by Zhang et al [Chinese Medical Journal, 2004, 117 (6):882-887]. Methods of isolating and culturing adipose tissue, placental and cord blood mesenchymal stem cells are described by Kern et al [Stem Cells, 2006; 24:1294-1301].

Bone marrow can be isolated from the iliac crest of an individual by aspiration. Low-density BM mononuclear cells (BMMNC) may be separated by a FICOL-PAQUE density gradient or by elimination of red blood cells using Hetastarch (hydroxyethyl starch). Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, α medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 µg/ml streptomycin (GIBCO); and 2 mM L-glutamine (GIBCO).

Adipose tissue-derived MSCs can be obtained from any fat-containing tissue, for example, from epididymal fat or by liposuction and mononuclear cells can be isolated manually by removal of the fat and fat cells, or using the Celution System (Cytori Therapeutics) following the same procedure as described above for preparation of MSCs.

As mentioned, the method is effected by culturing (i.e. ex vivo or in vitro) the mesenchymal stem cells in a medium comprising nicotinamide and FGF4.

According to this aspect of the present invention, the cells are cultured under conditions that do not induce differentiation (e.g. in the absence of differentiation factors or in the presence of a non-differentiating amount of differentiating factors).

The present invention contemplates directly culturing mesenchymal stem cells following isolation from their source or culturing populations of cells that have been pre-selected for mesenchymal stem cells. Thus, the present invention contemplates culturing both heterogeneous populations of cells which comprise the MSCs and more homogeneous populations of cells, which have been enriched for MSCs, wherein more than 70%, more than 80%, more than 90% or more than 95%, more than 98% thereof are MSCs. Also, contemplated is the enriching for MSCs concomitant with the culturing as further described herein below.

It will be appreciated that the composition of the heterogeneous population of cells will be dependent on the source of the cells. Thus, for example, if the placenta is selected as the cell source, the heterogeneous population of cells will comprise placental cells as well as mesenchymal stem cells. If the bone marrow is selected as the cell source, the heterogeneous population of cells will comprise blood cells. However, as shown in Example 10, according to some embodiments of the present invention, culturing the mesenchymal stem cells under the culturing conditions of some embodiments of the invention (e,g, nicotinamide and FGF4 in combination) results in selective expansion of mesenchymal stem cell populations, while not having a concomitant proliferative effect on non-mesenchymal stem cell populations.

According to one method, the population of cells are cultured (in vitro or ex vivo) on polystyrene plastic surfaces (e.g. in a flask) so as to enrich for mesenchymal stem cells by removing non-adherent cells (i.e. non-mesenchymal stem cells). This method of enriching for MSCs may be effected prior to the culturing in nicotinamide and FGF4, concomitant with the culturing in nicotinamide and FGF4 and/or following the culturing in nicotinamide and FGF4.

Other methods of selecting for MSCs are known in the art including for example positive selection against mesenchymal stem cell markers and/or negative selection against hematopoietic stem and progenitor markers such as CD34, CD133, CD8, etc. Methods of determining protein cell-surface expression are well known in the art. Examples include immunological methods, such as, FACS analysis as well as biochemical methods (cell-surface labeling, e.g., radioactive, fluorescence, avidin-biotin).

It will be appreciated that a selecting stage may also be performed following the culturing in nicotinamide and FGF4. This may be effected as well as a preselection stage or instead of a preselection stage.

As used herein "nicotinamide" refers to nicotinamide as well as to products that are derived from nicotinamide, analogs thereof and metabolites of nicotinamide or nicotinamide analogs, such as, for example, NAD, NADH and NADPH.

As used herein, the phrase "nicotinamide analog" refers to any molecule that is known to act similarly to nicotinamide. Representative examples of nicotinamide analogs include, without limitation, benzamide, nicotinethioamide (the thiol analog of nicotinamide), nicotinic acid, α-amino-3-indole-propionic acid, and inhibitors of sirtuin family of histone/protein deacetylases.

Examples of nitotinamide analog derivatives include, but are not limited to substituted benzamides, substituted nicotinamides and nicotinethioamides and N-substituted nicotinamides and nicotinthioamides.

In a particular embodiment, the nicotinamide is supplied at a concentration of at least about 1 mM to 20 mM. In other embodiment, the nicotinamide concentration is supplied at a concentration of at least about 1 mM to 10 mM, e.g. about 2.5 mM, about 5 mM, about 7.5 mM.

Fibroblast growth factor 4, the FGF4 (map locus 11q13.3) gene product, FGF-4/HBGF-4/KFGF, is a 176 AA long protein derived by cleavage of the N-terminal 30 AAs of the precursor protein. FGF-4 contains a single N-linked glycosylation site. Unglycosylated FGF-4 is cleaved into two NH2-terminally truncated peptides (13 and 15 kDa) that are more active with higher heparin affinity than wild-type protein.

According to a particular embodiment, the FGF4 is human FGF4.

Recombinant FGF4 protein is commercially available (e.g. from Sigma Aldrich, where it is produced in baculovirus and cleaved at the N-terminal to yield a 148 AA protein; or from Invitrogen where it is produced in $E.\ coli$).

In a particular embodiment, the FGF4 is supplied to the culture at a concentration of at least about 1-1000 ng/ml. In other embodiment, the FGF4 concentration is supplied at a concentration of at least about 10-200 ng/ml, 10-100 ng/ml, e.g. about 50 ng/ml.

According to a particular embodiment, the culturing medium comprising both nicotinamide and FGF4 is devoid of additional growth factors such as PDGF, HB-EGF or bFGF (FGF2).

It will be appreciated that when referring to a medium being devoid of a particular component, the present invention contemplates that the medium comprises this component, but at a concentration which is below its minimal activity. Thus, for example, certain mediums may comprise trace amounts of the above described growth factors, however, the methods of the present invention relate to a medium being devoid of exogenously added growth factor beyond what is included in a commercial medium's formula, or that resulting from overall adjustment of medium component concentrations. Thus, according to a particular embodiment, the medium which comprises nicotinamide and FGF4 may comprise any one of the above mentioned additional growth factors but at a concentration less than 1 ng/ml.

A typical cell medium to which the nicotinamide and FGF4 may be added is Dulbecco's modified MEM (DMEM). Alternatively, the cell medium may be Ham's F12. Other contemplated mediums include HEM RPMI, F-12, and the like.

It will be noted that many of the culture media contain nicotinamide as a vitamin supplement for example, MEMα (8.19 μM nicotinamide), RPMI (8.19 μM nicotinamide), DMEM (32.78 μM nicotinamide) and Glascow's medium (16.39 μM nicotinamide), however, the methods of the present invention relate to exogenously added nicotinamide supplementing any nicotinamide and/or nicotinamide moiety included the medium's formula, or that resulting from overall adjustment of medium component concentrations.

In an embodiment of the invention, the cell culture medium has a high calcium concentration of more than about 1.8 mM, more than about 2 mM, or more than about 5 mM. It will be appreciated that the calcium concentration is calculated as the total calcium concentration including that already present in the culture medium.

Thus, for example, if the medium is Dulbecco's modified MEM (DMEM) (which already has a calcium ion concentration of about 1.8 mM), no additional calcium needs to be added. If the cell medium is Ham's F12 which has a calcium ion concentration of about 0.9 mM, additional calcium should be added so the total calcium concentration is above 1.8 mM. In one embodiment, the source of the additional calcium may be serum.

During the culturing, the medium can contain supplements required for cellular metabolism such as glutamine and other amino acids, vitamins, minerals and useful proteins such as transferrin, and the like. The medium may also contain antibiotics to prevent contamination with yeast, bacteria, and fungi, such as penicillin, streptomycin, gentamicin, and the like. If cells are to be cultured, conditions should be close to physiological conditions (preferably, a pH of about 6 to about 8, and a temperature of about 30° C. to about 40° C.).

Normoxia or hypoxia conditions are also contemplated.

According to one embodiment, the culture medium is devoid of serum (i.e. serum free medium) and comprises serum replacements including, but not limited to platelet lysate (during seeding and/or expansion).

According to still another embodiment the medium comprises about 10% fetal bovine serum. Human serum is also contemplated.

The culturing according to this aspect of the present invention may be effected for a limited amount of time, such that no expansion takes place (e.g. during the seeding stage only) or may be effected for longer periods of time so as to allow for mesenchymal stem cell expansion (i.e. cell propagation), thereby obtaining increased quantities thereof For each round of propagation, adherent cells may be harvested using trypsin/EDTA or by cell scraping, and dissociated by passage through a narrow Pasteur plastic pipette, and preferably replated at a density of about 100 to about 10,000 cells/cm².

According to this aspect of the present invention, a period of time sufficient for cell expansion may be taken to mean the length of time required for at least one cell to divide.

According to one embodiment, the culturing is effected for at least one day, at least two days, at least three days, at least four days, at least five days, at least six days, at least one week, at least two weeks, at least three weeks, at least four weeks or at least five weeks.

According to another embodiment, the culturing is not effected for more than ten weeks.

According to still another embodiment, the cells are allowed to expand for at least two population doublings, at least four population doublings, at least six population doublings, at least eight population doublings, at least ten population doublings, at least 15 population doublings, at least 20 population doublings, at least 25 population doublings, at least 30 population doublings, at least 35 population doublings, at least 40 population doublings, or at least 45 population doublings.

According to another embodiment, the cells are not allowed to expand for more than 50 population doublings.

The present invention contemplates additional methods of mesenchymal stem cell expansion as well as (or instead of) culturing in nicotinamide and FGF4.

Since the present inventors have found that when at least a portion of the time of the expansion process is effected in the presence of nicotinamide, increased numbers of mesenchymal stem cells are obtained, preferably additional methods of expansion include culturing in the presence of nicotinamide.

Thus, according to another aspect of the present invention there is provided a method of expanding a population of mesenchymal stem cells, the method comprising culturing a seeded population of mesenchymal stem cells for a period of time sufficient for cell expansion, wherein for at least a portion of the period of time the culturing is effected in a medium devoid of nicotinamide; and for at least a second portion of the period of time, the culturing is effected in a medium comprising nicotinamide and FGF4, thereby generating an expanded population of mesenchymal stem cells.

The term "expanding" as used herein refers to increasing the number of cells in the cell population due to cell replication.

According to this aspect of the present invention, the cells are expanded under conditions that do not induce differentiation (e.g. in the absence of differentiation factors).

The seeded population of undifferentiated mesenchymal stem cells may be a heterogeneous population of cells or a purified population of mesenchymal stem cells, as further described herein above.

As mentioned, a medium being devoid of nicotinamide refers to a medium comprising less than the minimal effective amount of nicotinamide (e.g. less than 0.5 mM, or more preferably less than 0.05 mM). Thus mediums comprising trace amounts of nicotinamide (as described herein above) may be used for this aspect of the present invention. Thus, according to a particular embodiment, the medium without exogenously added nicotinamide may comprise, before the addition of exogenous nicotinamide as a supplement, nicotinamide at a concentration less than 0.5 mM or more preferably less than 0.05 mM.

According to one embodiment, the MSCs are at least 50% purified, at least 75% purified or at least 90% purified.

The population of mesenchymal stem cells may be seeded (and also cultured) in any medium including those described herein above or those disclosed in U.S. Patent Application No. 20050260748, incorporated herein by reference.

The time ratio of culturing in the presence of nicotinamide and FGF4: culturing in the absence of nicotinamide may vary and may include all ratios from 1:99; 2:98; 3:97; 4:96; 5:95; 6:94; 7:93; 8:92; 9:91; 10:90; 11:89; 12:88; 13:87; 14:86; 15:85; 16:84; 17:83; 18:82; 19:81; 20:80; 21:79; 22:78; 23:77; 24:76; 25:75; 26:74 27:73; 28:72; 29:71; 30:70; 31:69; 32:68; 33:67; 34:66; 35:65; 36:64; 37:63; 38:62; 39:61; 40:60; 41:59; 42:58; 43:57; 44:56; 45:55;

46:54; 47:53; 48:52; 49:51; 50:50; 51:49; 52:48; 53:47; 54:46; 55:45; 56:44; 57:43; 58:42; 59:41; 60:40; 61:39; 62:38; 63:37; 64:36; 65:35; 66:34; 67:33; 68:32; 69:31; 70:30; 71:29; 72:28; 73:27; 74:26; 75:25; 76:24; 77:23; 78:22; 79:21; 80:29; 81:19; 82:18; 83:17; 84:16; 85:15; 86:14; 87:13; 88:12; 89:11; 90:10; 91:9; 92:8; 93:7; 94:6; 95:5; 96:4; 97:3; 98:2; 99:1.

According to one embodiment, at least one full round of propagation is effected in the presence of nicotinamide.

It will be appreciated that the culturing in the medium comprising nicotinamide may be effected prior or following the culturing in the medium devoid of nicotinamide.

According to embodiments of the present invention, the medium which is devoid of nicotinamide comprises FGF4 (either at the same or a different concentration as the medium which comprises nicotinamide).

According to other embodiments of the present invention, the medium which is devoid of nicotinamide is further devoid of FGF4.

Further, the present inventors contemplate more than one culturing stage in the presence of nicotinamide and FGF4 interspersed with culturing stages in the absence of the nicotinamide and vice versa.

According to one embodiment, the culturing in the presence of nicotinamide and FGF4 is effected for at least one day, at least two days, at least three days, at least four days, at least five days, at least six days, at least one week, at least two weeks, at least three weeks, at least four weeks or at least five weeks.

According to another embodiment, the culturing in the absence of nicotinamide is effected for at least one day, at least two days, at least three days, at least four days, at least five days, at least six days, at least one week, at least two weeks, at least three weeks, at least four weeks or at least five weeks.

As mentioned, the second step of the purification process is selecting for MSCs based on the expression of a mesenchymal stem cell surface marker. The selection or sorting step may comprise selecting mesenchymal stem cells (MSC) from the mixed population of cells by means of one or more of such surface markers. The use of a selection or sorting step further enhances the stringency of sorting and selection specificity for MSCs and furthermore potentially reduces possible contamination from the starting material.

Prior to sorting, the mixed cell populations are typically dispersed using cell dispersing agents. Preferably single cell populations are obtained. Examples of agents that may be used to disperse the cells include, but are not limited to collagenase, dispase, accutase, trypsin (e.g. trypsin-EDTA), papain. Alternatively, or additionally trituration may also be performed to increase the dispersal of the cells.

According to a specific embodiment, the selecting is effected by selecting cells which express VCAM-1/CD106 (NP_001069.1) above a predetermined level.

According to another embodiment, the selecting is effected by selecting cells which express at least one of CD105 (SH2), CD73 SH3/4), CD44, CD90 (Thy-1), CD71, STRO-1, CD29, CD166, CD146, CD106 and CD271 above a predetermined level.

According to a particular embodiment, the surface marker is stromal precursor antigen-1 (STRO-1), CD105 or VCAM (CD106).

According to still another embodiment, the selecting is effected by selecting cells which express at least one of CD34, CD11B, CD43 and CD45 below a predetermined level.

A number of methods are known for selection or sorting based on antigen expression, and any of these may be used in the selection or sorting step described here. In particularly preferred embodiments, the analysis is achieved using a flow cytometer and the cells are subsequently sorted based upon the specific light scattering and fluorescent characteristics of each cell. Thus, the selection or sorting may be achieved by means of fluorescence activated cell sorting (FACS).

As is known in the art, FACS involves exposing cells to a reporter, such as a fluorescently labelled antibody, which binds to and labels antigens expressed by the cell. Methods of production of antibodies and labelling thereof to form reporters are known in the art, and described for example in Harlow and Lane. Antibodies that may be used for FACS analysis are taught in Schlossman S, Boumell L, et al, [Leucocyte Typing V. New York: Oxford University Press; 1995] and are widely commercially available. The cells are then passed through a FACS machine, which sorts the cells from each other based on the labeling.

Alternatively or in addition, magnetic cell sorting (MACS) or immunopanning may be employed to sort the cells.

As mentioned hereinabove, the mixed cell populations are analyzed by a Flow Cytometer, such as a laser scanning Cytometer. A Flow Cytometer typically consists of a laser light source, flow measurement chamber, and an optical system consisting of lenses, filters, and light detectors. Two photo-multiplier tubes (light detectors), one at 180 degrees and one at 90 degrees to the laser, are used to measure forward (FSC) and right-angle scatter (SSC), respectively. Three fluorescence detectors, each consisting of a filter and photomultiplier tube, are used to detect fluorescence. The three detectors sense green (FL1—530 nm), orange (FL2—585 nm), and red fluorescence (FL3—650 nm). Cells are identified by sort logic applied to all five of the detector signals (FSC, SSC, FL1, FL2, FL3) using a computer.

Exemplary Flow Cytometers that may be used in this aspect of the present invention are manufactured by companies such as Becton Dickinson (USA), Backman Coulter (USA), Partec (Germany).

The FACS machine may be set such that cells of a particular forward scatter and/or side scatter are selected. Forward-scattered light (FSC) is proportional to cell-surface area or size. FSC is a measurement of mostly diffracted light and is detected just off the axis of the incident laser beam in the forward direction by a photodiode. FSC provides a suitable method of detecting particles greater than a given size independent of their fluorescence.

Side-scattered light (SSC) is proportional to cell granularity or internal complexity. SSC is a measurement of mostly refracted and reflected light that occurs at any interface within the cell where there is a change in refractive index. SSC is collected at approximately 90 degrees to the laser beam by a collection lens and then redirected by a beam splitter to the appropriate detector.

Thus, for example, the present invention contemplates selecting cells which have a diameter below about 20 µm, by gating at a particular forward scatter and a particular granularity by gating at a particular side scatter.

The present invention contemplates selecting particular cell populations based on the level of cell surface expression. Thus, in the case of FACS, the machine may be set such that cell populations gated for events stained with a fluorescent intensity between about 20-100 (dim), between about 100-500 (moderate) or between about 500-2000, or greater (bright). The following cell populations are contemplated by the present invention:

VCAM1 bright cells;
VCAM1 moderate cells;
VCAM1 dim cells;
STRO-1 bright cells;
STRO-1 moderate cells;
STRO-1 dim cells;
CD105 bright cells;
CD105 moderate cells;
CD 105 dim cells;

It will be appreciated that cell populations may be selected based on expression of more than one of the above mentioned markers—e.g. at least two of the above mentioned markers or at least three of the above mentioned markers.

The above described cell populations are typically enriched for cells that do not express CD45. Thus, according to another embodiment, less than 10% of the cells in the above described cell populations express CD45 as measured by FACS.

According to still another embodiment, more than 90% of the cells in the above described cell populations express CD90, as measured by FACS.

According to still another embodiment, more than 95% of the cells in the above described cell populations express CD90, as measured by FACS.

According to still another embodiment, more than 90% of the cells in the above described cell populations express CD44, as measured by FACS.

According to still another embodiment, more than 95% of the cells in the above described cell populations express CD44, as measured by FACS.

As mentioned, additional steps are contemplated by the present inventors prior to, during or following the two step protocol described herein. Such additional steps may involve culturing on a plastic surface, as described herein above and/or additional expansion steps, for example, as described herein above re culturing in nicotinamide.

In some embodiments, the cells are selected according to cell size, for example, by a cell counter based on Trypan Blue exclusion and graphical analysis. Suitable cell counters include, but are not limited to Cedex counters (Roche Innovatis). The number of cells that may be cultured according to any of the methods of the present invention may be any number including small batches—e.g. $100 \times 10^4$ cells to larger batches—e.g. $100 \times 10^{12}$ or $100 \times 10^{13}$ cells.

When large batches are required, the cells are typically cultured in a bioreactor (or in multi-level industrial flasks), the size of which is selected according to the number of cells being cultured.

Examples of flasks and plates that may be used for growing MSCs in commercial quantities include for example Corning HYPERFlask™ Cell Culture Vessel, Corning CellSTACK™ Chambers, Corning HYPERStack™ Cell Culture Vessel, 40 stack chambers and NUNC Automatic Cell Factory Manipulator.

As used herein, the term "bioreactor" refers to any device in which biological and/or biochemical processes develop under monitored and controlled environmental and operating conditions, for example, pH, temperature, pressure, nutrient supply and waste removal. According to one embodiment of the invention, the basic classes of bioreactors suitable for use with the present invention include static bioreactors, stirred flask bioreactors, rotating wall bioreactors, hollow fiber bioreactors and direct perfusion bioreactors, as further described in WO 2005/007799, the contents of which are incorporated by reference.

The cultured population of cells generated using the methods described herein may be further treated following the culturing or stored (e.g. cryopreserved) in the presence of a cryopreservant. Such cryopreservants include dimethyl sulfoxide (DMSO), glycerol, and the like.

The cell populations generated following the culturing and/or the expansion method of the present invention may be used for a variety of purposes including research, for screening agents which affect the differentiation thereof and for therapeutic uses. Additionally, or alternatively, the cell populations may be stored (e.g. frozen) until required.

According to one embodiment, the mesenchymal stem cell populations generated using the methods disclosed herein may be used for further differentiation protocols.

Methods of differentiating mesenchymal stem cells towards various cell lineages are known in the art.

Differentiating cells may be obtained by culturing or differentiating MSC in a growth environment that enriches for cells with the desired phenotype, e.g. osteoblasts, adipocytes, etc. The culture may comprise agents that enhance differentiation to a specific lineage.

Osteogenic differentiation may be performed by plating cells and culturing to confluency, then culturing in medium comprising .beta.-glycerol phosphate, ascorbic acid and retinoic acid (see Cowan et al. (2005) Tissue engineering 11, 645-658).

To induce adipogenic differentiation detached cells may be reseeded in 24 well plates ($7 \times 10^4$ cells/ml) and treated with adipogenic medium for three weeks. Two exemplary adipogenic mediums are provided: DMEM supplemented with 0.05 mg/ml Gentamicin, 2 mM L-glutamine, 10% FBS, 0.5 μM 3-isobutyl-1-methylxanthine (IBMX, Sigma), 0.5 μM hydrocortisone (Sigma) and 60 μM indomethacin (Sigma), or MSC adipogenic stimulatory supplements purchased from StemCell Technologies, as per manufacturer's instructions. Adipogenic differentiation may be assessed by oil-red staining: cells are fixed with methanol at −20° C. for 10 minutes and treated with 60% isopropanol for 3 minutes. Plates may be stained in oil-red-0 (Sigma) for 10 minutes and rinsed in tap water. After rinsing plates may be counterstained with Mayer hematoxylin (Sigma) for 1 minute and rinsed in tap water.

Myocyte differentiation may be performed by plating cells and culturing to confluency, then culturing in medium comprising horse serum, dexamethasone, and hydrocortisone (see Eun et al. (2004) Stem Cells 22:617-624); or 5-azacytidine (see Fukuda et al. (2001) Artificial Organs 25:187).

Chondrocyte differentiation may be performed by plating cells and culturing to confluency, then culturing in medium comprising dexamethasone, ascorbic acid 2-phosphate, insulin, transferrin, selenous acid, with or without TGF-$\beta_1$ (see Williams et al. (2003) Tissue Engineering 9(4):679).

Neuronal differentiation is known in the art. For example, generation of neurons and or oligodendrocytes from mesenchymal stem cells may be effected as described in U.S. Patent No. 20100021434 and 20090257987.

Alternatively, or additionally, the mesenchymal stem cells may be genetically modified so as to express an agent (e.g. a polypeptide, siRNA or miRNA) that is useful for treating a disease or alternatively that drives its differentiation towards a certain lineage.

Thus, for example, the mesenchymal stem cells may be genetically modified to express bone morphogenic factor 2 (BMP2) in order to promote differentiation into bone.

Alternatively, the mesenchymal stem cells may be genetically modified to express Pd-x in order to promote differentiation into pancreatic cells.

Since mesenchymal stem cells are known to home and migrate towards wounds, the cells may be used as carriers, transporting useful molecules to the site of injury. The useful molecules may be molecules that are inherently found inside the mesenchymal stem cells (e.g. growth factors) or may be artificially placed inside the cells (i.e. proteins or polynucleotides transfected into the cells).

Both the differentiated and non-differentiated mesenchymal stem cell populations described herein may be used to treat a myriad of disorders, the particular disorders being selected according to the differentiation status of the cells.

Thus, according to another aspect of the present invention there is provided a method of treating a disease or disorder, the method comprising transplanting to a subject in need thereof a therapeutically effective amount of the isolated population of cells the present invention.

According to one embodiment, the disease or disorder is selected from the group consisting of a bone or cartilage disease, a neurodegenerative disease, a cardiac disease, a hepatic disease, cancer, nerve damage, wound healing, autoimmune disease, graft versus host disease, spinal cord injury and tissue regeneration.

Bone defects suitable for treatment using the cells of the present invention include, but are not limited to osteogenesis imperfecta, fracture, congenital bone defects, and the like.

Further, the mesenchymal stem cells of the present invention can be implanted in a subject to provide osseous and connective tissue support of orthopedic and other (e.g. dental) prosthetic devices, such as joint replacements and/or tooth implants.

The mesenchymal stem cells of the present invention can be used to treat CNS diseases.

Representative examples of CNS diseases or disorders that can be beneficially treated with the cells described herein include, but are not limited to, a pain disorder, a motion disorder, a dissociative disorder, a mood disorder, an affective disorder, a neurodegenerative disease or disorder and a convulsive disorder.

More specific examples of such conditions include, but are not limited to, Parkinson's, ALS, Multiple Sclerosis, Huntingdon's disease, autoimmune encephalomyelitis, diabetic neuropathy, glaucomatous neuropathy, macular degeneration, action tremors and tardive dyskinesia, panic, anxiety, depression, alcoholism, insomnia, manic behavior, Alzheimer's and epilepsy.

As mentioned, since MSCs can differentiate into cartilage, the mesenchymal stem cells of the present invention may be suitable for the treatment of joint conditions including, but not limited to osteoarthritis, rheumatoid arthritis, inflammatory arthritis, chondromalacia, avascular necrosis, traumatic arthritis and the like.

Bone marrow-derived mesenchymal stem cells (MSCs) are known to interact with hematopoietic stem cells (HSCs) and immune cells, and represent potential cellular therapy to enhance allogeneic hematopoietic engraftment and prevent graft-versus-host disease (GVHD). When hematopoietic stem cell numbers were limited, human engraftment of NOD-SCID mice was observed only after co-infusion of unrelated human MSCs, but not with co-infusion of mouse mesenchymal cell line. Unrelated human MSCs did not elicit T-cell activation in vitro and suppressed T-cell activation by Tuberculin and unrelated allogeneic lymphocytes in a dose-dependent manner. Cell-free MSC culture supernatant, mouse stromal cells and human dermal fibroblasts did not elicit this effect. These preclinical data suggest that unrelated, human bone marrow-derived, culture-expanded MSCs may improve the outcome of allogeneic transplantation by promoting hematopoietic engraftment and limiting GVHD (Maitra B, et al Bone Marrow Transplant. 2004 33(6):597-604).

It is known that when MSCs are introduced into the infarcted heart, they can prevent deleterious remodeling and improve recovery. MSCs have been injected directly into the infarct, or they have been administered intravenously and seen to home to the site of injury. Examination of the interaction of allogeneic MSCs with cells of the immune system indicates little rejection by T cells. Persistence of allogeneic MSCs in vivo suggests their potential "off the shelf" therapeutic use for multiple recipients (Pittenger M F, et al Circ Res. 2004 Jul. 9; 95(1):9-20).

The use of ex-vivo expanded mesenchymal cells for transplantation has the following advantages:

It reduces the volume of blood or other tissue required for reconstitution of a recipient adult tissue system.

It enables storage of small number of unexpanded mesenchymal cells, for example, form cord blood or peripheral blood, for potential future use.

In the case of autologous transplantation of recipients with malignancies, contaminating tumor cells in autologous infusion often contribute to the recurrence of the disease. Selecting and expanding mesenchymal cells will reduce the load of tumor cells in the final transplant.

Tissue regeneration: Mesenchymal cell populations of the present invention can be used for the promotion of tissue regeneration. Transplantation of mesenchymal stem cells has great promise for benefits in regenerative medicine, autoimmune diseases, inflammatory conditions, acute and chronic ischemic conditions reconstructive surgery, tissue engineering, regenerating new tissues and naturally healing diseased or injured organs.

Gene therapy: For successful long-term gene therapy, a high frequency of genetically modified cells with transgenes stably integrated within their genome is an obligatory requirement. Presently, gene transfer into fresh stem and/or progenitor cells is highly inefficient. The ability to store and process a selected population of mesenchymal cells ex-vivo, and enhance their homing and engraftment potential would provide for an increased probability of the successful use of genetically modified cell transplantation [Palmiter Proc Natl Acad Sci USA 91(4): 1219-1223, (1994)].

In any of the methods described herein the cells may be obtained from an autologous, semi-autologous or non-autologous (i.e., allogeneic or xenogeneic) human donor or embryo or cord/placenta. For example, cells may be isolated from a human cadaver or a donor subject.

The term semi-autologous refers to donor cells which are partially-mismatched to recipient cells at a major histocompatibility complex (MHC) class I or class II locus.

The cells of the present invention can be administered to the treated individual using a variety of transplantation approaches, the nature of which depends on the site of implantation.

According to one embodiment, the cells are not transplanted into the body in a medium comprising nicotinamide.

The cells may be transplanted to a damaged or healthy region of the tissue. In some cases the exact location of the damaged tissue area may be unknown and the cells may be inadvertently transplanted to a healthy region. In other cases, it may be preferable to administer the cells to a healthy region, thereby avoiding any further damage to that region.

Whatever the case, following transplantation, the cells preferably migrate to the damaged area.

The term or phrase "transplantation", "cell replacement" or "grafting" are used interchangeably herein and refer to the introduction of the cells of the present invention to target tissue. As mentioned, the cells can be derived from the recipient or from an allogeneic, semi-allogeneic or xenogeneic donor. Other xeno-origins are also contemplated.

Cells of the present invention may be transplanted by means of direct injection into an organ, injection into the bloodstream, intraperitoneal injection, injection directly to lymphoid organs etc. Suitable methods of transplantation can be determined by monitoring the homing and engraftment of the implanted cells to the desired organ, the expression of desired organ-specific genes or markers, and the function of the derived organ of the subject. In the pancreas, for example, maintenance of euglycemia, secretion of insulin and/or C peptide can be a measure of the restoration of function to a diabetic host animal following cell replacement therapy as disclosed hereinbelow. In the liver, for example, albumin synthesis can be monitored.

MSCs typically down regulate MHC class 2 and are therefore less immunogenic. Embryonal or newborn cells obtained from the cord blood, cord's Warton's jelly or placenta are further less likely to be strongly immunogenic and therefore less likely to be rejected, especially since such cells are immunosuppressive and immunoregulatory to start with.

Notwithstanding, since non-autologous cells may induce an immune reaction when administered to the body several approaches may be taken to reduce the likelihood of rejection of non-autologous cells. These include either administration of cells to privileged sites, or alternatively, suppressing the recipient's immune system, providing anti-inflammatory treatment which may be indicated to control autoimmune disorders to start with and/or encapsulating the non-autologous/semi-autologous cells in immunoisolating, semipermeable membranes before transplantation. Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly (allylamine alpha-cyanocinnamylideneacetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 .mu.m. Such microcapsules can be further encapsulated with additional 2-5 .mu.m ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400.mu.m (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE™), etanercept, TNF alpha blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Cell populations of the present invention can be provided per se, along with the culture medium containing same, isolated from the culture medium, and combined with a pharmaceutically acceptable carrier as well as with additional agents which may promote cell engraftment and/or organ function (e.g., immunosuppressing agents, antibiotics, growth factor). Hence, cell populations of the invention can be administered in a pharmaceutically acceptable carrier or diluent, such as sterile saline and aqueous buffer solutions. The use of such carriers and diluents is well known in the art.

Compositions of the present invention may, if desired, be presented in a pack or dispenser device, such as an FDA-approved kit, which may contain one or more unit dosage forms containing the active ingredient (e.g., cells). The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

The cells prepared according to the methods of the present invention can be administered to the subject per se, seeded on a scaffold and/or in a pharmaceutical composition where it is mixed with suitable carriers or excipients.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Various embodiments and aspects of the present invention as delineated hereinabove and as claimed in the claims section below find experimental support in the following examples.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat.

Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Examples

Methods and Experimental Procedures

Mesenchymal Stem Cells Isolation:

Bone marrow derived and adipose tissue derived mesenchymal cells were isolated based on their plastic adherence potential in expansion medium containing: High glucose DMEM and 10% Fetal Bovine Serum (FBS, Hyclone, Logan, Utah, USA) supplemented with 0.05 mg/ml Gentamicin (Sigma) and 2 mM L-glutamine (Biological Industries, Israel). Cells were allowed to adhere for 3-4 days and non-adherent cells were washed out with medium changes. The medium was further exchanged with fresh medium every 3-4 days.

Hematopoietic Stem and Progenitor Cells:

Umbilical cord-derived hematopoietic stem cells were isolated using CD133 microbeads and CliniMACS® separator (Miltenyi, Inc. Auburn, Calif.), and cultured for 3 weeks in MEMα supplemented with 50 ng/ml TPO, IL6, SCF, Flt3, fetal bovine serum, ±2.5 or 5 mM nicotinamide, and/or 10, 50 or 200 ng/ml FGF4. After 3 weeks in culture the cells were stained for surface markers (CD38, CD133, CD33, CD19) and the cell populations determined by FACS analysis (see below). Results are expressed as percentage of total population assayed.

Maintenance and Expansion:

Once adherent cells reached approximately 80-90% confluency, they were detached with 0.25% trypsin-EDTA (Sigma), washed twice in DMEM and 10% Fetal Bovine Serum, with centrifugation, 400 g, 5 minutes, and replated at a 1:2 to 1:1000 dilution under the same culture conditions.

Measurement of Cell Size:

Cell size was measured using Cedex Automated Cell Counter (Innovatis). The cells were diluted 1:2 in Trypan Blue (Sigma) and cell size was measured automatically under microscope.

Measurement of Granularicity:

Following trypsin treatment, the cells were analyzed for granularicity by side scatter FACS.

Measurement of Number of Cells in Culture:

Cell number was measured using Cedex Automated Cell Counter (Innovatis). The cells were diluted 1:2 in Trypan Blue (Sigma) and cell number was measured automatically under microscope.

Surface Antigen Analysis:

At different time points the cells were detached with 0.25% trypsin-EDTA. The cells were washed with a PBS solution containing 1% BSA, and stained (at 4° C. for 30 min) with either fluorescein isothiocyanate (FITC) or phycoerythrin (PE)-conjugated antibodies: 105 PE, 105 FITC (Serotec, Raleigh, N.C.), 45 FITC, 14 FITC, HLA-DR FITC, 106 PE, 31 PE (BD, Franklin Lakes N.J.), 34 PE (Dako, Glostrup, Denmark), 73 PE, HLA class1 PE, 49b PE (Pharmingen, San Diego, Calif.), 29 PE, 44 PE, 54 FITC, 59 PE, 90 PE (BioLegend, San Diego, Calif.). CD133— (AC141) PE (Miltenyi, Auburn, Calif.), CD38 FITC (Dako, Glostrup, Denmark), CD19 FITC (BD Biosciences, Franklin Lakes N.J.), CD33 FITC (BD Bioscience, Franklin Lakes N.J.).

The cells were then washed in the above buffer and analyzed using a FACScalibur® flow cytometer (Becton Dickinson, Franklin Lakes N.J.). The cells were passed at a rate of up to 1000 cells/second, using a 488 nm argon laser beam as the light source for excitation. Emission of 10000 cells was measured using logarithmic amplification, and analyzed using the CellQuest software (Becton Dickinson). Cells stained with FITC- and PE-conjugated isotype control antibodies were used to determine background fluorescence.

CFU-F Assay:

Cultured MSCs were seeded in 6-well plates at density of 50-100 cells/cm$^2$ and maintained with DMEM and 10% FBS. After 14 days the cells were fixed using 10% cold Formalin (Sigma) and stained with Harris Hematoxylin (Sigma). Clones (cluster of more than 50 cells with evident epicenter) are stained blue-purple and counted using microscope.

Senescence Evaluation Assay:

Cultured MSCs were stained using the Senescence beta-Galactosidase Staining Kit (Cell Signaling). The cells are fixed and stained for detection of beta-Galactosidase activity at pH 6 using X-Gal and incubation overnight in 37° C. in dry incubator.

In-Vitro Wound Healing Assay:

Wound was performed in MSCs cultures at ~70% confluence using 200 μl or 1000 μl tip. Four days later the cells were fixated using 10% cold Formalin (Sigma) and stained with Harris Hematoxylin (Sigma). The in-vitro wound healing process was evaluated using microscope.

Treatment of Mesenchymal Cultures with Nicotinamide:

Mesenchymal cultures were initiated as described above, and supplemented with nicotinamide 1-15 mM alone, or in combination with growth factors or growth factors alone, incubated at 37° C. in a humidified atmosphere of 5% $CO_2$ in air. At each passage and at each medium exchange, the cultures were supplemented with mesenchymal medium, nicotinamide and growth factors.

In some experiments, the adherent cells were cultured with or without nicotinamide and indicated factors, and 24 hours before passage 4, and the medium replaced with medium without fetal bovine serum or FGF4.

In Vitro Migration Assay:

RPMI plus 10% FCS (0.6 ml) containing 100 ng/ml CXCL12 (R&D Systems) was placed into the lower chamber of a Costar 24-well "transwell" culture plate (Corning, Inc, Corning, N.Y.). Cells ($2\times10^5$) in 100-µl medium were introduced into the upper chamber, over a porous membrane (pore size, 5 µm). After 4 hours, cells were collected from both chambers and counted by flow cytometry (FACSsort, Becton Dickinson and Co, San Jose, Calif., USA). Spontaneous migration was performed as a control without CXCL12 in the lower chamber.

In Vivo Analysis of Homing:

NOD/SCID mice (8-10 week old) (Harlan Ltd., Israel) were sub-lethally irradiated (at 375cGy at 67cGy/min) and 24 hours later inoculated via the tail vein with either CFSE-labeled mesenchymal stem cells cultured in the presence of nicotinamide or CFSE-labeled mesenchymal stem cells cultured in the absence of nicotinamide. Mice were sacrificed at 24 hours post injection and bone marrow or other tissue samples were obtained. Homing of human cells was detected by flow cytometry via visualization of CFSE-stained cells over a background of unlabeled murine cells. The bright fluorescence of CFSE is sufficient to separate labeled human cells from unlabeled murine cells by at least 1 log. To quantify homing of human progenitor cells, bone marrow cells were stained with APC-conjugated antihuman cell marker monoclonal antibodies and CFSE$^+$/cell marker cells were enumerated. For each sample 100,000 events are recorded and analyzed.

Transplantation of Mesenchymal Cells into NOD/SCID Mice:

NOD/SCID mice were bred and maintained in sterile intra-ventilated cages (Techniplast, Bugugiatte, Italy). Eight-week-old mice were sub-lethally irradiated as described above. Mice were inoculated via the tail vein with mesenchymal cells cultured in the presence or absence of nicotinamide. To avoid donor variability, mesenchymal cells from several units were pooled and used for expansion cultures as well as group injection. Mice were sacrificed at week 4, and marrow samples were obtained by flushing their femurs and tibias with IMDM at 4° C. Flow cytometric analysis of NOD/SCID marrow cells was performed as described hereinabove, using monoclonal antibodies against human cell surface differentiation antigens to identify human cell engraftment.

Delayed Type Hypersensitivity Assay:

BALB/C mice were sensitized with Oxazolone (4-ethoxymethylene-2-phenyloxazol-5-one), and 6 days later challenged with Oxazolone, injected into the ear. Immune modulation by candidate compositions, as indicated, was determined 24 hours following their topical administration, by measurement of ear thickness with a caliper.

Growth Factor Secretion:

Medium from MSC cultured as indicated, and depleted of fetal bovine serum and FGF4 24 hours before passage 4 was collected and assayed by ELISA for growth factors and immune-related factors secreted into the medium (human growth factor HGF, transforming growth factor beta TGF-β, keratinocyte growth factor KGF and interleukin 6 IL-6). ELISA was carried out using solid phase sandwich ELISA kits specific for human KGF (R&D systems, cat#DKG00), IL-6 (R&D systems, cat#D6050), TGF-β1 (R&D systems, cat#DB100B), HGF (R&D systems, cat#DHG00).

Keratinocyte Proliferation Assay:

Normal human epidermal keratinocytes (Promocell, GmbH, Heidelberg, Germany) were cultured for one passage in keratinocyte growth medium, detached and reseeded in keratinocyte growth medium (containing 50% Supplement Mix) diluted, as indicated, with MSC conditioned medium. Medium was changed twice a week, and keratinocytes detached and counted after reaching 90% confluence.

Mixed Lymphocyte Reaction-Like Assay:

Peripheral blood derived mononuclear cells (MNCs), containing greater than 50% T-cells, were isolated by buoyant density centrifugation and activated with 3 µg/ml phytohemagglutinin (PHA). Following activation, the cells were cultured with or without conditioned medium from MSC culture and other factors. Response of the PBMN cells to the activation by PHA was measured by the extent of TNF-alpha secretion into the medium cell (pg/ml), 72 hours after initial activation, measured by ELISA.

Statistics—

The non-parametric Wilcoxon Rank Test was applied for testing differences between the study groups. All the tests applied were two-tailed, and a p value of ≤5% was considered statistically significant. The data were analyzed using SAS software (SAS Institute, Cary, N.C.).

Example 1

Analyzing of Nicotinamide on Mesenchymal Stem Cells Cultured in the Presence of Growth Factors Materials and Methods Mesenchymal stem cells were selected and cultured in the presence of particular growth factors (basic fibroblast growth factor—bFGF, heparin binding epidermal growth factor—HB-EGF, fibroblast growth factor 4—FGF-4 and platelet derived growth factor, homodimer, subunit B, PDGF-BB) in the presence and absence of nicotinamide for three or four passages and the number and size of the cells was calculated.

Two concentrations (10 and 50 ng/ml) of each one of the following factors were examined.

The experimental groups were as follows:
Group 1: Ctrl
Group 2: 10 ng/ml growth factor
Group 3: 50 ng/ml growth factor
Group 4: 5 mM NAM
Group 5: 5 mM NAM+10 ng/ml growth factor
Group 6: 5 mM NAM+50 ng/ml growth factor In addition, the influence of the combination: 5 mM NAM+50 ng/ml FGF4+50 ng/ml PDGF-BB was examined in comparison to an individual supplement.

Results

FIG. 1 illustrates that basic FGF has a negative effect on the ability of nicotinamide to increase proliferation of mesenchymal stem cells.

FIGS. 2A-B illustrate that heparin-binding EGF-like growth factor (HB-EGF) has a negative effect on the ability of nicotinamide to increase proliferation of mesenchymal stem cells.

FIGS. 3-5 illustrate that nicotinamide has a potentiating effect on the ability of FGF4 to increase proliferation of mesenchymal stem cells.

FIGS. 6A-D illustrate that PDGF-BB has an inconsistent effect on the ability of nicotinamide to increase proliferation of mesenchymal stem cells.

FIGS. 7A-D illustrate that MSC cultures treated with PDGF-BB or a combination of PDGF-BB+NAM are contaminated with a higher fraction of cells other than MSCs as compared with cultures treated without PDGF-BB.

FIGS. 8A-B, 9A-B and 10A-H illustrate that the combination of three factors—FGF4, nicotinamide and PDGF-BB has a detrimental effect on proliferation of mesenchymal stem cells as compared to the effect of FGF4 and nicotinamide in the absence of PDGF-BB.

FIG. 27 illustrates the consistent synergic effect of combined nicotinamide and FGF4 on the expansion (cumulative cell count) throughout 5 passages.

Example 2

The Effect of Nicotinamide on Bone Marrow Derived Mesenchymal Stem Cell Culture

The present inventors showed that nicotinamide increased the seeding efficacy (selection) of bone marrow derived MSCs. Phenotypic characterization of these cells after one passage in nicotinamide is shown in FIGS. 11 and 13. FIGS. 15, 17A-B, 22 and 26 illustrate the effect of nicotinamide on the expansion rate of bone marrow derived MSCs. Low concentrations of nicotinamide (e.g. 0.1 mM) had insignificant effect on the expansion rate of bone marrow derived MSCs (Figure not shown). FIGS. 20A-C and 21A-B illustrate that mesenchymal stem cells grown in the presence of nicotinamide are smaller and less granular than mesenchymal stem cells grown in the absence of nicotinamide under identical conditions.

Example 3

Nicotinamide Increases Expansion of Cultured Adipose Tissue-Derived Mesenchymal Cells Phenotypic characterization of adipose tissue derived MSCs is shown in FIG. 12. As illustrated in FIGS. 14 and 16, nicotinamide substantially improved adipose derived mesenchymal stem cell expansion in culture.

Example 4

Nicotinamide Increases Tissue Homing of Cultured Mesenchymal Cells

To evaluate the effect of nicotinamide on the homing of cultured mesenchymal cells, NOD/SCID mice are transplanted with either non-cultured mesenchymal cells, or with their total progeny following 3-weeks in culture with cytokines, with or without nicotinamide. Prior to transplantation, the cells are labeled with CFSE. Twenty-four hours post transplantation total CFSE-labeled cells and CFSE labeled mesenchymal cells that homed to the mouse bone marrow of the recipient mice are quantified by FACS.

Results indicate an effect of nicotinamide on tissue homing of mesenchymal cells, if the homing of nicotinamide-treated mesenchymal cells is significantly higher than the homing of non-cultured mesenchymal cells not subjected to nicotinamide Example 5

Nicotinamide Increases Functionality of Chemokine Receptors and Adhesion Molecules In order to determine the role of adhesion and related molecules in nicotinamide-mediated enhancement of homing and engraftment of cells, the effect of nicotinamide on in-vitro migration and the functionality of the adhesion molecules can be tested.

Using a trans-well migration assay, CXCL12-induced migration of non-cultured and cultured mesenchymal cells is tested, assessing the effects of nicotinamide on integrin and adhesion molecule function. Enhanced stimulation of migration in the nicotinamide treated cells, compared to the cells cultured without nicotinamide or non-cultured cells suggests that treatment of mesenchymal cells with nicotinamide can potentially increase the responsiveness of adhesion molecules to their ligands, resulting in enhanced engraftment and homing potential of the nicotinamide-treated cells.

The functional quality of cell binding to adhesion molecules can also be investigated using shear flow analysis. The strong effect of nicotinamide on adhesion molecule-mediated binding and retention on substrate adhesion molecules can be evidenced by significantly enhanced percentage of initially settled cells resistant to removal by shear stress evident in the mesenchymal cells treated with nicotinamide.

Example 6

Nicotinamide Increases the SCID-Repopulating Capacity of Cultured Cells

Nicotinamide treatment is tested for ability to enhance homing and engraftment of transplanted cells by repopulation of NOD/SCID mice. To evaluate repopulating capacity, NOD/SCID mice are transplanted with non-cultured mesenchymal cells (n=12) over a range of doses intended to achieve a sub-optimal transplantation, and subsequent non-engraftment in a fraction of mice or their progeny following 3-weeks expansion with cytokines. Human cell engraftment is evaluated 4-weeks post transplantation. Mice are scored as positively engrafted if 0.5% of the recipient bone marrow cells expressed human CD45 antigen (CD45+). In the event that the presence of nicotinamide in culture results in superior and clear engraftment of mesenchymal cells in the mice at a predetermined dose range, while the untreated cells fail to engraft or engraft poorly, it can be concluded that nicotinamide is effective in enhancing engraftment and homing of transplanted mesenchymal cells.

Example 7

Further Analysis on the Effect of Nicotinamide on Mesenchymal Stem Cells

Materials and Methods

Mesenchymal stem cells were isolated using plastic adherence method, as described above and cultured for several passages with fetal bovine serum, ±NAM. The cells were selected in the presence of NAM.

At about 80% confluence, adherent cells were collected following trypsin treatment, counted, characterized and re-seeded at a concentration of $1 \times 10^3$ cells/cm$^2$.

Measurement of VCAM1/CD106:

Following Trypsin treatment the cells were analyzed for CD 106 expression in FACS using anti-human CD 106 PE antibodies.

Measurement of CD54:

Following Trypsin treatment the cells were analyzed for CD54 expression in FACS using anti-human CD54 antibodies.

Results

FIG. 18 illustrates that the effect of nicotinamide on cell count was evident on large batches of mesenchymal stem cells indicating that large commercial batches of MSCs can be manufactured with less passages. This ensures better quality of the therapeutic cells due to shorter cultivation time and preservation of stem cells characteristics by nicotinamide.

FIG. 19 illustrates that the effect of nicotinamide is not dependent on a particular batch of serum, and presents the results of one of two experiments performed. The cultures on these experiments were treated individually (each group was passaged upon reaching confluence).

The amount of senescent cells was reduced following culture in nicotinamide (FIGS. 23A-D).

FIG. 24A illustrates that mesenchymal stem cells grown in the presence of nicotinamide express more VCAM1/CD106 adhesion molecule than mesenchymal stem cells grown in the absence of nicotinamide under identical conditions.

FIG. 24B illustrates that mesenchymal stem cells grown in the presence of nicotinamide express less CD54 than mesenchymal stem cells grown in the absence of nicotinamide under identical conditions.

FIG. 25 illustrates that mesenchymal stem cells grown in the presence of nicotinamide have higher ability to perform wound closure than mesenchymal stem cells grown in the absence of nicotinamide under identical conditions.

Example 8

Effect of Combined Nicotinamide and FGF4 on Expression of Growth Factors in Cultured Mesenchymal Stem Cells Culture of mesenchymal stem cells in the presence of nicotinamide and FGF4 provides a synergic increase in expansion potential of the mesenchymal stem cells, while maintaining the cells in an undifferentiated state (see FIGS. 3A-3D, 4A-4B, 5A-5D and 27). In order to further characterize the MSCs expanded in these cultures, secretion of cytokines into the culture medium was measured by ELISA.

FIGS. 28 to 31 illustrate the significant increase in hepatocyte growth factor (HGF, FIG. 28), transforming growth factor beta (TGF-β, FIG. 29) and keratinocyte growth factor (KGF, FIG. 30) with combined FGF4 and nicotinamide, compared to nicotinamide alone. FIG. 31 shows nicotinamide's reduction in pro-inflammatory interleukin 6 (IL-6) secreted, and the further reduction in IL6 with addition of FGF4.

When medium from mesenchymal stem cell cultured with nicotinamide or nicotinamide and FGF4 was assayed for effect on inflammation in the in-vivo delayed hypersensitivity test, reduction in inflammatory response to challenge with the sensitizing allergen (Oxazolone) was clearly observed (data not shown). Further analysis in the ex-vivo mixed lymphocyte reaction-type assay clearly demonstrated the anti-inflammatory potential of the MSC culture medium from nicotinamide and nicotinamide with FGF4 in reducing secretion of TNFα by peripheral blood mononuclear cells in response to activation with PHA (data not shown).

When medium from mesenchymal stem cell cultured with nicotinamide or nicotinamide and FGF4 was assayed for effect on keratinocyte proliferation in-vitro, significant induction of keratinocyte proliferation was clearly observed (data not shown).

Thus, adherent mesenchymal stein cells cultured with nicotinamide and nicotinamide in combination with FGF4 release biologically active factors into the medium, including factors having anti-inflammatory and proliferation-inducing activity.

Example 9

Effect of Combined Nicotinamide and FGF4 on Adipose-Derived Mesenchymal Stem Cell in Culture Proliferation and cell size distribution in adipose-derived mesenchymal stem cells cultured with nicotinamide with or without additional FGF4 was assessed in up to 4 passages of the cultures.

FIGS. 32 to 33 illustrate the striking effect of combined nicotinamide and FGF4 on adipose derived adherent cell proliferation, expressed as the number of total nucleated cells in the cultures, compared to controls as well as nicotinamide-treated cultures.

The size of mesenchymal stem cells in culture is often used as an indicator of the degree of differentiation of the MSCs, with the undifferentiated state more prevalent in the smaller size cells. FIG. 34 illustrates the increased prevalence of smaller size cells in cultures of adipose derived MSCs exposed to nicotinamide, and the yet greater prevalence of smaller size cells among adipose derived MSCs exposed to nicotinamide and FGF4.

Thus, these results indicate that a combination of nicotinamide and FGF4 synergistically increases the rate of proliferation of adipose derived mesenchymal cells, while effectively maintaining the cells in an undifferentiated state.

Example 10

Effect of Nicotinamide and FGF4 on Hematopoietic Stem Cell Differentiation

In order to determine whether or not the effects of combined nicotinamide and FGF4 on mesenchymal stem cells are a specific or generalized phenomenon, hematopoietic stem cells were cultured with and without FGF4 and nicotinamide, and the degree of differentiation of component sub-populations assessed according to cell surface markers.

Materials and Methods

Umbilical cord-derived CD133+ hematopoietic stem cells were isolated and cultured for 3 weeks in medium supplemented with early-acting growth factors and fetal bovine serum, nicotinamide and/or FGF4. After 3 weeks in culture the cells were stained for surface markers (CD38, CD133, CD19) and the cell populations determined by FACS analysis. Cell proliferation was assessed by counting total cells at three weeks.

Results:

FGF4 does not Affect Differentiation of Hematopoietic Stem Cells in Culture:

When hematopoietic early progenitor cells (CD133+) are cultured for 3 weeks in the presence of 2.5 or 5 mM nicotinamide, the proportion of differentiated cells decreases significantly, and increase in the stem and progenitor cell fraction is clearly observed (see FIG. 35, columns 1, 2 and 3). Exposure of the cells to 10 to 200 ng/ml FGF4, on the other hand, is without any effect on the degree of differentiation at three weeks culture, as evidenced by the fraction of CD38 and CD133-expressing cells (see FIGS. 35 and 36, columns 1 and 4-6). Addition of FGF4, with or without nicotinamide was also without any discernible effect on total cell proliferation in cultures (results not shown).

Addition of FGF4 to cells cultured with nicotinamide neither improved nor reduced nicotinamides inhibition of hematopoietic stem cell differentiation, at any concentration of FGF4 (see, FIGS. 35-36, lanes 1 and 7-12).

FGF4 does not Affect Differentiation of HSC into Committed Myeloid or Lymphoid Lineage:

In order to determine whether committed hematopoietic stem cells were affected by exposure to FGF4 during culturing, the abundance of cells expressing CD33 and CD19, representing differentiated committed lineage myeloid and lymphoid cells, respectively, was measured in the three week cultures. While nicotinamide consistently reduced the committed cell fraction (see FIGS. 37 and 38, lanes 1-3 and 7-12), addition of FGF4, alone or in combination with nicotinamide, was without any effect on the abundance of committed myeloid or lymphoid cells (see FIGS. 37 and 38, lanes 1, 4-6 and 7-12).

Thus, these results clearly indicate that the proliferation-enhancing effects of FGF4 observed in mesenchymal stem cell culture, and the synergic effects of exposure of mesenchymal stem cells to combined nicotinamide and FGF4 are not a general phenomenon, and are not observed in ex-vivo hematopoietic stem cell cultures.

Example 11

Combined Use of Nicotinamide+/−FGF4 Followed by Selection Using VCAM1/CD106. CD105 or STRO-1 for Selection and Expansion of Mesenchymal Stem Cells Materials and Methods
Isolation:
Bone marrow derived and adipose tissue derived mesenchymal cells are isolated based on their plastic adherence potential in expansion medium containing: High glucose DMEM and 10% Fetal Bovine Serum (FBS, Hyclone, Logan, Utah, USA), 0.05 mg/ml Gentamicin (Sigma) and 2 mM L-glutamine (Biological Industries, Israel). Cells are allowed to adhere in the presence of nicotinamide+/−FGF4 for 3-4 days and non-adherent cells were washed out with medium changes.

Mesenchymal stem cells are cultured for several passages (1-3) with fetal bovine serum, +NAM, ±FGF4. The cells may be cultured on plastic adherent plates.

At about 80% confluence, adherent cells are collected following trypsin treatment, counted, characterized and selected by CD105, CD106 or STRO-1 expression using directly or indirectly conjugated mouse anti-human antibodies (Miltenyi Biotec) and magnetic cell sorting (MACS) or Fluorescence-activated cell sorting (FACS) and re-seeded for further expansion.

Measurement of VCAM1/CD106, CD105 or STRO-1:
following trypsin treatment the cells are analyzed for CD106 expression, STRO-1 expression or CD105 in FACS using anti-human CD106 PE antibodies, anti-human CD105 antibodies or anti-STRO-1 antibodies.

Example 12

Combined Use of Nicotinamide+/−FGF4 Preceded by Selection Using VCAM1/CD106. CD105 or STRO-1 for Selection of Mesenchymal Stem Cells Materials and Methods
Selection of Bone Marrow Derived and Adipose Tissue Derived MSC:
Bone marrow derived and adipose tissue derived mesenchymal cells are selected by CD105, CD106 or STRO-1 expression using directly or indirectly conjugated mouse anti-human antibodies (Miltenyi Biotec) and magnetic cell sorting (MACS). The selected cells are seeded at concentration of $6 \times 10^3$ cells/cm$^2$ in expansion medium containing: High glucose DMEM and 10% Fetal Bovine Serum (FBS, Hyclone, Logan, Utah, USA), 0.05 mg/ml Gentamicin (Sigma) and 2 mM L-glutamine (Biological Industries, Israel). Cells are allowed to adhere for 3-4 days and non-adherent cells were washed out with medium changes.

Culture of Selected MSCs Populations in NAM±FGF4:
Mesenchymal Stem cells are cultured for several passages with fetal bovine serum, +NAM, ±FGF4.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A method of expanding undifferentiated mesenchymal stem cells (MSCs) comprising culturing a population of MSCs comprising undifferentiated MSCs in a medium comprising nicotinamide and fibroblast growth factor 4 (FGF4) wherein said medium is devoid of basic fibroblast growth factor, (bFGF), platelet derived growth factor (PDGF) and erythrocyte growth factor (EGF), thereby generating an expanded population of cultured undifferentiated MSCs.

2. The method of claim 1, wherein said medium comprises DMEM.

3. The method of claim 1, wherein said medium comprises serum or platelet lysate.

4. The method of claim 1, wherein the mesenchymal stem cells are derived from a tissue selected from the group consisting of bone marrow, adipose tissue, placenta and umbilical cord blood.

5. The method of claim 1, wherein said nicotinamide is selected from the group consisting of nicotinamide, a nicotinamide analog, a nicotinamide metabolite, a nicotinamide analog metabolite and derivatives thereof.

6. The method of claim 1, wherein said culturing is effected on a plastic surface.

7. The method of claim 1, wherein said population of MSCs is comprised in a heterogeneous population of cells.

8. The method of claim 1, wherein a calcium concentration of said medium is greater than 1.8 mM.

9. The method of claim 1, wherein a concentration of said nicotinamide is 1-20 mM.

10. The method of claim 1, wherein said medium is devoid of platelet derived growth factor (PDGF).

11. The method of claim 1, wherein said undifferentiated MSC are a seeded population of mesenchymal stem cells cultured in a medium devoid of nicotinamide prior to said culturing in the medium comprising nicotinamide and FGF4.

12. The method of claim 11, wherein said culturing in said medium comprising nicotinamide and FGF-4 is effected for at least one week.

13. The method of claim 11, wherein said culturing in said medium comprising nicotinamide and FGF-4 or said medium devoid of nicotinamide is effected in a medium comprising calcium, wherein a concentration of said calcium is greater than 1.8 mM.

\* \* \* \* \*